US005658780A

United States Patent [19]
Stinchcomb et al.

[11] Patent Number: 5,658,780
[45] Date of Patent: Aug. 19, 1997

[54] REL A TARGETED RIBOZYMES

[75] Inventors: Dan T. Stinchcomb; Kenneth G. Draper; James McSwiggen, all of Boulder, Colo.

[73] Assignee: Ribozyme Pharmaceuticals, Inc., Boulder, Colo.

[21] Appl. No.: 291,932

[22] Filed: Aug. 15, 1994

Related U.S. Application Data

[63] Continuation-in-part of Ser. No. 245,466, May 18, 1994, abandoned, which is a continuation-in-part of Ser. No. 987,132, Dec. 7, 1992, abandoned.

[51] Int. Cl.$^6$ .................... C12Q 1/68; C12N 15/85; A61K 48/00; C07H 21/04
[52] U.S. Cl. .................... 235/366; 435/6; 435/91.31; 435/172.1; 435/172.3; 435/325; 435/32.1; 536/23.1; 536/23.2; 536/24.5; 514/44
[58] Field of Search .................... 435/6, 91.31, 172.1, 435/172.3, 240.1, 240.2; 536/23.1, 23.2, 24.5; 514/44

[56] References Cited

U.S. PATENT DOCUMENTS

| | | | |
|---|---|---|---|
| 4,987,071 | 1/1991 | Cech | 435/91.31 |
| 5,168,053 | 12/1992 | Altman | 514/44 |
| 5,213,580 | 5/1993 | Slepian et al. | 623/1 |
| 5,328,470 | 7/1994 | Nabel et al. | 604/1 |

FOREIGN PATENT DOCUMENTS

| | | |
|---|---|---|
| 9103162 | 3/1991 | WIPO. |
| 9115580 | 10/1991 | WIPO. |
| 9118624 | 12/1991 | WIPO. |
| 9118625 | 12/1991 | WIPO. |
| 9118913 | 12/1991 | WIPO. |
| 9200080 | 1/1992 | WIPO. |
| 9207065 | 4/1992 | WIPO. |
| 9220348 | 11/1992 | WIPO. |
| 9302654 | 2/1993 | WIPO. |
| 9308845 | 5/1993 | WIPO. |
| 9309789 | 5/1993 | WIPO. |
| 9315187 | 8/1993 | WIPO. |
| 9323569 | 11/1993 | WIPO. |
| 9402595 | 2/1994 | WIPO. |

OTHER PUBLICATIONS

Ballantyne et al., "Nucleotide sequence of the cDNA for murine intercellular adhesion molecule–1 (ICAM–1)," *Nucleic Acids Research* 17:5853 (1989).

Barinaga, "Ribozymes: Killing the Messenger," *Science* 262:1512–1514 (1993).

Cotten, "The in vivo application of ribozymes," *TIBTECH* 8:174–178 (1990).

Edgington, "Ribozymes: Stop Making Sense," *Biotechnology* 10:256–262 (1992).

Kita et al., "Sequence and expression of rat ICAM–1," *Biochem. Biophys. Acta* 1131:108–110 (1992).

Simons et al., "ICAM, an adhesion ligand of LFA–1, is homologous to the neutral cell adhesion molecule NCAM," *Nature* 331:624–627 (1988).

Akhtar and Juliano, "Cellular Uptake and Intracellular Fate of AntiSense Oligonucleotides," *Trends Cell Biol.* 2:139–144 (1992).

Alitalo et al., "Aberrant Expression of An Amplified c–myb oncogene in two cell lines from a colon carcinoma," *Proc. Natl. Acad. Sci. USA* 81:4534–4538 (1984).

Anfossi et al., "An oligomer complementary to c–myb–encoded mRNA inhibits proliferation of human myeloid leukemia cell lines," *Proc. Natl. Acad. Sci. USA* 86:3379–3383 (1989).

Austin et al., "Intimal Proliferation of Smooth Muscle Cells as an Explanation for Recurrent Coronary Artery Stenosis After Percutaneous Transluminal Coronary Angioplasty," *J. Am. Coll. Cardiol.* 6:369–375 (1985).

Banskota et al., "Insulin, Insulin–Like Growth Factor I and Platelet–Derived Growth Factor Interact Additively in the Induction of the Protooncogene c–myc and Cellular Proliferation in Cultured Bovine Aortic Smooth Muscle Cells," *Molec. Endocrinol.*, 3:1183–1190 (1989).

Belknap et al., "Transcriptional Regulation in Vascular Cells: Genetically Modified Animals," *J. Cell. Biochem.* S18A:277 (1994).

Bennett et al., "Cationic Lipids Enhance Cellular Uptake and Activity of Phosphorothioate Antisense Oligonucleotides," *Mol. Pharmacology*, 41:1023–1033 (1992).

Biotech Abstracts Act. #91–00050 EP 388758 (Sep. 26, 1990).

Biro et al., "Inhibitory Effects of Antisense Oligodeoxynucleotides targeting c–myc mRNA on smooth muscle cell proliferation and migration," *Proc. Natl. Acad. Sci. U S A*, 90:654–658 (1993).

Blam et al., "Addition of Growth Hormone Secretion Signal to Basic Fibroblast Growth Factors Results in Cell Transformation and Secretion of Aberrant Forms of the Protein," *Oncogene* 3:129–136 (1988).

Brown et al., "Expression of the c–myb Proto–oncogene in Bovine Vascular Smooth Muscle Cells," *J. Biol. Chem.* 267:4625–4630 (1992).

Bywater et al., "Expression of Recombinant Platelet–Derived Growth Factor A–Chain and B–Chaim Homodimers in Rat Cells and Human Fibroblastic Reveals Difference in Protein Processing and Autocrine Effects," *Mol. Cell Biol.* 8:2753–2762 (1988).

Calabretta et al., "Normal and Leukemic Hematopoietic Cells Manifest Differential Sensitivity to Inhibitory Effects of c–myb Antisense Oligodeoxynucleotides: An in vitro study relevant to bone marrow purging," *Proc. Natl. Acad. Sci. USA*, 88:2351–2355 (1991).

Califf et al., "Restenosis: The Clinical Issues," in *Textbook of Interventional Cardiology*, E.J. Topol, ed., W. B. Saunders, Philadelphia, pp. 363–394 (1990).

Cameron and Jennings, "Specific Gene Suppression by Engineered Ribozymes in Monkey Cells," *Proc. Natl. Acad. Sci. USA* 86:9139 (1989).

(List continued on next page.)

Primary Examiner—John LeGuyader
Attorney, Agent, or Firm—Lyon & Lyon

[57] ABSTRACT

Enzymatic RNA molecules which cleave rel A mRNA.

13 Claims, 6 Drawing Sheets

OTHER PUBLICATIONS

Chen, "Multitarget-Ribozyme Directed to Cleave at up to Nine Highly Conserved HIV-1 env RNA Regions Inhibits HIV-1 Replication-Potential Effectiveness Against Most Presently Sequenced HIV-1 Isolates," *Nucleic Acids Res.* 20:4581–4589 (1992).

Chowrira and Burke, "Extensive Phosphorothioate Substitution Yields Highly Active and Nuclease-Resistant Hairpin Ribozymes," *Nucleic Acids Res.* 20:2835–2840 (1992).

Chuat and Galibert, "Can Ribozymes be Used to Regulate Procaryote Gene Expression?" *Biochem. and Biophys. Res. Comm.* 162:1025 (1989).

Cleary et al., "Cloning and Structural Analysis of cDNAs For bcl-2 And A Hybrid bcl-2/Immunoglobulin Transcript Resulting From the t(14;18) Translocation," *Cell* 47:199–28 (1986).

Clowes et al., "Kinetics of Cellular Proliferation After Arterial Injury," *Lab Invest.* 49:327–333 (1983).

Collins and Olive, "Reaction Conditions and Kinetics of Self-Cleavage of a Ribozyme Derived From Neurospora VS RNA," *Biochemistry* 32:2795–2799 (1993).

Cotten et al., "High-Efficiency Receptor-Mediated Delivery of Small and Large (48 Kilobase Gene Constructs using the Endosome-Disruption Activity of Defective or Chemically Inactivated Adenovirus Particles," *Proc. Natl. Acad. Sci. USA* 89:6094–6098 (1992).

Cotten et al., "Transferrin-Polycation-Mediated Introduction of DNA into Human Leukemic Cells: Stimulation by Agents that Affect the Survival of Transfected DNA or Modulate Transferrin Receptor Levels" (Abstract), *Proc. Natl. Acad. Sci. USA* 87:4033–4037 (1990).

Cotten et al., "Chicken Adenovirus (CELO Virus) Particles Augment Receptor-Mediated DNA Delivery to Mammalian Cells and Yield Exceptional Levels of Stable Transformants," *J. Virol.* 67:3777–3785 (1993).

Cristiano et al., "Hepatic Gene Therapy: Adenovirus Enhancement of Receptor-Mediated Gene Delivery and Expression in Primary Hepatocytes," *Proc. Natl. Acad. Sci. USA* 90:2122–2126 (1993).

Curiel et al., "Adenovirus Enhancement of Transferrin-Polylysine-Mediated Gene Delivery," *Proc. Natl. Acad. Sci. USA*, 88:8850–8854 (1991).

Dropulic et al., "Functional Characterization of a U5 Ribozyme: Intracellular Suppression of Human Immunodeficiency Virus Type I Expression," *J Virol.* 66:1432–1441 (1992).

Eck et al., *Mol. Cell. Biol.* 13:6530–6536 (1993).

Ege et al., "Enhancement of DNA-Mediated Gene Transfer by Inhibitors of Autophagic-Lysosomal Function," *Exp. Cell Res.* 155:9–16 (1984).

Elroy-Stein and Moss, "Cytoplasmic Expression System Bassed on Constitutive Synthesis of Bacteriophage T7 RNA Polymerase in Mammalian Cells," *Proc. Natl. Acad. Sci. USA* 87:6743–7 1990).

Ferguson et al., "Compensation for Treating Wounds to Inhibit Scar Tissue—Contains Agent Esp. Antibody, Which Selectively Neutralises Fibrotic Growth Factors," WPI Acc#92–3659974/44.

Ferns et al., "Inhibition of Neointimal Smooth Muscle Accumulation After Angioplasty by an Antibody to PDGF," *Science* 253:1129–1132 (1991).

Gao and Huang, "Cytoplasmic Expression of a Reporter Gene by Co-Delivery of T7 RNA Polymerase and T7 Promoter Sequence with Cationic Liposomes," *Nucleic Acids Res.* 21:2867–72 (1993).

Garratt et al., "Differential Histopathology of Primary Atherosclerotic and Restenotic Lesions in Coronary Arteries and Saphenous Vein Bypass Grafts: Analysis of Tissue Obtained From 73 Patients by Directional Atherectomy," *J. Am. Coll. Cardio.* 17:442–428 (1991).

Goldberg et al., "Vascular Smooth Muscle Cell Kinetics: A New Assay for Studying Patterns of Cellular Proliferation in vivo," *Science* 205:920–922 (1979).

Griffin and Baylin, "Expression of the c-myb Oncogene in Human Small Cell Lung Carcinoma," *Cancer Res.* 45:272–275 (1985).

Grotendorst et al., "Attachment of Smooth Muscle Cells to Collagen and Their Migration Toward Platelet-Derived Growth Factor," *Proc. Natl. Acad. Sci. USA* 78:3669–3672 (982).

Guerrier-Takada et al., "The RNA Moiety of Ribonuclease P Is the Catalytic Subunit of the Enzyme," *Cell* 35:849 (1983).

Hajjar et al., "Tumor Necrosis Factor-Mediated Release of Platelet-Derived Growth Factor From Cultured Endothelial Cells," *J. Exp. Med.* 166:235–245 (1987).

Hampel et al., "'Hairpin' Catalytic RNA Model: Evidence for Helices and Sequence Requirement for Substrate RNA", *Nucleic Acids Research* 18:299–304 (1990).

Harris et al., "Receptor-Mediated Gene Transfer to Airway Epithelial Cells in Primary Culture," *Am. J. Respir. Cell Mol. Biol.*, 9:441–447 (1993).

Haseloff and Gerlach, "Simple RNA Enzymes with New and Highly Specific Endoribonuclease Activities," *Nature* 334:585–591 (1988).

Herschlag, "Implications of Ribozyme Kinetics for Targeting the Cleavage of Specific RNA Molecules in vivo: More Isn't Always Better," *Proc. Natl. Acad. Sci. USA* 88:6921–5 (1991).

Hertel et al., "Numbering System for the Hammerhead," *Nucleic Acids Res.* 20:3252 (1992).

Higashiyama et al., "A Heparin-Binding Growth Factor Secreted by Macrophage-Like Cells That is Related to EFG," *Science* 251:936–939 (1991).

Jaeger et al., "Improved Predictions of Secondary Structures for RNA," *Proc. Natl. Acad. Sci. USA* 86:7706–7710 (1989).

Jeffries and Symons, "A Catalytic 13-mer Ribozyme," *Nucleic Acids Research* 17:1371 (1989).

Kashani-Sabet et al., "Reversal of the Malignant Phenotype by an Anti-ras Ribozyme," *Antisense Research & Development* 2:3–15 (1992).

Kaye et al., "Structure and Expression of the Human L-myc Gene Reveal a Complex Pattern Of Alternative mRNA Processing," *Mol. Cell. Biol.* 8:186–195 (1988).

Kindy and Sonenshein, "Regulation of Oncogene Expression in Cultured Aortic Smooth Muscle Cells," *J. Biol. Chem.* 261:12865–12868 (1986).

Kitajima et al., *Science* 258:1792–1795 (1992).

Klagsbrun and Edelman, "Biological and Biochemical Properties of Fibroblast Growth Factors," *Arteriosclerosis* 9:269–278 (1989).

Koizumi et al., "Ribozymes Designed to Inhibit Transformation of NIH3T3 Cells by the Activated c-Ha-ras Gene," *Gene* 117:179 (1992).

Komuro et al., "Endothelin stimulates c–fos and c–myc expression and proliferation of vascular smooth muscle cells," *FEBS Letters* 238:249–252 (1988).

Kunapuli et al., "Molecular Cloning of Human Angiotensinogen cDNA and Evidence for the Presence of Its mRNA in Rat Heart—DNA Sequence," *Circ. Res.* 60:786–790 (1987).

Kunsch and Rosen, *Mol. Cell. Biol.* 13:6137–6146 (1993).

La Rosa et al., *Mol. Cell. Biol.* 14:1039–1044 (1994).

Lenardo and Baltimore, *Cell* 58:227–229 (1989).

Lieber et al., "Stable High–Level Gene Expression in Mammalian Cells by T7 Phage $NA Polymerase," *Methods Enzymol.* 217:47–66 (1993).

L'Huillier et al., "Cytoplasmic Delivery of Ribozymes Leads to Efficient Reduction in α–Lactalbumin mRNA Levels in C1271 Mouse," *Embo J.* 11:4411–4418 (1992).

Lindner and Reidy, "Proliferation of Smooth Muscle Cells After Vascular Injury Is Inhibited by an Antibody Against Basic Fibroblast Growth Factor," *Proc. Natl. Acad. Sci. USA* 88:3739–3743 (1991).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. USA* 90:8000–8004 (1993).

Liu et al., *J. Virology* 66:3883–3887 (1992).

Majello et al., "Human c–myb Protooncogene: Nucleotide Sequence of cDNA and Organization of the Genomic Locus," *Proc. Natl. Acad. Sci. USA* 83:9636–9640 (1986).

Mamone et al., "Design of Hammerhead Ribozymes Targeted to Sequences in HIV, HSV and the RAT ANF Gene," Abstract of Keystone, CO (May 27, 1992).

McGrath et al., "Structure and Organization of the Human Ki–ras Protooncogene And a Related Processed Pseudogene," 304:501–506 (1983).

Melani et al., "Inhibition of Proliferation by c–myb Antisense Oligodeoxynucleotide in Colon Adenocarcinoma Cell Lines that Express c–myb," *Cancer Res.* 51:2897–2901 (1991).

Minvielle et al., "A Novel Calcitonin Carboxyl–Terminal Peptide Produced in Medullary Thyroid Carcinoma by Alternative RNA Processing of the Calcitonin–Calcitonin Gene–Related Peptide Gene," *J. Biol. Chem.* 266:24627–24631 (1991).

Nabel et al., "Site–Specific Gene Expression in Vivo by Direct Gene Transfer Into the Arterial Wall," *Science* 249:1285–1288 (1990).

Nabel et al., "Recombinant Platelet–Derived Growth Factor B Gene Expression in Porcine Arteries Induces Intimal Hyperplasia In Vivo," *J. Clin. Invest.* 91:1822–1829 1993).

Narayanan et al., *Mol. Cell. Biol.* 13:3802–3810 (1993).

O'Brien et al., *J. Clin. Invest.* 92:945–951 (1993).

Ohno et al., "Gene Therapy for Vascular Smooth Muscle Cell Proliferation After Arterial Injury," *Science* 26:781–784 (1994).

Ohkawa et al., *Nucleic Acids Symp. Ser.* 27:15–6 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Pavco et al., "Regulation of Self–Splicing Reactions by Antisense RNA," Abstract of Keystone, CO (May 27, 1992).

Perkins, et al., *Proc. Natl. Acad. Sci. USA* 89:1529–1533 (1992).

Perreault et al., "Mixed Deoxyribo–and Ribo–Oligonucleotides with Catalytic Activity," *Nature* 344:565–568 (1990).

Perrotta and Been, "Cleavage of Oligoribonucleotides by a Ribozyme Derived from the Hepatitis ε Virus RNA Sequence," *Biochemistry* 31:16 (1992).

Pieken et al., "Kinetic Characterization of Ribonuclease–Resistant 2'–Modified Hammerhead Ribozymes," *Science* 253:314–317 (1991).

Popoma et al., "Clinical Trials of Restenosis After Coronary Angioplasty," *Circulation* 84:1426–1436 (1991).

Raines et al., "Interleukin–1 Mitogenic Activity for Fibroblasts and Smooth Muscle Cells Is Due to PDGF–AA," *Science* 243:393–396 (1989).

Raschella et al., "Inhibition of Proliferation by c–myb Antisense RNA and Oligodeoxynucleotides in Transformed Neuroectodermal Cell Lines," *Cancer Res.* 52:4221–4226 (1992).

Ratajczak et al., "In Vivo Treatment of Human Leukemia in a scid Mouse Model With c–myb Antisense Oligodeoxynucleotides," *Proc. Natl. Acad. Sci. USA* 89:11823–11827 (1992).

Ray and Prefontaine, *Proc. Natl. Acad. Sci. USA* 91:752–756 (1994).

Read et al., *J. Exp. Med.* 179:503–512 (1994).

Riessen et al., "Arterial Gene Transfer Using Pure DNa Applied Directly to a Hydrogel–Coated Angioplasty Balloon," *Human Gene Therapy* 4:749–758 (1993).

Ross et al., "A Platelet–Dependent Serum Factor That Stimulates the Proliferation of Arterial Smooth Muscle Cells In Vitro," *Proc. Natl. Acad. Sci. USA* 71:1207–1210 (1974).

Roessler et al., *J. Clin. Invest.*, 92:1085–1092 (1993).

Rossi et al., *J. Cell Biochem.* Suppl 14A:D428 (1990).

Rossi et al, "Ribozymes as Anti–HIV–1 Therapeutic Agents: Principles, Applications, and Problems," *Aids Research and Human Retroviruses* 8:183 (1992).

Ruben et al., "Isolation of a rel–related human cDNA that potentially encodes the 65–kD subunit of NF, kappba B," *Science* 251:5000 (1991).

Ruben et al., "Isolation of a rel–related human cDNA that potentially encodes the 65–kD subunit of NF, kappba B," *Science* 254:5028 (1991).

Sarver et al., "Ribozymes as Potential Anti–HIV–1 Therapeutic Agents," *Science* 247:1222–1225 (1990).

Sarver et al., "Catalytic RNAs (Ribozymes): A New Frontier in Biomedical Applications," *AIDS Res. Revs.* 2:259 (1992).

Saville and Collins, "A Site–Specific Self–Cleavage Reaction Performed by a Novel RNA In Neurospora Mitochondria," *Cell* 61:685–696 (1990).

Saville and Collins, "RNA–Mediated Ligation of Self–Cleavage Products of a Neurospora Mitochondrial Plasmid Transcript," *Proc. Natl. Acad. Sci. USA* 88:8826–8830 (1991).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Semba, "A v–erbB–Related Protooncogene, C–erB–2, Is Distinct From the c–erB–1/Epidermal Growth Factor–Receptor Gene and Is Amplified in A Human Salivary Gland Adenocarcinoma," *Proc. Natl. Acad. Sci. USA* 82:6497–6501 (1985).

Seth et al., "Mechanism of Enhancement of DNA Expression Consequent to Cointernalization of a Replication-Deficient Adenovirus and Unmodified Plasmid dDNA," *J. Virol.*, 68:933–940 (1994).

Sessa et al., "Molecular Cloning and Expression of a cDNA Encoding Endothelial Cell Nitric Oxide Synthase," *J. Biol. Chem.* 267:15274–15276 (1992).

Shi et al., "Downregulation of c–myc Expression by Antisense Oligonucleotides Inhibits Proliferation of Human Smooth Muscle Cell," *Circulation* 88:1190–1195 (1993).

Shu et al., *Mol. Cell. Biol.* 13:6283–6289 (1993).

Simons et al., "Antisense c–mby Oligonucleotides Inhibit Intimal Arterial Smooth Muscle Cell Accumulation in vivo," *Nature* 359:67–70 (1992).

Simons et al., "Relation Between Activated Smooth Muscle Cells in Coronary–Artery Lesions and Restenosis After Atherectomy," *New Engl. J. Med.* 328:608–613 (1993).

Sioud and Drulica, "Prevention of Human Immunodeficiency Virus Type 1 Integrase Expression in *Escherichia coli* by a Ribozyme," *Proc. Natl. Acad. Sci. USA* 88:7303 (1991).

Sjolund et al., "Arterial Smooth Muscle Cells Express Platelet–Derived Growth Factor (PDGF) A Chain mRNA, Secrete a PDGF–Like Mitogen, and Bind Exogenous PDGF in a Phenotype–and Growth State–Dependent Manner," *J. Cell. Biol.* 106:403–413 (1988).

Slamon et al., "Studies of the Human c–myb Gene and Its Products In Human Acute Leukemias," *Science* 233:3467–351 (1986).

Slamon et al., "Expression of Cellular Oncogenes in Human Malignancies," *Science* 224:256–262 (1984).

Taira et al., "Construction of a novel RNA–transcript–trimming plasmid which can be used both in vitro in place of run–off and (G)–free transcriptions and in vivo as multi-sequences transcription vectors," *Nucleic Acids Research* 19:5125–30 (1991).

Ten Dijke et al., "Recombinant Transforming Growth Factor Type Beta–3 Biological Activities and Receptor–Binding Properties in Isolated Bone Cells," *Mol. Cell Biol.* 10:4473–4479 (1990).

Tessler et al, "Basic Fibroblast Growth Factor Accumulates in the Nuclei of Vairous BFGF–Producing Cell Types," *J. Cell. Physiol.* 145:310–317 (1990).

Thiele et al., "Regulation of c–myb Expression in Human Neuroblastoma Cells During Retinoic Acid–Induced Differentiation," *Mol. Cell. Biol.* 8:1677–1683 (1988).

Torelli et al., "Expression of c–myb Protoncogene and Other Cell Cycle–Related Genes in Normal and Neoplastic Human Colonic Mucosa," *Cancer Res.* 47:5266–5269 (1987).

Uhlenbeck, "A Small Catalytic Oligoribonucleotide," *Nature* 327:596–600 (1987).

Usman and Cedergren, "Exploiting the chemical synthesis of RNA," *Trends in Biochem. Sci.* 17:334–339 (1992).

Usman et al., "Automated Chemical Synthesis of Long Oligoribonucleotides Using 2'–O–Silylated Ribonucleoside 3'–O–Phosphoramidtes on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

van de Stolpe et al., *J. Biol. Chem.* 269:6185–6192 (1994).

Ventura et al., "Activation of HIV–Specific Ribozyme Activity by Self–Cleavage," *Nucleic Acids Res.* 21:3249–55 (1993).

Weerasinghe et al., "Resistance to Human Immunodeficiency Virus Type 1 (HIV–1) Infection in Human $CD4^+$ Lymphocyte–Derived Cell Lines Conferred by using Retroviral Vectors Expressing an HIV–1 RNA–Specific Ribozyme," *Journal of Virology* 65:5531–4 (1994).

Weiser et al., "The Growth–Related Transcription Factor OCT–1 is Expressed as a Function of Vascular Smooth Muscle Cell Modulation," *J. Cell. Biochem.* S18A:282 (1994).

Westin et al., "Alternative Splicing of the Human c–myb Gene," *Oncogene* 5:1117–1124 (1990).

Willard et al., "*Circulation*" 86:1–473 (1992).

Woolf et al., "Specificity of Antisense Oligonucleotides in vivo," *Proc. Natl. Acad. Sci. USA* 89:7305–7309 (1992).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Zenke et al., "Receptor–mediated Endocytosis of Transferrin–Polycation Conjugates: An Efficient Way to Introduce DNA into Hematopoietic Cells" (Abstract) *Proc. Natl. Acad. Sci. USA* 87:3655–3659 (1990).

Zhou et al., "Synthesis of Function mRNA in Mammalian ells by Bacteriophage T3 RNA Polymerase," *Mol. Cell. Biol.* 10:4529–4537 (1990).

Stull et al. Pharm. Res. 12:465–483 (1995).

Ruba et al. Genes Ser. 6:745–760 (1992).

SEQUENCE LISTING ( 1 ) GENERAL INFORMATION:

( i i i ) NUMBER OF SEQUENCES: 830

( 2 ) INFORMATION FOR SEQ ID NO: 1:

( i ) SEQUENCE CHARACTERISTICS:
        ( A ) LENGTH: 11
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for
            any base. "H"represents
            nucleotide C, A, or U.

( x i ) SEQUENCE DESCRIPTION: SEQ ID NO: 1:

NNNNUHNNNN N                                                1 1

( 2 ) INFORMATION FOR SEQ ID NO: 2:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for
            any base.

( x i ) SEQUENCE DESCRIPTION: SEQ ID NO: 2:

NNNNNCUGAN GAGNNNNNNN NNNCGAAANN NN                  3 2

( 2 ) INFORMATION FOR SEQ ID NO: 3:

( i ) SEQUENCE CHARACTERISTICS:
        ( A ) LENGTH: 14
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for
            any base.

( x i ) SEQUENCE DESCRIPTION: SEQ ID NO: 3:

NNNNNGUCNN NNNN                                            1 4

( 2 ) INFORMATION FOR SEQ ID NO: 4:

( i ) SEQUENCE CHARACTERISTICS:
        ( A ) LENGTH: 50
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for
            any base.

( x i ) SEQUENCE DESCRIPTION: SEQ ID NO: 4:

NNNNNNAGAA NNNNACCAGA GAAACACACG UUGUGGUAUA UUACCUGGUA      5 0

( 2 ) INFORMATION FOR SEQ ID NO: 5:

( i ) SEQUENCE CHARACTERISTICS:

( A ) LENGTH: 85
( B ) TYPE: nucleic acid
( C ) STRANDEDNESS: single
( D ) TOPOLOGY: linear ( x i ) SEQUENCE DESCRIPTION: SEQ ID NO: 5:

| | | | | | | |
|---|---|---|---|---|---|---|
| UGGCCGGCAU | GGUCCCAGCC | UCCUCGCUGG | CGCCGGCUGG | GCAACAUUCC | GAGGGGACCG | 60 |
| UCCCCUCGGU | AAUGGCGAAU | GGGAC | | | | 85 |

( 2 ) INFORMATION FOR SEQ ID NO: 6:

( i ) SEQUENCE CHARACTERISTICS:
( A ) LENGTH: 176
( B ) TYPE: nucleic acid
( C ) STRANDEDNESS: single
( D ) TOPOLOGY: linear ( x i ) SEQUENCE DESCRIPTION: SEQ ID NO: 6:

| | | | | | | |
|---|---|---|---|---|---|---|
| GGGAAAGCUU | GCGAAGGGCG | UCGUCGCCCC | GAGCGGUAGU | AAGCAGGGAA | CUCACCUCCA | 60 |
| AUUUCAGUAC | UGAAAUUGUC | GUAGCAGUUG | ACUACUGUUA | UGUGAUUGGU | AGAGGCUAAG | 120 |
| UGACGGUAUU | GGCGUAAGUC | AGUAUUGCAG | CACAGCACAA | GCCCGCUUGC | GAGAAU | 176 |

( 2 ) INFORMATION FOR SEQ ID NO: 7:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 7:

AAUGGCUACA CAGGA                                                        15

( 2 ) INFORMATION FOR SEQ ID NO: 8:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 8:

AGCUCCUACG UGGUG                                                        15

( 2 ) INFORMATION FOR SEQ ID NO: 9:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 9:

CCUCCAUUGC GGACA                                                        15

( 2 ) INFORMATION FOR SEQ ID NO: 10:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 10:

GAUCUGUUUC CCCUC                                                        15

( 2 ) INFORMATION FOR SEQ ID NO: 11:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 11:

AUCUGUUUCC CCUCA        15

( 2 ) INFORMATION FOR SEQ ID NO: 12:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 12:

UUCCCUCAU CUUUC        15

( 2 ) INFORMATION FOR SEQ ID NO: 13:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 13:

CCCUCAUCUU UCCCU        15

( 2 ) INFORMATION FOR SEQ ID NO: 14:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 14:

CUCAUCUUUC CCUCA        15

( 2 ) INFORMATION FOR SEQ ID NO: 15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 15:

UCAUCUUUCC CUCAG        15

( 2 ) INFORMATION FOR SEQ ID NO: 16:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 16:

CAGGCUUCUG GGCCU        15

( 2 ) INFORMATION FOR SEQ ID NO: 17:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 17:

GGGCCUUAUG UGGAG  15

( 2 ) INFORMATION FOR SEQ ID NO: 18:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 18:

UGGAGAUCAU CGAAC  15

( 2 ) INFORMATION FOR SEQ ID NO: 19:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 19:

AGAUCAUCGA ACAGC  15

( 2 ) INFORMATION FOR SEQ ID NO: 20:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 20:

AUGCGAUUCC GCUAU  15

( 2 ) INFORMATION FOR SEQ ID NO: 21:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 21:

UGCGAUUCCG CUAUA  15

( 2 ) INFORMATION FOR SEQ ID NO: 22:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 22:

UUCCGCUAUA AAUGC  15

( 2 ) INFORMATION FOR SEQ ID NO: 23:

( i ) SEQUENCE CHARACTERISTICS:

(A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 23:

GGGCGCUCAG CGGGC                                                                    15

(2) INFORMATION FOR SEQ ID NO: 24:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 24:

GCAGUAUUCC UGGCG                                                                    15

(2) INFORMATION FOR SEQ ID NO: 25:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 25:

CACAGAUACC ACCAA                                                                    15

(2) INFORMATION FOR SEQ ID NO: 26:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 26:

CCACCAUCAA GAUCA                                                                    15

(2) INFORMATION FOR SEQ ID NO: 27:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 27:

UCAAGAUCAA UGGCU                                                                    15

(2) INFORMATION FOR SEQ ID NO: 28:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 28:

AAUGGCUACA CAGGA                                                                    15

(2) INFORMATION FOR SEQ ID NO: 29:

(i) SEQUENCE CHARACTERISTICS:
            (A) LENGTH: 15 base pairs
            (B) TYPE: nucleic acid ( C ) STRANDEDNESS: single
( D ) TOPOLOGY: linear ( x i ) SEQUENCE DESCRIPTION: SEQ ID NO: 29:

UUCGAAUCUC CCUGG                                                                15

( 2 ) INFORMATION FOR SEQ ID NO: 30:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 30:

CGAAUCUCCC UGGUC                                                                15

( 2 ) INFORMATION FOR SEQ ID NO: 31:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 31:

CCCUGGUCAC CAAGG                                                                15

( 2 ) INFORMATION FOR SEQ ID NO: 32:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 32:

GGCCCCUCCU CCUGA                                                                15

( 2 ) INFORMATION FOR SEQ ID NO: 33:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 33:

UCCACCUCAC CGGCC                                                                15

( 2 ) INFORMATION FOR SEQ ID NO: 34:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 34:

CCGGCCUCAU CCACA                                                                15

( 2 ) INFORMATION FOR SEQ ID NO: 35:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 35:

AUGAACUUGU GGGGA    15

( 2 ) INFORMATION FOR SEQ ID NO: 36:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 36:

AGAUCAUCGA ACAGC    15

( 2 ) INFORMATION FOR SEQ ID NO: 37:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 37:

GAUGGCUACU AUGAG    15

( 2 ) INFORMATION FOR SEQ ID NO: 38:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 38:

AUGGUCUCUC CGGAG    15

( 2 ) INFORMATION FOR SEQ ID NO: 39:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 39:

GGCUACUAUG AGGCU    15

( 2 ) INFORMATION FOR SEQ ID NO: 40:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 40:

CUGACCUCUG CCCAG    15

( 2 ) INFORMATION FOR SEQ ID NO: 41:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 41:

```
GCAGUAUCCA UAGCU                                                                    15
```

( 2 ) INFORMATION FOR SEQ ID NO: 42:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 42:

```
CCGCAGUAUC CAUAG                                                                    15
```

( 2 ) INFORMATION FOR SEQ ID NO: 43:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 43:

```
CAUAGCUUCC AGAAC                                                                    15
```

( 2 ) INFORMATION FOR SEQ ID NO: 44:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 44:

```
AUAGCUUCCA GAACC                                                                    15
```

( 2 ) INFORMATION FOR SEQ ID NO: 45:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 45:

```
UGGGGAUCCA GUGUG                                                                    15
```

( 2 ) INFORMATION FOR SEQ ID NO: 46:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 46:

```
GGCUCCUUUU CUCAA                                                                    15
```

( 2 ) INFORMATION FOR SEQ ID NO: 47:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 47:

```
GCUCCUUUUC UCAAG                                                                    15
```

( 2 ) INFORMATION FOR SEQ ID NO: 48:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 48:

CUCCUUUUCU CAAGC 15

( 2 ) INFORMATION FOR SEQ ID NO: 49:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 49:

UCCUUUUCUC AAGCU 15

( 2 ) INFORMATION FOR SEQ ID NO: 50:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 50:

UGGCCAUUGU GUUCC 15

( 2 ) INFORMATION FOR SEQ ID NO: 51:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 51:

AUUGUGUUCC GGACU 15

( 2 ) INFORMATION FOR SEQ ID NO: 52:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 52:

UUGUGUUCCG GACUC 15

( 2 ) INFORMATION FOR SEQ ID NO: 53:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 53:

GACUCCUCCG UACGC 15

( 2 ) INFORMATION FOR SEQ ID NO: 54:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 54:

CCUCCGUACG CCGAC　　　　　　　　　　　　　　　　　　　　　　　　15

( 2 ) INFORMATION FOR SEQ ID NO: 55:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 55:

CCAGGCUCCU GUUCG　　　　　　　　　　　　　　　　　　　　　　　　15

( 2 ) INFORMATION FOR SEQ ID NO: 56:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 56:

UUCGAGUCUC CAUGC　　　　　　　　　　　　　　　　　　　　　　　　15

( 2 ) INFORMATION FOR SEQ ID NO: 57:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 57:

CGAGUCUCCA UGCAG　　　　　　　　　　　　　　　　　　　　　　　　15

( 2 ) INFORMATION FOR SEQ ID NO: 58:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 58:

GCGGCCUUCU GAUCG　　　　　　　　　　　　　　　　　　　　　　　　15

( 2 ) INFORMATION FOR SEQ ID NO: 59:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 59:

CGGCCUUCUG AUCGC　　　　　　　　　　　　　　　　　　　　　　　　15

( 2 ) INFORMATION FOR SEQ ID NO: 60:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 60:

GCGAGCUCAG UGAGC         15

( 2 ) INFORMATION FOR SEQ ID NO: 61:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 61:

AUGGAGUUCC AGUAC         15

( 2 ) INFORMATION FOR SEQ ID NO: 62:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 62:

UGGAGUUCCA GUACU         15

( 2 ) INFORMATION FOR SEQ ID NO: 63:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 63:

UUCCAGUACU UGCCA         15

( 2 ) INFORMATION FOR SEQ ID NO: 64:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 64:

GCCUCAUCCA CAUGA         15

( 2 ) INFORMATION FOR SEQ ID NO: 65:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 65:

AGAUGAUCGC CACCG         15

( 2 ) INFORMATION FOR SEQ ID NO: 66:

( i ) SEQUENCE CHARACTERISTICS:
    ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO: 66:

CAGUACUUGC CAGAC 15

(2) INFORMATION FOR SEQ ID NO: 67:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 67:

ACCGGAUUGA AGAGA 15

(2) INFORMATION FOR SEQ ID NO: 68:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 68:

GAGACCUUCA AGAGU 15

(2) INFORMATION FOR SEQ ID NO: 69:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 69:

AGGACCUAUG AGACC 15

(2) INFORMATION FOR SEQ ID NO: 70:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 70:

GAGACCUUCA AGAGU 15

(2) INFORMATION FOR SEQ ID NO: 71:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 71:

AGACCUUCAA GAGUA 15

(2) INFORMATION FOR SEQ ID NO: 72:

(i) SEQUENCE CHARACTERISTICS:
(A) LENGTH: 15 base pairs
(B) TYPE: nucleic acid
(C) STRANDEDNESS: single ( D ) TOPOLOGY: linear ( x i ) SEQUENCE DESCRIPTION: SEQ ID NO: 72:

AGAGUAUCAU GAAGA  15

( 2 ) INFORMATION FOR SEQ ID NO: 73:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 73:

GAAGAGUCCU UUCAA  15

( 2 ) INFORMATION FOR SEQ ID NO: 74:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 74:

GAGUCCUUUC AAUGG  15

( 2 ) INFORMATION FOR SEQ ID NO: 75:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 75:

AGUCCUUUCA AUGGA  15

( 2 ) INFORMATION FOR SEQ ID NO: 76:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 76:

GUCCUUUCAA UGGAC  15

( 2 ) INFORMATION FOR SEQ ID NO: 77:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 77:

CCGGCCUCCA ACCCG  15

( 2 ) INFORMATION FOR SEQ ID NO: 78:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 78:

UACACCUUGA UCCAA　　　　　　　　　　　　　　　　　　　　　　　　　　15

( 2 ) INFORMATION FOR SEQ ID NO: 79:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 79:

GGCGUAUUGC UGUGC　　　　　　　　　　　　　　　　　　　　　　　　　　15

( 2 ) INFORMATION FOR SEQ ID NO: 80:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 80:

UGUGCCUACC CGAAA　　　　　　　　　　　　　　　　　　　　　　　　　　15

( 2 ) INFORMATION FOR SEQ ID NO: 81:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 81:

AAGCCUUCCC GAAGU　　　　　　　　　　　　　　　　　　　　　　　　　　15

( 2 ) INFORMATION FOR SEQ ID NO: 82:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 82:

CGAAACUCAA CUUCU　　　　　　　　　　　　　　　　　　　　　　　　　　15

( 2 ) INFORMATION FOR SEQ ID NO: 83:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 83:

CUCAACUUCU GUCCC　　　　　　　　　　　　　　　　　　　　　　　　　　15

( 2 ) INFORMATION FOR SEQ ID NO: 84:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 84:

UCAACUUCUG UCCCC 15

(2) INFORMATION FOR SEQ ID NO: 85:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 85:

CUUCUGUCCC CAAGC 15

(2) INFORMATION FOR SEQ ID NO: 86:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 86:

CAGCCCUACA CCUUC 15

(2) INFORMATION FOR SEQ ID NO: 87:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 87:

GCCAUAUAGC CUUAC 15

(2) INFORMATION FOR SEQ ID NO: 88:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 88:

CAUCCCUCAG CACCA 15

(2) INFORMATION FOR SEQ ID NO: 89:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 89:

ACACCUUCCC AGCAU 15

(2) INFORMATION FOR SEQ ID NO: 90:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 90:

UCCAUCUCCA GCUUC 15

( 2 ) INFORMATION FOR SEQ ID NO: 91:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 91:

UUUACUUUAG CGCGC 15

( 2 ) INFORMATION FOR SEQ ID NO: 92:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 92:

CCAGCAUCCC UCAGC 15

( 2 ) INFORMATION FOR SEQ ID NO: 93:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 93:

GCACCAUCAA CUUUG 15

( 2 ) INFORMATION FOR SEQ ID NO: 94:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 94:

AUCAACUUUG AUGAG 15

( 2 ) INFORMATION FOR SEQ ID NO: 95:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 95:

GAAGACUUCU CCUCC 15

( 2 ) INFORMATION FOR SEQ ID NO: 96:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 96:

AAGACUUCUC CUCCA 15

( 2 ) INFORMATION FOR SEQ ID NO: 97:

( i ) SEQUENCE CHARACTERISTICS:
     ( A ) LENGTH: 15 base pairs
     ( B ) TYPE: nucleic acid
     ( C ) STRANDEDNESS: single
     ( D ) TOPOLOGY: linear ( x i ) SEQUENCE DESCRIPTION: SEQ ID NO: 97:

GACUUCUCCU CCAUU                    15

( 2 ) INFORMATION FOR SEQ ID NO: 98:

( i ) SEQUENCE CHARACTERISTICS:
          ( A ) LENGTH: 15 base pairs
          ( B ) TYPE: nucleic acid
          ( C ) STRANDEDNESS: single
          ( D ) TOPOLOGY: linear ( x i ) SEQUENCE DESCRIPTION: SEQ ID NO: 98:

UUCUCCUCCA UUGCG                    15

( 2 ) INFORMATION FOR SEQ ID NO: 99:

( i ) SEQUENCE CHARACTERISTICS:
          ( A ) LENGTH: 15 base pairs
          ( B ) TYPE: nucleic acid
          ( C ) STRANDEDNESS: single
          ( D ) TOPOLOGY: linear ( x i ) SEQUENCE DESCRIPTION: SEQ ID NO: 99:

CCUCCAUUGC GGACA                    15

( 2 ) INFORMATION FOR SEQ ID NO: 100:

( i ) SEQUENCE CHARACTERISTICS:
          ( A ) LENGTH: 15 base pairs
          ( B ) TYPE: nucleic acid
          ( C ) STRANDEDNESS: single
          ( D ) TOPOLOGY: linear ( x i ) SEQUENCE DESCRIPTION: SEQ ID NO: 100:

AUGGACUUCU CUGCU                    15

( 2 ) INFORMATION FOR SEQ ID NO: 101:

( i ) SEQUENCE CHARACTERISTICS:
          ( A ) LENGTH: 15 base pairs
          ( B ) TYPE: nucleic acid
          ( C ) STRANDEDNESS: single
          ( D ) TOPOLOGY: linear ( x i ) SEQUENCE DESCRIPTION: SEQ ID NO: 101:

UGGACUUCUC UGCUC                    15

( 2 ) INFORMATION FOR SEQ ID NO: 102:

( i ) SEQUENCE CHARACTERISTICS:
          ( A ) LENGTH: 15 base pairs
          ( B ) TYPE: nucleic acid
          ( C ) STRANDEDNESS: single
          ( D ) TOPOLOGY: linear ( x i ) SEQUENCE DESCRIPTION: SEQ ID NO: 102:

GACUUCUCUG CUCUU                    15

( 2 ) INFORMATION FOR SEQ ID NO: 103:

( i ) SEQUENCE CHARACTERISTICS:

( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 103:

UUUGAGUCAG AUCAG  15

( 2 ) INFORMATION FOR SEQ ID NO: 104:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 104:

GUCAGAUCAG CUCCU  15

( 2 ) INFORMATION FOR SEQ ID NO: 105:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 105:

AUCAGCUCCU AAGGU  15

( 2 ) INFORMATION FOR SEQ ID NO: 106:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 106:

AGCUCCUAAG GUGCU  15

( 2 ) INFORMATION FOR SEQ ID NO: 107:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 107:

CAGUGCUCCC AAGAG  15

( 2 ) INFORMATION FOR SEQ ID NO: 108:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 108:

CCAGGCUCCU GUUCG  15

( 2 ) INFORMATION FOR SEQ ID NO: 109:

( i ) SEQUENCE CHARACTERISTICS:
( A ) LENGTH: 15 base pairs
( B ) TYPE: nucleic acid (C) STRANDEDNESS: single
(D) TOPOLOGY: linear (xi) SEQUENCE DESCRIPTION: SEQ ID NO: 109:

AAGCCAUUAG CCAGC                                                                                   15

(2) INFORMATION FOR SEQ ID NO: 110:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 110:

UUUGAGUCAG AUCAG                                                                                   15

(2) INFORMATION FOR SEQ ID NO: 111:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 111:

AGCGAAUCCA GACCA                                                                                   15

(2) INFORMATION FOR SEQ ID NO: 112:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 112:

AACCCCUUUC ACGUU                                                                                   15

(2) INFORMATION FOR SEQ ID NO: 113:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 113:

ACCCCUUUCA CGUUC                                                                                   15

(2) INFORMATION FOR SEQ ID NO: 114:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 114:

UUCACGUUCC UAUAG                                                                                   15

(2) INFORMATION FOR SEQ ID NO: 115:

(i) SEQUENCE CHARACTERISTICS:
    (A) LENGTH: 15 base pairs
    (B) TYPE: nucleic acid
    (C) STRANDEDNESS: single
    (D) TOPOLOGY: linear ( x i ) SEQUENCE DESCRIPTION: SEQ ID NO: 115:

UCACGUUCCU AUAGA                                                                                15

( 2 ) INFORMATION FOR SEQ ID NO: 116:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 116:

CGUUCCUAUA GAGGA                                                                                15

( 2 ) INFORMATION FOR SEQ ID NO: 117:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 117:

UUCCUAUAGA GGAGC                                                                                15

( 2 ) INFORMATION FOR SEQ ID NO: 118:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 118:

GGGGACUAUG ACUUG                                                                                15

( 2 ) INFORMATION FOR SEQ ID NO: 119:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 119:

UGCGCCUCUG CUUCC                                                                                15

( 2 ) INFORMATION FOR SEQ ID NO: 120:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 120:

CUCUGCUUCC AGGUG                                                                                15

( 2 ) INFORMATION FOR SEQ ID NO: 121:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 121:

UCUGCUUCCA GGUGA 15

( 2 ) INFORMATION FOR SEQ ID NO: 122:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 122:

AAGCCAUUAG CCAGC 15

( 2 ) INFORMATION FOR SEQ ID NO: 123:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 123:

GGCCCUCCU CCUGA 15

( 2 ) INFORMATION FOR SEQ ID NO: 124:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 124:

CCCCUGUCCU CUCAC 15

( 2 ) INFORMATION FOR SEQ ID NO: 125:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 125:

CUGUCCUCUC ACAUC 15

( 2 ) INFORMATION FOR SEQ ID NO: 126:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 126:

GUCCCUUCCU CAGCC 15

( 2 ) INFORMATION FOR SEQ ID NO: 127:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 127:

CCUUCCUCAG CCAUG 15

5,658,780

73

74

-continued ( 2 ) INFORMATION FOR SEQ ID NO: 128:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 128:

UCCUGCUUCC AUCUC                                               15

( 2 ) INFORMATION FOR SEQ ID NO: 129:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 129:

AUCCGAUUUU UGAUA                                              15

( 2 ) INFORMATION FOR SEQ ID NO: 130:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 130:

CCGAUUUUUG AUAAC                                              15

( 2 ) INFORMATION FOR SEQ ID NO: 131:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 131:

CGAUUUUUGA UAACC                                              15

( 2 ) INFORMATION FOR SEQ ID NO: 132:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 132:

UGGCCAUUGU GUUCC                                              15

( 2 ) INFORMATION FOR SEQ ID NO: 133:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 133:

CCGAGCUCAA GAUCU                                              15

( 2 ) INFORMATION FOR SEQ ID NO: 134:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 134:

UCAAGAUCUG CCGAG     15

( 2 ) INFORMATION FOR SEQ ID NO: 135:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 135:

CGGAACUCUG GGAGC     15

( 2 ) INFORMATION FOR SEQ ID NO: 136:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 136:

GCUGCCUCGG UGGGG     15

( 2 ) INFORMATION FOR SEQ ID NO: 137:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 137:

AUGAGAUCUU CUUGC     15

( 2 ) INFORMATION FOR SEQ ID NO: 138:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 138:

GAGAUCUUCU UGCUG     15

( 2 ) INFORMATION FOR SEQ ID NO: 139:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 139:

AGAUCUUCUU GCUGU     15

( 2 ) INFORMATION FOR SEQ ID NO: 140:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 140:

UUCUCCUCCA UUGCG    15

( 2 ) INFORMATION FOR SEQ ID NO: 141:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 141:

AAGACAUUGA GGUGU    15

( 2 ) INFORMATION FOR SEQ ID NO: 142:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 142:

GAGGUGUAUU UCACG    15

( 2 ) INFORMATION FOR SEQ ID NO: 143:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 143:

GGUGUAUUUC ACGGG    15

( 2 ) INFORMATION FOR SEQ ID NO: 144:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 144:

GUGUAUUUCA CGGGA    15

( 2 ) INFORMATION FOR SEQ ID NO: 145:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 145:

UGUAUUUCAC GGGAC    15

( 2 ) INFORMATION FOR SEQ ID NO: 146:

( i ) SEQUENCE CHARACTERISTICS:
  ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO: 146:

CGAGGCUCCU UUUCU 15

(2) INFORMATION FOR SEQ ID NO: 147:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 147:

GAUGAGUUUU CCCCC 15

(2) INFORMATION FOR SEQ ID NO: 148:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 148:

AUGAGUUUUC CCCCA 15

(2) INFORMATION FOR SEQ ID NO: 149:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 149:

UGAGUUUUCC CCCAU 15

(2) INFORMATION FOR SEQ ID NO: 150:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 150:

AUGCUGUUAC CAUCA 15

(2) INFORMATION FOR SEQ ID NO: 151:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 151:

UGCUGUUACC AUCAG 15

(2) INFORMATION FOR SEQ ID NO: 152:

(i) SEQUENCE CHARACTERISTICS:
(A) LENGTH: 15 base pairs
(B) TYPE: nucleic acid
(C) STRANDEDNESS: single (D) TOPOLOGY: linear (xi) SEQUENCE DESCRIPTION: SEQ ID NO: 152:

GGCCCCUCCU CCUGA                                                                                    15

(2) INFORMATION FOR SEQ ID NO: 153:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 153:

GUCCCUUCCU CAGCC                                                                                    15

(2) INFORMATION FOR SEQ ID NO: 154:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 154:

UUACCAUCAG GGCAG                                                                                    15

(2) INFORMATION FOR SEQ ID NO: 155:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 155:

GGGAGUUUAG UCUGA                                                                                    15

(2) INFORMATION FOR SEQ ID NO: 156:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 156:

CAGCCCUACA CCUUC                                                                                    15

(2) INFORMATION FOR SEQ ID NO: 157:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 157:

CUGGCCUUAG CACCG                                                                                    15

(2) INFORMATION FOR SEQ ID NO: 158:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( x i ) SEQUENCE DESCRIPTION: SEQ ID NO: 158:

GGUCCCUUCC UCAGC     15

( 2 ) INFORMATION FOR SEQ ID NO: 159:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 159:

CCCAGCUCCU GCCCC     15

( 2 ) INFORMATION FOR SEQ ID NO: 160:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 160:

CCAGCCUCCA GGCUC     15

( 2 ) INFORMATION FOR SEQ ID NO: 161:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 161:

CCCAGCUCCU GCCCC     15

( 2 ) INFORMATION FOR SEQ ID NO: 162:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 162:

CCAUGGUCCC UUCCU     15

( 2 ) INFORMATION FOR SEQ ID NO: 163:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 163:

GUGGGCUCAG CUGCG     15

( 2 ) INFORMATION FOR SEQ ID NO: 164:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 164:

AUGAGUUUUC CCCCA                                                               15

(2) INFORMATION FOR SEQ ID NO: 165:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 165:

CUCCUGUUCG AGUCU                                                               15

(2) INFORMATION FOR SEQ ID NO: 166:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 166:

CCCCAGUUCU AACCC                                                               15

(2) INFORMATION FOR SEQ ID NO: 167:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 167:

CAGUUCUAAC CCCGG                                                               15

(2) INFORMATION FOR SEQ ID NO: 168:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 168:

GGGUCCUCCC CAGUC                                                               15

(2) INFORMATION FOR SEQ ID NO: 169:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 169:

CUUUUCUCAA GCUGA                                                               15

(2) INFORMATION FOR SEQ ID NO: 170:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 170:

ACGCUGUCGG AAGCC                                                               15

( 2 ) INFORMATION FOR SEQ ID NO: 171:

( i ) SEQUENCE CHARACTERISTICS:
　　　　　　　　( A ) LENGTH: 15 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO: 171:

CUGCAGUUUG  AUGCU　　　　　　　　　　　　　　　　　　　　　　　　　　　　　15

( 2 ) INFORMATION FOR SEQ ID NO: 172:

( i ) SEQUENCE CHARACTERISTICS:
　　　　　　　　( A ) LENGTH: 15 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO: 172:

UGCAGUUUGA  UGCUG　　　　　　　　　　　　　　　　　　　　　　　　　　　　　15

( 2 ) INFORMATION FOR SEQ ID NO: 173:

( i ) SEQUENCE CHARACTERISTICS:
　　　　　　　　( A ) LENGTH: 15 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO: 173:

GGGGCCUUGC  UUGGC　　　　　　　　　　　　　　　　　　　　　　　　　　　　　15

( 2 ) INFORMATION FOR SEQ ID NO: 174:

( i ) SEQUENCE CHARACTERISTICS:
　　　　　　　　( A ) LENGTH: 15 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO: 174:

CCUUGCUUGG  CAACA　　　　　　　　　　　　　　　　　　　　　　　　　　　　　15

( 2 ) INFORMATION FOR SEQ ID NO: 175:

( i ) SEQUENCE CHARACTERISTICS:
　　　　　　　　( A ) LENGTH: 15 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO: 175:

GGAGUGUUCA  CAGAC　　　　　　　　　　　　　　　　　　　　　　　　　　　　　15

( 2 ) INFORMATION FOR SEQ ID NO: 176:

( i ) SEQUENCE CHARACTERISTICS:
　　　　　　　　( A ) LENGTH: 15 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO: 176:

GAGUGUUCAC  AGACC　　　　　　　　　　　　　　　　　　　　　　　　　　　　　15

( 2 ) INFORMATION FOR SEQ ID NO: 177:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 177:

CUGGCAUCUG UGGAC      15

( 2 ) INFORMATION FOR SEQ ID NO: 178:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 178:

CUUCGGUAGG GAACU      15

( 2 ) INFORMATION FOR SEQ ID NO: 179:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 179:

GACAACUCAG AGUUU      15

( 2 ) INFORMATION FOR SEQ ID NO: 180:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 180:

UCAGAGUUUC AGCAG      15

( 2 ) INFORMATION FOR SEQ ID NO: 181:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 181:

CAGAGUUUCA GCAGC      15

( 2 ) INFORMATION FOR SEQ ID NO: 182:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 182:

AGAGUUUCAG CAGCU      15

( 2 ) INFORMATION FOR SEQ ID NO: 183:

( i ) SEQUENCE CHARACTERISTICS:

( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 183:

GGUGCAUCCC UGUGU 15

( 2 ) INFORMATION FOR SEQ ID NO: 184:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 184:

AUGGAGUACC CUGAA 15

( 2 ) INFORMATION FOR SEQ ID NO: 185:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 185:

UGAAGCUAUA ACUCG 15

( 2 ) INFORMATION FOR SEQ ID NO: 186:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 186:

AAGCUAUAAC UCGCC 15

( 2 ) INFORMATION FOR SEQ ID NO: 187:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 187:

UAUAACUCGC CUGGU 15

( 2 ) INFORMATION FOR SEQ ID NO: 188:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 188:

CUCUCCUAGA GAGGG 15

( 2 ) INFORMATION FOR SEQ ID NO: 189:

( i ) SEQUENCE CHARACTERISTICS:
( A ) LENGTH: 15 base pairs
( B ) TYPE: nucleic acid (C) STRANDEDNESS: single
(D) TOPOLOGY: linear (xi) SEQUENCE DESCRIPTION: SEQ ID NO: 189:

CCCAGCUCCU GCCCC                                                                15

(2) INFORMATION FOR SEQ ID NO: 190:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO: 190:

UCCUGCUUCG GUAGG                                                                15

(2) INFORMATION FOR SEQ ID NO: 191:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO: 191:

CGGGGCUUCC CAAUG                                                                15

(2) INFORMATION FOR SEQ ID NO: 192:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO: 192:

CUGACCUCUG CCCAG                                                                15

(2) INFORMATION FOR SEQ ID NO: 193:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO: 193:

CUCUGCUUCC AGGUG                                                                15

(2) INFORMATION FOR SEQ ID NO: 194:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO: 194:

UCUGCUUCCA GGUGA                                                                15

(2) INFORMATION FOR SEQ ID NO: 195:

(i) SEQUENCE CHARACTERISTICS:
  (A) LENGTH: 15 base pairs
  (B) TYPE: nucleic acid
  (C) STRANDEDNESS: single
  (D) TOPOLOGY: linear ( x i ) SEQUENCE DESCRIPTION: SEQ ID NO: 195:

CUCGCUUUCG GAGGU　　　　　　　　　　　　　　　　　　　　　　　　　　　15

( 2 ) INFORMATION FOR SEQ ID NO: 196:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 196:

AAUGGCUCGU CUGUA　　　　　　　　　　　　　　　　　　　　　　　　　　　15

( 2 ) INFORMATION FOR SEQ ID NO: 197:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 197:

GGCUCGUCUG UAGUG　　　　　　　　　　　　　　　　　　　　　　　　　　　15

( 2 ) INFORMATION FOR SEQ ID NO: 198:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 198:

CGUCUGUAGU GCACG　　　　　　　　　　　　　　　　　　　　　　　　　　　15

( 2 ) INFORMATION FOR SEQ ID NO: 199:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 199:

GAACUGUUCC CCCUC　　　　　　　　　　　　　　　　　　　　　　　　　　　15

( 2 ) INFORMATION FOR SEQ ID NO: 200:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 200:

AACUGUUCCC CCUCA　　　　　　　　　　　　　　　　　　　　　　　　　　　15

( 2 ) INFORMATION FOR SEQ ID NO: 201:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 201:

UCCCCCUCAU CUUCC  15

(2) INFORMATION FOR SEQ ID NO: 202:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 202:

CCCUCAUCUU CCCGG  15

(2) INFORMATION FOR SEQ ID NO: 203:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 203:

CUCAUCUUCC CGGCA  15

(2) INFORMATION FOR SEQ ID NO: 204:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 204:

UCAUCUUCCC GGCAG  15

(2) INFORMATION FOR SEQ ID NO: 205:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 205:

CAGGCCUCUG GCCCC  15

(2) INFORMATION FOR SEQ ID NO: 206:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 206:

GGCCCCUAUG UGGAG  15

(2) INFORMATION FOR SEQ ID NO: 207:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 207:

UGGAGAUCAU UGAGC  15

(2) INFORMATION FOR SEQ ID NO: 208:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 208:

AGAUCAUUGA GCAGC     15

(2) INFORMATION FOR SEQ ID NO: 209:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 209:

AUGCGCUUCC GCUAC     15

(2) INFORMATION FOR SEQ ID NO: 210:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 210:

UGCGCUUCCG CUACA     15

(2) INFORMATION FOR SEQ ID NO: 211:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 211:

UUCCGCUACA AGUGC     15

(2) INFORMATION FOR SEQ ID NO: 212:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 212:

GGGCGCUCCG CGGGC     15

(2) INFORMATION FOR SEQ ID NO: 213:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 213:

GCAGCAUCCC AGGCG     15

( 2 ) INFORMATION FOR SEQ ID NO: 214:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 214:

CACAGAUACC ACCAA     15

( 2 ) INFORMATION FOR SEQ ID NO: 215:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 215:

CCACCAUCAA GAUCA     15

( 2 ) INFORMATION FOR SEQ ID NO: 216:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 216:

UCAAGAUCAA UGGCU     15

( 2 ) INFORMATION FOR SEQ ID NO: 217:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 217:

AAUGGCUACA CAGGA     15

( 2 ) INFORMATION FOR SEQ ID NO: 218:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 218:

UGCGCAUCUC CCUGG     15

( 2 ) INFORMATION FOR SEQ ID NO: 219:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 219:

CGCAUCUCCC UGGUC     15

( 2 ) INFORMATION FOR SEQ ID NO: 220:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 220:

CCCUGGUCAC CAAGG                                                             15

( 2 ) INFORMATION FOR SEQ ID NO: 221:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 221:

GGACCCUCCU CACCG                                                             15

( 2 ) INFORMATION FOR SEQ ID NO: 222:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 222:

CCCUCCUCAC CGGCC                                                             15

( 2 ) INFORMATION FOR SEQ ID NO: 223:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 223:

CCGGCCUCAC CCCCA                                                             15

( 2 ) INFORMATION FOR SEQ ID NO: 224:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 224:

ACGAGCUUGU AGGAA                                                             15

( 2 ) INFORMATION FOR SEQ ID NO: 225:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 225:

AGCUUGUAGG AAAGG                                                             15

( 2 ) INFORMATION FOR SEQ ID NO: 226:

( i ) SEQUENCE CHARACTERISTICS:
        ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO: 226:

GAUGGCUUCU AUGAG                                                                                      15

(2) INFORMATION FOR SEQ ID NO: 227:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 227:

AUGGCUUCUA UGAGG                                                                                      15

(2) INFORMATION FOR SEQ ID NO: 228:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 228:

GGCUUCUAUG AGGCU                                                                                      15

(2) INFORMATION FOR SEQ ID NO: 229:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 229:

CUGAGCUCUG CCCGG                                                                                      15

(2) INFORMATION FOR SEQ ID NO: 230:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 230:

GCUGCAUCCA CAGUU                                                                                      15

(2) INFORMATION FOR SEQ ID NO: 231:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 231:

CCACAGUUUC CAGAA                                                                                      15

(2) INFORMATION FOR SEQ ID NO: 232:

(i) SEQUENCE CHARACTERISTICS:
(A) LENGTH: 15 base pairs
(B) TYPE: nucleic acid
(C) STRANDEDNESS: single (D) TOPOLOGY: linear (xi) SEQUENCE DESCRIPTION: SEQ ID NO: 232:

CACAGUUUCC AGAAC 15

(2) INFORMATION FOR SEQ ID NO: 233:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 233:

ACAGUUUCCA GAACC 15

(2) INFORMATION FOR SEQ ID NO: 234:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 234:

UGGGAAUCCA GUGUG 15

(2) INFORMATION FOR SEQ ID NO: 235:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 235:

GGCUCCUUUU CGCAA 15

(2) INFORMATION FOR SEQ ID NO: 236:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 236:

GCUCCUUUUC GCAAG 15

(2) INFORMATION FOR SEQ ID NO: 237:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 237:

CUCCUUUUCG CAAGC 15

(2) INFORMATION FOR SEQ ID NO: 238:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( x i ) SEQUENCE DESCRIPTION: SEQ ID NO: 238:

UCCUUUUCGC AAGCU                                                                                  15

( 2 ) INFORMATION FOR SEQ ID NO: 239:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 239:

UGGCCAUUGU GUUCC                                                                                  15

( 2 ) INFORMATION FOR SEQ ID NO: 240:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 240:

AUUGUGUUCC GGACC                                                                                  15

( 2 ) INFORMATION FOR SEQ ID NO: 241:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 241:

UUGUGUUCCG GACCC                                                                                  15

( 2 ) INFORMATION FOR SEQ ID NO: 242:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 242:

GACCCCUCCC UACGC                                                                                  15

( 2 ) INFORMATION FOR SEQ ID NO: 243:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 243:

CCUCCCUACG CAGAC                                                                                  15

( 2 ) INFORMATION FOR SEQ ID NO: 244:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 244:

GCAGGCUCCU GUGCG 15

( 2 ) INFORMATION FOR SEQ ID NO: 245:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( x i ) SEQUENCE DESCRIPTION: SEQ ID NO: 245:

UGCGUGUCUC CAUGC 15

( 2 ) INFORMATION FOR SEQ ID NO: 246:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( x i ) SEQUENCE DESCRIPTION: SEQ ID NO: 246:

CGUGUCUCCA UGCAG 15

( 2 ) INFORMATION FOR SEQ ID NO: 247:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( x i ) SEQUENCE DESCRIPTION: SEQ ID NO: 247:

GCGGCCUUCC GACCG 15

( 2 ) INFORMATION FOR SEQ ID NO: 248:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( x i ) SEQUENCE DESCRIPTION: SEQ ID NO: 248:

CGGCCUUCCG ACCGG 15

( 2 ) INFORMATION FOR SEQ ID NO: 249:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( x i ) SEQUENCE DESCRIPTION: SEQ ID NO: 249:

GGGAGCUCAG UGAGC 15

( 2 ) INFORMATION FOR SEQ ID NO: 250:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( x i ) SEQUENCE DESCRIPTION: SEQ ID NO: 250:

AUGGAAUUCC AGUAC 15

( 2 ) INFORMATION FOR SEQ ID NO: 251:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 251:

UGGAAUUCCA GUACC                                  15

( 2 ) INFORMATION FOR SEQ ID NO: 252:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 252:

UUCCAGUACC UGCCA                                  15

( 2 ) INFORMATION FOR SEQ ID NO: 253:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 253:

GCCAGAUACA GACGA                                  15

( 2 ) INFORMATION FOR SEQ ID NO: 254:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 254:

AGACGAUCGU CACCG                                  15

( 2 ) INFORMATION FOR SEQ ID NO: 255:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 255:

CGAUCGUCAC CGGAU                                  15

( 2 ) INFORMATION FOR SEQ ID NO: 256:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 256:

ACCGGAUUGA GGAGA                                  15

( 2 ) INFORMATION FOR SEQ ID NO: 257:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 257:

GAAACGUAAA AGGAC                 15

( 2 ) INFORMATION FOR SEQ ID NO: 258:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 258:

AGGACAUAUG AGACC                 15

( 2 ) INFORMATION FOR SEQ ID NO: 259:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 259:

GAGACCUUCA AGAGC                 15

( 2 ) INFORMATION FOR SEQ ID NO: 260:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 260:

AGACCUUCAA GAGCA                 15

( 2 ) INFORMATION FOR SEQ ID NO: 261:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 261:

AGAGCAUCAU GAAGA                 15

( 2 ) INFORMATION FOR SEQ ID NO: 262:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 262:

GAAGAGUCCU UUCAG                 15

( 2 ) INFORMATION FOR SEQ ID NO: 263:

( i ) SEQUENCE CHARACTERISTICS:

( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 263:

GAGUCCUUUC AGCGG                                                                                15

( 2 ) INFORMATION FOR SEQ ID NO: 264:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 264:

AGUCCUUUCA GCGGA                                                                                15

( 2 ) INFORMATION FOR SEQ ID NO: 265:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 265:

GUCCUUUCAG CGGAC                                                                                15

( 2 ) INFORMATION FOR SEQ ID NO: 266:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 266:

CCGGCCUCCA CCUCG                                                                                15

( 2 ) INFORMATION FOR SEQ ID NO: 267:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 267:

UCCACCUCGA CGCAU                                                                                15

( 2 ) INFORMATION FOR SEQ ID NO: 268:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 268:

GACGCAUUGC UGUGC                                                                                15

( 2 ) INFORMATION FOR SEQ ID NO: 269:

( i ) SEQUENCE CHARACTERISTICS:
                ( A ) LENGTH: 15 base pairs
                ( B ) TYPE: nucleic acid ( C ) STRANDEDNESS: single
( D ) TOPOLOGY: linear ( x i ) SEQUENCE DESCRIPTION: SEQ ID NO: 269:

UGUGCCUUCC CGCAG 15

( 2 ) INFORMATION FOR SEQ ID NO: 270:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 270:

GUGCCUUCCC GCAGC 15

( 2 ) INFORMATION FOR SEQ ID NO: 271:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 271:

CGCAGCUCAG CUUCU 15

( 2 ) INFORMATION FOR SEQ ID NO: 272:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 272:

CUCAGCUUCU GUCCC 15

( 2 ) INFORMATION FOR SEQ ID NO: 273:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 273:

UCAGCUUCUG UCCCC 15

( 2 ) INFORMATION FOR SEQ ID NO: 274:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 274:

CUUCUGUCCC CAAGC 15

( 2 ) INFORMATION FOR SEQ ID NO: 275:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 275:

CAGCCCUAUC CCUUU                                                        15

( 2 ) INFORMATION FOR SEQ ID NO: 276:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 276:

GCCCUAUCCC UUUAC                                                        15

( 2 ) INFORMATION FOR SEQ ID NO: 277:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 277:

UAUCCCUUUA CGUCA                                                        15

( 2 ) INFORMATION FOR SEQ ID NO: 278:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 278:

AUCCCUUUAC GUCAU                                                        15

( 2 ) INFORMATION FOR SEQ ID NO: 279:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 279:

UCCCUUUACG UCAUC                                                        15

( 2 ) INFORMATION FOR SEQ ID NO: 280:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 280:

UUUACGUCAU CCCUG                                                        15

( 2 ) INFORMATION FOR SEQ ID NO: 281:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 281:

ACGUCAUCCC UGAGC                                                                                        15

(2) INFORMATION FOR SEQ ID NO: 282:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 282:

GCACCAUCAA CUAUG                                                                                        15

(2) INFORMATION FOR SEQ ID NO: 283:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 283:

AUCAACUAUG AUGAG                                                                                        15

(2) INFORMATION FOR SEQ ID NO: 284:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 284:

GAAGACUUCU CCUCC                                                                                        15

(2) INFORMATION FOR SEQ ID NO: 285:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 285:

AAGACUUCUC CUCCA                                                                                        15

(2) INFORMATION FOR SEQ ID NO: 286:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 286:

GACUUCUCCU CCAUU                                                                                        15

(2) INFORMATION FOR SEQ ID NO: 287:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 287:

UUCUCCUCCA UUGCG                                                                                        15

( 2 ) INFORMATION FOR SEQ ID NO: 288:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 288:

CCUCCAUUGC GGACA 15

( 2 ) INFORMATION FOR SEQ ID NO: 289:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 289:

AUGGACUUCU CAGCC 15

( 2 ) INFORMATION FOR SEQ ID NO: 290:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 290:

UGGACUUCUC AGCCC 15

( 2 ) INFORMATION FOR SEQ ID NO: 291:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 291:

GACUUCUCAG CCCUG 15

( 2 ) INFORMATION FOR SEQ ID NO: 292:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 292:

GCUGAGUCAG AUCAG 15

( 2 ) INFORMATION FOR SEQ ID NO: 293:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 293:

GUCAGAUCAG CUCCU 15

( 2 ) INFORMATION FOR SEQ ID NO: 294:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 294:

AUCAGCUCCU AAGGG         15

( 2 ) INFORMATION FOR SEQ ID NO: 295:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 295:

AGCUCCUAAG GGGGU         15

( 2 ) INFORMATION FOR SEQ ID NO: 296:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 296:

CUGCCCUCCC CAGAG         15

( 2 ) INFORMATION FOR SEQ ID NO: 297:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 297:

GCAGGCUAUC AGUCA         15

( 2 ) INFORMATION FOR SEQ ID NO: 298:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 298:

AGGCUAUCAG UCAGC         15

( 2 ) INFORMATION FOR SEQ ID NO: 299:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 299:

UAUCAGUCAG CGCAU         15

( 2 ) INFORMATION FOR SEQ ID NO: 300:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 300:

AGCGCAUCCA GACCA 15

( 2 ) INFORMATION FOR SEQ ID NO: 301:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 301:

AACCCCUUCC AAGUU 15

( 2 ) INFORMATION FOR SEQ ID NO: 302:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 302:

ACCCCUUCCA AGUUC 15

( 2 ) INFORMATION FOR SEQ ID NO: 303:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 303:

UCCAAGUUCC UAUAG 15

( 2 ) INFORMATION FOR SEQ ID NO: 304:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 304:

CCAAGUUCCU AUAGA 15

( 2 ) INFORMATION FOR SEQ ID NO: 305:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 305:

AGUUCCUAUA GAAGA 15

( 2 ) INFORMATION FOR SEQ ID NO: 306:

( i ) SEQUENCE CHARACTERISTICS:
  ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO: 306:

UUCCUAUAGA AGAGC 15

(2) INFORMATION FOR SEQ ID NO: 307:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 307:

GGGGACUACG ACCUG 15

(2) INFORMATION FOR SEQ ID NO: 308:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 308:

UGCGGCUCUG CUUCC 15

(2) INFORMATION FOR SEQ ID NO: 309:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 309:

CUCUGCUUCC AGGUG 15

(2) INFORMATION FOR SEQ ID NO: 310:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 310:

UCUGCUUCCA GGUGA 15

(2) INFORMATION FOR SEQ ID NO: 311:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 311:

GACCCAUCAG GCAGG 15

(2) INFORMATION FOR SEQ ID NO: 312:

(i) SEQUENCE CHARACTERISTICS:
(A) LENGTH: 15 base pairs
(B) TYPE: nucleic acid
(C) STRANDEDNESS: single ( D ) TOPOLOGY: linear ( x i ) SEQUENCE DESCRIPTION: SEQ ID NO: 312:

GGCCCCUCCG CCUGC 15

( 2 ) INFORMATION FOR SEQ ID NO: 313:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 313:

CGCCUGUCCU UCCUC 15

( 2 ) INFORMATION FOR SEQ ID NO: 314:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 314:

CUGUCCUUCC UCAUC 15

( 2 ) INFORMATION FOR SEQ ID NO: 315:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 315:

UGUCCUUCCU CAUCC 15

( 2 ) INFORMATION FOR SEQ ID NO: 316:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 316:

CCUUCCUCAU CCCAU 15

( 2 ) INFORMATION FOR SEQ ID NO: 317:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 317:

UCCUCAUCCC AUCUU 15

( 2 ) INFORMATION FOR SEQ ID NO: 318:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 318:

AUCCCAUCUU UGACA 15

( 2 ) INFORMATION FOR SEQ ID NO: 319:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 319:

CCCAUCUUUG ACAAU 15

( 2 ) INFORMATION FOR SEQ ID NO: 320:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 320:

CCAUCUUUGA CAAUC 15

( 2 ) INFORMATION FOR SEQ ID NO: 321:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 321:

UGACAAUCGU GCCCC 15

( 2 ) INFORMATION FOR SEQ ID NO: 322:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 322:

CCGAGCUCAA GAUCU 15

( 2 ) INFORMATION FOR SEQ ID NO: 323:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 323:

UCAAGAUCUG CCGAG 15

( 2 ) INFORMATION FOR SEQ ID NO: 324:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 324:

CGAAACUCUG GCAGC                                                     15

( 2 ) INFORMATION FOR SEQ ID NO: 325:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 325:

GCUGCCUCGG UGGGG                                                     15

( 2 ) INFORMATION FOR SEQ ID NO: 326:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 326:

AUGAGAUCUU CCUAC                                                     15

( 2 ) INFORMATION FOR SEQ ID NO: 327:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 327:

GAGAUCUUCC UACUG                                                     15

( 2 ) INFORMATION FOR SEQ ID NO: 328:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 328:

AGAUCUUCCU ACUGU                                                     15

( 2 ) INFORMATION FOR SEQ ID NO: 329:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 329:

UCUUCCUACU GUGUG                                                     15

( 2 ) INFORMATION FOR SEQ ID NO: 330:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 330:

AGGACAUUGA GGUGU                                                     15

( 2 ) INFORMATION FOR SEQ ID NO: 331:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 331:

GAGGUGUAUU UCACG     15

( 2 ) INFORMATION FOR SEQ ID NO: 332:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 332:

GGUGUAUUUC ACGGG     15

( 2 ) INFORMATION FOR SEQ ID NO: 333:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 333:

GUGUAUUUCA CGGGA     15

( 2 ) INFORMATION FOR SEQ ID NO: 334:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 334:

UGUAUUUCAC GGGAC     15

( 2 ) INFORMATION FOR SEQ ID NO: 335:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 335:

CGAGGCUCCU UUUCG     15

( 2 ) INFORMATION FOR SEQ ID NO: 336:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 336:

GAUGAGUUUC CCACC     15

( 2 ) INFORMATION FOR SEQ ID NO: 337:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 337:

AUGAGUUUCC CACCA                                                                                                15

( 2 ) INFORMATION FOR SEQ ID NO: 338:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 338:

UGAGUUUCCC ACCAU                                                                                                15

( 2 ) INFORMATION FOR SEQ ID NO: 339:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 339:

AUGGUGUUUC CUUCU                                                                                                15

( 2 ) INFORMATION FOR SEQ ID NO: 340:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 340:

UGGUGUUUCC UUCUG                                                                                                15

( 2 ) INFORMATION FOR SEQ ID NO: 341:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 341:

GGUGUUUCCU UCUGG                                                                                                15

( 2 ) INFORMATION FOR SEQ ID NO: 342:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 342:

GUUUCCUUCU GGGCA                                                                                                15

( 2 ) INFORMATION FOR SEQ ID NO: 343:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 343:

UUUCCUUCUG GGCAG 15

(2) INFORMATION FOR SEQ ID NO: 344:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 344:

GGCAGAUCAG CCAGG 15

(2) INFORMATION FOR SEQ ID NO: 345:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 345:

CAGGCCUCGG CCUUG 15

(2) INFORMATION FOR SEQ ID NO: 346:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 346:

UCGGCCUUGG CCCCG 15

(2) INFORMATION FOR SEQ ID NO: 347:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 347:

GGCCCUCCC CAAGU 15

(2) INFORMATION FOR SEQ ID NO: 348:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 348:

CCCAAGUCCU GCCCC 15

(2) INFORMATION FOR SEQ ID NO: 349:

(i) SEQUENCE CHARACTERISTICS:
(A) LENGTH: 15 base pairs
(B) TYPE: nucleic acid ( C ) STRANDEDNESS: single
( D ) TOPOLOGY: linear ( x i ) SEQUENCE DESCRIPTION: SEQ ID NO: 349:

CCAGGCUCCA GCCCC                                                                                                    15

( 2 ) INFORMATION FOR SEQ ID NO: 350:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 350:

CCCUGCUCCA GCCAU                                                                                                    15

( 2 ) INFORMATION FOR SEQ ID NO: 351:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 351:

CCAUGGUAUC AGCUC                                                                                                    15

( 2 ) INFORMATION FOR SEQ ID NO: 352:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 352:

AUGGUAUCAG CUCUG                                                                                                    15

( 2 ) INFORMATION FOR SEQ ID NO: 353:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 353:

AUCAGCUCUG GCCCA                                                                                                    15

( 2 ) INFORMATION FOR SEQ ID NO: 354:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 354:

CCCCUGUCCC AGUCC                                                                                                    15

( 2 ) INFORMATION FOR SEQ ID NO: 355:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 355:

UCCCAGUCCU AGCCC    15

( 2 ) INFORMATION FOR SEQ ID NO: 356:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 356:

CAGUCCUAGC CCCAG    15

( 2 ) INFORMATION FOR SEQ ID NO: 357:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 357:

AGGCCCUCCU CAGGC    15

( 2 ) INFORMATION FOR SEQ ID NO: 358:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 358:

CCCUCCUCAG GCUGU    15

( 2 ) INFORMATION FOR SEQ ID NO: 359:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 359:

ACGCUGUCAG AGGCC    15

( 2 ) INFORMATION FOR SEQ ID NO: 360:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 360:

CUGCAGUUUG AUGAU    15

( 2 ) INFORMATION FOR SEQ ID NO: 361:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 361:

UGCAGUUUGA UGAUG                                                                         15

( 2 ) INFORMATION FOR SEQ ID NO: 362:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 362:

GGGGCCUUGC UUGGC                                                                         15

( 2 ) INFORMATION FOR SEQ ID NO: 363:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 363:

CCUUGCUUGG CAACA                                                                         15

( 2 ) INFORMATION FOR SEQ ID NO: 364:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 364:

GCUGUGUUCA CAGAC                                                                         15

( 2 ) INFORMATION FOR SEQ ID NO: 365:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 365:

CUGUGUUCAC AGACC                                                                         15

( 2 ) INFORMATION FOR SEQ ID NO: 366:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 366:

CUGGCAUCCG UCGAC                                                                         15

( 2 ) INFORMATION FOR SEQ ID NO: 367:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 367:

CAUCCGUCGA CAACU                                                                         15

( 2 ) INFORMATION FOR SEQ ID NO: 368:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 368:

GACAACUCCG AGUUU          15

( 2 ) INFORMATION FOR SEQ ID NO: 369:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 369:

UCCGAGUUUC AGCAG          15

( 2 ) INFORMATION FOR SEQ ID NO: 370:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 370:

CCGAGUUUCA GCAGC          15

( 2 ) INFORMATION FOR SEQ ID NO: 371:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 371:

CGAGUUUCAG CAGCU          15

( 2 ) INFORMATION FOR SEQ ID NO: 372:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 372:

AGGGCAUACC UGUGG          15

( 2 ) INFORMATION FOR SEQ ID NO: 373:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 373:

AUGGAGUACC CUGAG          15

( 2 ) INFORMATION FOR SEQ ID NO: 374:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 374:

UGAGGCUAUA ACUCG                    15

( 2 ) INFORMATION FOR SEQ ID NO: 375:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 375:

AGGCUAUAAC UCGCC                    15

( 2 ) INFORMATION FOR SEQ ID NO: 376:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 376:

UAUAACUCGC CUAGU                    15

( 2 ) INFORMATION FOR SEQ ID NO: 377:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 377:

CUCGCCUAGU GACAG                    15

( 2 ) INFORMATION FOR SEQ ID NO: 378:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 378:

CCCAGCUCCU GCUCC                    15

( 2 ) INFORMATION FOR SEQ ID NO: 379:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 379:

UCCUGCUCCA CUGGG                    15

( 2 ) INFORMATION FOR SEQ ID NO: 380:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 380:

CGGGGCUCCC CAAUG      15

( 2 ) INFORMATION FOR SEQ ID NO: 381:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 381:

AUGGCCUCCU UUCAG      15

( 2 ) INFORMATION FOR SEQ ID NO: 382:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 382:

GCCUCCUUUC AGGAG      15

( 2 ) INFORMATION FOR SEQ ID NO: 383:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 383:

CCUCCUUUCA GGAGA      15

( 2 ) INFORMATION FOR SEQ ID NO: 384:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 384:

CUCCUUUCAG GAGAU      15

( 2 ) INFORMATION FOR SEQ ID NO: 385:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 385:

UCCUGUGCUG AUGAGGCCGA AAGGCCGAAA GCCAUU      36

( 2 ) INFORMATION FOR SEQ ID NO: 386:

( i ) SEQUENCE CHARACTERISTICS:
  ( A ) LENGTH: 36 base pairs ( B ) TYPE: nucleic acid
( C ) STRANDEDNESS: single
( D ) TOPOLOGY: linear ( x i ) SEQUENCE DESCRIPTION: SEQ ID NO: 386:

CACCACGCUG AUGAGGCCGA AAGGCCGAAA GGAGCU                                    36

( 2 ) INFORMATION FOR SEQ ID NO: 387:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 387:

UGUCCGCCUG AUGAGGCCGA AAGGCCGAAA UGGAGG                                    36

( 2 ) INFORMATION FOR SEQ ID NO: 388:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 388:

GAGGGGACUG AUGAGGCCGA AAGGCCGAAA CAGAUC                                    36

( 2 ) INFORMATION FOR SEQ ID NO: 389:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 389:

UGAGGGGCUG AUGAGGCCGA AAGGCCGAAA ACAGAU                                    36

( 2 ) INFORMATION FOR SEQ ID NO: 390:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 390:

GAAAGAUCUG AUGAGGCCGA AAGGCCGAAA GGGGAA                                    36

( 2 ) INFORMATION FOR SEQ ID NO: 391:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 391:

AGGGAAACUG AUGAGGCCGA AAGGCCGAAA UGAGGG                                    36

( 2 ) INFORMATION FOR SEQ ID NO: 392:

( i ) SEQUENCE CHARACTERISTICS:
        ( A ) LENGTH: 36 base pairs
        ( B ) TYPE: nucleic acid
        ( C ) STRANDEDNESS: single ( D ) TOPOLOGY: linear ( x i ) SEQUENCE DESCRIPTION: SEQ ID NO: 392:

UGAGGGACUG AUGAGGCCGA AAGGCCGAAA GAUGAG    36

( 2 ) INFORMATION FOR SEQ ID NO: 393:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 393:

CUGAGGGCUG AUGAGGCCGA AAGGCCGAAA AGAUGA    36

( 2 ) INFORMATION FOR SEQ ID NO: 394:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 394:

AGGCCCACUG AUGAGGCCGA AAGGCCGAAA AGCCUG    36

( 2 ) INFORMATION FOR SEQ ID NO: 395:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 395:

CUCCACACUG AUGAGGCCGA AAGGCCGAAA AGGCCC    36

( 2 ) INFORMATION FOR SEQ ID NO: 396:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 396:

GUUCGAUCUG AUGAGGCCGA AAGGCCGAAA UCUCCA    36

( 2 ) INFORMATION FOR SEQ ID NO: 397:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 397:

GCUGUUCCUG AUGAGGCCGA AAGGCCGAAA UGAUCU    36

( 2 ) INFORMATION FOR SEQ ID NO: 398:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear (xi) SEQUENCE DESCRIPTION: SEQ ID NO: 398:

AUAGCGGCUG AUGAGGCCGA AAGGCCGAAA UCGCAU                                    36

(2) INFORMATION FOR SEQ ID NO: 399:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 399:

UAUAGCGCUG AUGAGGCCGA AAGGCCGAAA AUCGCA                                    36

(2) INFORMATION FOR SEQ ID NO: 400:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 400:

GCAUUUACUG AUGAGGCCGA AAGGCCGAAA GCGGAA                                    36

(2) INFORMATION FOR SEQ ID NO: 401:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 401:

GCCCGCUCUG AUGAGGCCGA AAGGCCGAAA GCGCCC                                    36

(2) INFORMATION FOR SEQ ID NO: 402:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 402:

CGCCAGGCUG AUGAGGCCGA AAGGCCGAAA UACUGC                                    36

(2) INFORMATION FOR SEQ ID NO: 403:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 403:

UUGGUGGCUG AUGAGGCCGA AAGGCCGAAA UCUGUG                                    36

(2) INFORMATION FOR SEQ ID NO: 404:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 404:

UGAUCUUCUG AUGAGGCCGA AAGGCCGAAA UGGUGG 36

( 2 ) INFORMATION FOR SEQ ID NO: 405:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 405:

AGCCAUUCUG AUGAGGCCGA AAGGCCGAAA UCUUGA 36

( 2 ) INFORMATION FOR SEQ ID NO: 406:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 406:

UCCUGUGCUG AUGAGGCCGA AAGGCCGAAA GCCAUU 36

( 2 ) INFORMATION FOR SEQ ID NO: 407:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 407:

CCAGGGACUG AUGAGGCCGA AAGGCCGAAA UUCGAA 36

( 2 ) INFORMATION FOR SEQ ID NO: 408:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 408:

GACCAGGCUG AUGAGGCCGA AAGGCCGAAA GAUUCG 36

( 2 ) INFORMATION FOR SEQ ID NO: 409:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 409:

CCUUGGUCUG AUGAGGCCGA AAGGCCGAAA CCAGGG 36

( 2 ) INFORMATION FOR SEQ ID NO: 410:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 410:

UCAGGAGCUG AUGAGGCCGA AAGGCCGAAA GGGGCC 36

( 2 ) INFORMATION FOR SEQ ID NO: 411:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 411:

GGCCGGUCUG AUGAGGCCGA AAGGCCGAAA GGUGGA    36

( 2 ) INFORMATION FOR SEQ ID NO: 412:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 412:

UGUGGAUCUG AUGAGGCCGA AAGGCCGAAA GGCCGG    36

( 2 ) INFORMATION FOR SEQ ID NO: 413:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 413:

UCCCCACCUG AUGAGGCCGA AAGGCCGAAA GUUCAU    36

( 2 ) INFORMATION FOR SEQ ID NO: 414:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 414:

GCUGUUCCUG AUGAGGCCGA AAGGCCGAAA UGAUCU    36

( 2 ) INFORMATION FOR SEQ ID NO: 415:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 415:

CUCAUAGCUG AUGAGGCCGA AAGGCCGAAA GCCAUC    36

( 2 ) INFORMATION FOR SEQ ID NO: 416:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 416:

CUCCGGACUG AUGAGGCCGA AAGGCCGAAA GACCAU    36

( 2 ) INFORMATION FOR SEQ ID NO: 417:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 417:

AGCCUCACUG AUGAGGCCGA AAGGCCGAAA GUAGCC    36

( 2 ) INFORMATION FOR SEQ ID NO: 418:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 418:

CUGGGCACUG AUGAGGCCGA AAGGCCGAAA GGUCAG    36

( 2 ) INFORMATION FOR SEQ ID NO: 419:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 419:

AGCUAUGCUG AUGAGGCCGA AAGGCCGAAA UACUGC    36

( 2 ) INFORMATION FOR SEQ ID NO: 420:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 420:

CUAUGGACUG AUGAGGCCGA AAGGCCGAAA CUGCGG    36

( 2 ) INFORMATION FOR SEQ ID NO: 421:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 421:

GUUCUGGCUG AUGAGGCCGA AAGGCCGAAA GCUAUG    36

( 2 ) INFORMATION FOR SEQ ID NO: 422:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 422:

GGUUCUGCUG AUGAGGCCGA AAGGCCGAAA AGCUAU    36

( 2 ) INFORMATION FOR SEQ ID NO: 423:

( i ) SEQUENCE CHARACTERISTICS:

(A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 423:

CACACUGCUG AUGAGGCCGA AAGGCCGAAA UCCCCA                36

(2) INFORMATION FOR SEQ ID NO: 424:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 424:

CGAACAGCUG AUGAGGCCGA AAGGCCGAAA GCCUGG                36

(2) INFORMATION FOR SEQ ID NO: 425:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 425:

GCUGGCUCUG AUGAGGCCGA AAGGCCGAAA UGGCUU                36

(2) INFORMATION FOR SEQ ID NO: 426:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 426:

CUGAUCUCUG AUGAGGCCGA AAGGCCGAAA CUCAAA                36

(2) INFORMATION FOR SEQ ID NO: 427:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 427:

UGGUCUGCUG AUGAGGCCGA AAGGCCGAAA UUCGCU                36

(2) INFORMATION FOR SEQ ID NO: 428:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 428:

AACGUGACUG AUGAGGCCGA AAGGCCGAAA GGGGUU                36

(2) INFORMATION FOR SEQ ID NO: 429:

(i) SEQUENCE CHARACTERISTICS:
        (A) LENGTH: 36 base pairs
        (B) TYPE: nucleic acid (C) STRANDEDNESS: single
(D) TOPOLOGY: linear (xi) SEQUENCE DESCRIPTION: SEQ ID NO: 429:

GAACGUGCUG AUGAGGCCGA AAGGCCGAAA AGGGGU    36

(2) INFORMATION FOR SEQ ID NO: 430:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO: 430:

CUAUAGGCUG AUGAGGCCGA AAGGCCGAAA CGUGAA    36

(2) INFORMATION FOR SEQ ID NO: 431:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO: 431:

UCUAUAGCUG AUGAGGCCGA AAGGCCGAAA ACGUGA    36

(2) INFORMATION FOR SEQ ID NO: 432:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO: 432:

UCCUCUACUG AUGAGGCCGA AAGGCCGAAA GGAACG    36

(2) INFORMATION FOR SEQ ID NO: 433:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO: 433:

GCUCCUCCUG AUGAGGCCGA AAGGCCGAAA UAGGAA    36

(2) INFORMATION FOR SEQ ID NO: 434:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO: 434:

CAAGUCACUG AUGAGGCCGA AAGGCCGAAA GUCCCC    36

(2) INFORMATION FOR SEQ ID NO: 435:

(i) SEQUENCE CHARACTERISTICS:
      (A) LENGTH: 36 base pairs
      (B) TYPE: nucleic acid
      (C) STRANDEDNESS: single
      (D) TOPOLOGY: linear ( x i ) SEQUENCE DESCRIPTION: SEQ ID NO: 435:

GGAAGCACUG AUGAGGCCGA AAGGCCGAAA GGCGCA     36

( 2 ) INFORMATION FOR SEQ ID NO: 436:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 436:

CACCUGGCUG AUGAGGCCGA AAGGCCGAAA GCAGAG     36

( 2 ) INFORMATION FOR SEQ ID NO: 437:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 437:

UCACCUGCUG AUGAGGCCGA AAGGCCGAAA AGCAGA     36

( 2 ) INFORMATION FOR SEQ ID NO: 438:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 438:

GCUGGCUCUG AUGAGGCCGA AAGGCCGAAA UGGCUU     36

( 2 ) INFORMATION FOR SEQ ID NO: 439:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 439:

UCAGGAGCUG AUGAGGCCGA AAGGCCGAAA GGGGCC     36

( 2 ) INFORMATION FOR SEQ ID NO: 440:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 440:

GUGAGAGCUG AUGAGGCCGA AAGGCCGAAA CAGGGG     36

( 2 ) INFORMATION FOR SEQ ID NO: 441:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 441:

GAUGUGACUG AUGAGGCCGA AAGGCCGAAA GGACAG 36

(2) INFORMATION FOR SEQ ID NO: 442:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 442:

GGCUGAGCUG AUGAGGCCGA AAGGCCGAAA AGGGAC 36

(2) INFORMATION FOR SEQ ID NO: 443:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 443:

CAUGGCUCUG AUGAGGCCGA AAGGCCGAAA GGAAGG 36

(2) INFORMATION FOR SEQ ID NO: 444:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 444:

GAGAUGGCUG AUGAGGCCGA AAGGCCGAAA GCAGGA 36

(2) INFORMATION FOR SEQ ID NO: 445:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 445:

UAUCAAACUG AUGAGGCCGA AAGGCCGAAA UCGGAU 36

(2) INFORMATION FOR SEQ ID NO: 446:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 446:

GUUAUCACUG AUGAGGCCGA AAGGCCGAAA AAUCGG 36

(2) INFORMATION FOR SEQ ID NO: 447:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 447:

GGUUAUCCUG AUGAGGCCGA AAGGCCGAAA AAAUCG 36

( 2 ) INFORMATION FOR SEQ ID NO: 448:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 448:

GGAACACCUG AUGAGGCCGA AAGGCCGAAA UGGCCA     36

( 2 ) INFORMATION FOR SEQ ID NO: 449:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 449:

AGAUCUUCUG AUGAGGCCGA AAGGCCGAAA GCUCGG     36

( 2 ) INFORMATION FOR SEQ ID NO: 450:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 450:

CUCGGCACUG AUGAGGCCGA AAGGCCGAAA UCUUGA     36

( 2 ) INFORMATION FOR SEQ ID NO: 451:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 451:

GCUCCCACUG AUGAGGCCGA AAGGCCGAAA GUUCCG     36

( 2 ) INFORMATION FOR SEQ ID NO: 452:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 452:

CCCCACCCUG AUGAGGCCGA AAGGCCGAAA GGCAGC     36

( 2 ) INFORMATION FOR SEQ ID NO: 453:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 453:

GCAAGAACUG AUGAGGCCGA AAGGCCGAAA UCUCAU     36

( 2 ) INFORMATION FOR SEQ ID NO: 454:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 454:

CAGCAAGCUG AUGAGGCCGA AAGGCCGAAA GAUCUC       36

( 2 ) INFORMATION FOR SEQ ID NO: 455:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 455:

ACAGCAACUG AUGAGGCCGA AAGGCCGAAA AGAUCU       36

( 2 ) INFORMATION FOR SEQ ID NO: 456:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 456:

CGCAAUGCUG AUGAGGCCGA AAGGCCGAAA GGAGAA       36

( 2 ) INFORMATION FOR SEQ ID NO: 457:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 457:

ACACCUCCUG AUGAGGCCGA AAGGCCGAAA UGUCUU       36

( 2 ) INFORMATION FOR SEQ ID NO: 458:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 458:

CGUGAAACUG AUGAGGCCGA AAGGCCGAAA CACCUC       36

( 2 ) INFORMATION FOR SEQ ID NO: 459:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 459:

CCCGUGACUG AUGAGGCCGA AAGGCCGAAA UACACC       36

( 2 ) INFORMATION FOR SEQ ID NO: 460:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 460:

UCCCGUGCUG AUGAGGCCGA AAGGCCGAAA AUACAC      36

( 2 ) INFORMATION FOR SEQ ID NO: 461:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 461:

GUCCCGUCUG AUGAGGCCGA AAGGCCGAAA AAUACA      36

( 2 ) INFORMATION FOR SEQ ID NO: 462:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 462:

AGAAAAGCUG AUGAGGCCGA AAGGCCGAAA GCCUCG      36

( 2 ) INFORMATION FOR SEQ ID NO: 463:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 463:

UUGAGAACUG AUGAGGCCGA AAGGCCGAAA GGAGCC      36

( 2 ) INFORMATION FOR SEQ ID NO: 464:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 464:

CUUGAGACUG AUGAGGCCGA AAGGCCGAAA AGGAGC      36

( 2 ) INFORMATION FOR SEQ ID NO: 465:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 465:

GCUUGAGCUG AUGAGGCCGA AAGGCCGAAA AAGGAG      36

( 2 ) INFORMATION FOR SEQ ID NO: 466:

( i ) SEQUENCE CHARACTERISTICS:
        ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO: 466:

AGCUUGACUG AUGAGGCCGA AAGGCCGAAA AAAGGA    36

(2) INFORMATION FOR SEQ ID NO: 467:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 467:

GGAACACCUG AUGAGGCCGA AAGGCCGAAA UGGCCA    36

(2) INFORMATION FOR SEQ ID NO: 468:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 468:

AGUCCGGCUG AUGAGGCCGA AAGGCCGAAA CACAAU    36

(2) INFORMATION FOR SEQ ID NO: 469:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 469:

GAGUCCGCUG AUGAGGCCGA AAGGCCGAAA ACACAA    36

(2) INFORMATION FOR SEQ ID NO: 470:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 470:

GCGUACGCUG AUGAGGCCGA AAGGCCGAAA GGAGUC    36

(2) INFORMATION FOR SEQ ID NO: 471:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 471:

GUCGGCGCUG AUGAGGCCGA AAGGCCGAAA CGGAGG    36

(2) INFORMATION FOR SEQ ID NO: 472:

(i) SEQUENCE CHARACTERISTICS:
(A) LENGTH: 36 base pairs
(B) TYPE: nucleic acid
(C) STRANDEDNESS: single ( D ) TOPOLOGY: linear ( x i ) SEQUENCE DESCRIPTION: SEQ ID NO: 472:

CGAACAGCUG AUGAGGCCGA AAGGCCGAAA GCCUGG   36

( 2 ) INFORMATION FOR SEQ ID NO: 473:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 473:

GCAUGGACUG AUGAGGCCGA AAGGCCGAAA CUCGAA   36

( 2 ) INFORMATION FOR SEQ ID NO: 474:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 474:

CUGCAUGCUG AUGAGGCCGA AAGGCCGAAA GACUCG   36

( 2 ) INFORMATION FOR SEQ ID NO: 475:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 475:

CGAUCAGCUG AUGAGGCCGA AAGGCCGAAA GGCCGC   36

( 2 ) INFORMATION FOR SEQ ID NO: 476:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 476:

GCGAUCACUG AUGAGGCCGA AAGGCCGAAA AGGCCG   36

( 2 ) INFORMATION FOR SEQ ID NO: 477:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 477:

GCUCACUCUG AUGAGGCCGA AAGGCCGAAA GCUCGC   36

( 2 ) INFORMATION FOR SEQ ID NO: 478:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 478:

GUACUGGCUG AUGAGGCCGA AAGGCCGAAA CUCCAU 36

( 2 ) INFORMATION FOR SEQ ID NO: 479:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 479:

AGUACUGCUG AUGAGGCCGA AAGGCCGAAA ACUCCA 36

( 2 ) INFORMATION FOR SEQ ID NO: 480:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 480:

UGGCAAGCUG AUGAGGCCGA AAGGCCGAAA CUGGAA 36

( 2 ) INFORMATION FOR SEQ ID NO: 481:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 481:

UCAUGUGCUG AUGAGGCCGA AAGGCCGAAA UGAGGC 36

( 2 ) INFORMATION FOR SEQ ID NO: 482:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 482:

CGGUGGCCUG AUGAGGCCGA AAGGCCGAAA UCAUCU 36

( 2 ) INFORMATION FOR SEQ ID NO: 483:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 483:

GUCUGGCCUG AUGAGGCCGA AAGGCCGAAA GUACUG 36

( 2 ) INFORMATION FOR SEQ ID NO: 484:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 484:

```
UCUCUUCCUG AUGAGGCCGA AAGGCCGAAA UCCGGU                                36
```

( 2 ) INFORMATION FOR SEQ ID NO: 485:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 485:

```
ACUCUUGCUG AUGAGGCCGA AAGGCCGAAA GGUCUC                                36
```

( 2 ) INFORMATION FOR SEQ ID NO: 486:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 486:

```
GGUCUCACUG AUGAGGCCGA AAGGCCGAAA GGUCCU                                36
```

( 2 ) INFORMATION FOR SEQ ID NO: 487:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 487:

```
ACUCUUGCUG AUGAGGCCGA AAGGCCGAAA GGUCUC                                36
```

( 2 ) INFORMATION FOR SEQ ID NO: 488:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 488:

```
UACUCUUCUG AUGAGGCCGA AAGGCCGAAA AGGUCU                                36
```

( 2 ) INFORMATION FOR SEQ ID NO: 489:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 489:

```
UCUUCAUCUG AUGAGGCCGA AAGGCCGAAA UACUCU                                36
```

( 2 ) INFORMATION FOR SEQ ID NO: 490:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 490:

```
UUGAAAGCUG AUGAGGCCGA AAGGCCGAAA CUCUUC                                36
```

( 2 ) INFORMATION FOR SEQ ID NO: 491:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 491:

CCAUUGACUG AUGAGGCCGA AAGGCCGAAA GGACUC    36

( 2 ) INFORMATION FOR SEQ ID NO: 492:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 492:

UCCAUUGCUG AUGAGGCCGA AAGGCCGAAA AGGACU    36

( 2 ) INFORMATION FOR SEQ ID NO: 493:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 493:

GUCCAUUCUG AUGAGGCCGA AAGGCCGAAA AAGGAC    36

( 2 ) INFORMATION FOR SEQ ID NO: 494:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 494:

CGGGUUGCUG AUGAGGCCGA AAGGCCGAAA GGCCGG    36

( 2 ) INFORMATION FOR SEQ ID NO: 495:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 495:

UUGGAUCCUG AUGAGGCCGA AAGGCCGAAA GGUGUA    36

( 2 ) INFORMATION FOR SEQ ID NO: 496:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 496:

GCACAGCCUG AUGAGGCCGA AAGGCCGAAA UACGCC    36

( 2 ) INFORMATION FOR SEQ ID NO: 497:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 497:

UUUCGGGCUG AUGAGGCCGA AAGGCCGAAA GGCACA                36

( 2 ) INFORMATION FOR SEQ ID NO: 498:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 498:

ACUUCGGCUG AUGAGGCCGA AAGGCCGAAA AGGCUU                36

( 2 ) INFORMATION FOR SEQ ID NO: 499:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 499:

AGAAGUUCUG AUGAGGCCGA AAGGCCGAAA GUUUCG                36

( 2 ) INFORMATION FOR SEQ ID NO: 500:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 500:

GGGACAGCUG AUGAGGCCGA AAGGCCGAAA GUUGAG                36

( 2 ) INFORMATION FOR SEQ ID NO: 501:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 501:

GGGGACACUG AUGAGGCCGA AAGGCCGAAA AGUUGA                36

( 2 ) INFORMATION FOR SEQ ID NO: 502:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 502:

GCUUGGGCUG AUGAGGCCGA AAGGCCGAAA CAGAAG                36

( 2 ) INFORMATION FOR SEQ ID NO: 503:

( i ) SEQUENCE CHARACTERISTICS:

( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 503:

GAAGGUGCUG AUGAGGCCGA AAGGCCGAAA GGGCUG     36

( 2 ) INFORMATION FOR SEQ ID NO: 504:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 504:

GUAAGGCCUG AUGAGGCCGA AAGGCCGAAA UAUGGC     36

( 2 ) INFORMATION FOR SEQ ID NO: 505:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 505:

UGGUGCUCUG AUGAGGCCGA AAGGCCGAAA GGGAUG     36

( 2 ) INFORMATION FOR SEQ ID NO: 506:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 506:

AUGCUGGCUG AUGAGGCCGA AAGGCCGAAA AGGUGU     36

( 2 ) INFORMATION FOR SEQ ID NO: 507:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 507:

GAAGCUGCUG AUGAGGCCGA AAGGCCGAAA GAUGGA     36

( 2 ) INFORMATION FOR SEQ ID NO: 508:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 508:

GCGCGCUCUG AUGAGGCCGA AAGGCCGAAA AGUAAA     36

( 2 ) INFORMATION FOR SEQ ID NO: 509:

( i ) SEQUENCE CHARACTERISTICS:
( A ) LENGTH: 36 base pairs
( B ) TYPE: nucleic acid ( C ) STRANDEDNESS: single
( D ) TOPOLOGY: linear ( x i ) SEQUENCE DESCRIPTION: SEQ ID NO: 509:

GCUGAGGCUG AUGAGGCCGA AAGGCCGAAA UGCUGG 36

( 2 ) INFORMATION FOR SEQ ID NO: 510:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 510:

CAAAGUUCUG AUGAGGCCGA AAGGCCGAAA UGGUGC 36

( 2 ) INFORMATION FOR SEQ ID NO: 511:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 511:

CUCAUCACUG AUGAGGCCGA AAGGCCGAAA GUUGAU 36

( 2 ) INFORMATION FOR SEQ ID NO: 512:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 512:

GGGGGAACUG AUGAGGCCGA AAGGCCGAAA CUCAUC 36

( 2 ) INFORMATION FOR SEQ ID NO: 513:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 513:

UGGGGGACUG AUGAGGCCGA AAGGCCGAAA ACUCAU 36

( 2 ) INFORMATION FOR SEQ ID NO: 514:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 514:

AUGGGGCUG AUGAGGCCGA AAGGCCGAAA AACUCA 36

( 2 ) INFORMATION FOR SEQ ID NO: 515:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 515:

UGAUGGUCUG AUGAGGCCGA AAGGCCGAAA CAGCAU                36

( 2 ) INFORMATION FOR SEQ ID NO: 516:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 516:

CUGAUGGCUG AUGAGGCCGA AAGGCCGAAA ACAGCA                36

( 2 ) INFORMATION FOR SEQ ID NO: 517:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 517:

UCAGGAGCUG AUGAGGCCGA AAGGCCGAAA GGGGCC                36

( 2 ) INFORMATION FOR SEQ ID NO: 518:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 518:

GGCUGAGCUG AUGAGGCCGA AAGGCCGAAA AGGGAC                36

( 2 ) INFORMATION FOR SEQ ID NO: 519:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 519:

CUGCCCUCUG AUGAGGCCGA AAGGCCGAAA UGGUAA                36

( 2 ) INFORMATION FOR SEQ ID NO: 520:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 520:

UCAGACUCUG AUGAGGCCGA AAGGCCGAAA ACUCCC                36

( 2 ) INFORMATION FOR SEQ ID NO: 521:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 521:

GAAGGUGCUG AUGAGGCCGA AAGGCCGAAA GGGCUG 36

(2) INFORMATION FOR SEQ ID NO: 522:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 522:

CGGUGCUCUG AUGAGGCCGA AAGGCCGAAA GGCCAG 36

(2) INFORMATION FOR SEQ ID NO: 523:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 523:

GCUGAGGCUG AUGAGGCCGA AAGGCCGAAA GGGACC 36

(2) INFORMATION FOR SEQ ID NO: 524:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 524:

GGGGCAGCUG AUGAGGCCGA AAGGCCGAAA GCUGGG 36

(2) INFORMATION FOR SEQ ID NO: 525:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 525:

GAGCCUGCUG AUGAGGCCGA AAGGCCGAAA GGCUGG 36

(2) INFORMATION FOR SEQ ID NO: 526:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 526:

GGGGCAGCUG AUGAGGCCGA AAGGCCGAAA GCUGGG 36

(2) INFORMATION FOR SEQ ID NO: 527:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 527:

AGGAAGGCUG AUGAGGCCGA AAGGCCGAAA CCAUGG 36

( 2 ) INFORMATION FOR SEQ ID NO: 528:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 528:

CGCAGCUCUG AUGAGGCCGA AAGGCCGAAA GCCCAC    36

( 2 ) INFORMATION FOR SEQ ID NO: 529:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 529:

UGGGGGACUG AUGAGGCCGA AAGGCCGAAA ACUCAU    36

( 2 ) INFORMATION FOR SEQ ID NO: 530:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 530:

AGACUCGCUG AUGAGGCCGA AAGGCCGAAA CAGGAG    36

( 2 ) INFORMATION FOR SEQ ID NO: 531:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 531:

GGGUUAGCUG AUGAGGCCGA AAGGCCGAAA CUGGGG    36

( 2 ) INFORMATION FOR SEQ ID NO: 532:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 532:

CCGGGUCUG AUGAGGCCGA AAGGCCGAAA GAACUG    36

( 2 ) INFORMATION FOR SEQ ID NO: 533:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 533:

GACUGGGCUG AUGAGGCCGA AAGGCCGAAA GGACCC    36

( 2 ) INFORMATION FOR SEQ ID NO: 534:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 534:

UCAGCUUCUG AUGAGGCCGA AAGGCCGAAA GAAAAG      36

( 2 ) INFORMATION FOR SEQ ID NO: 535:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 535:

GGCUUCCCUG AUGAGGCCGA AAGGCCGAAA CAGCGU      36

( 2 ) INFORMATION FOR SEQ ID NO: 536:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 536:

AGCAUCACUG AUGAGGCCGA AAGGCCGAAA CUGCAG      36

( 2 ) INFORMATION FOR SEQ ID NO: 537:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 537:

CAGCAUCCUG AUGAGGCCGA AAGGCCGAAA ACUGCA      36

( 2 ) INFORMATION FOR SEQ ID NO: 538:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 538:

GCCAAGCCUG AUGAGGCCGA AAGGCCGAAA GGCCCC      36

( 2 ) INFORMATION FOR SEQ ID NO: 539:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 539:

UGUUGCCCUG AUGAGGCCGA AAGGCCGAAA GCAAGG      36

( 2 ) INFORMATION FOR SEQ ID NO: 540:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 540:

GUCUGUGCUG AUGAGGCCGA AAGGCCGAAA CACUCC    36

( 2 ) INFORMATION FOR SEQ ID NO: 541:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 541:

GGUCUGUCUG AUGAGGCCGA AAGGCCGAAA ACACUC    36

( 2 ) INFORMATION FOR SEQ ID NO: 542:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 542:

GUCCACACUG AUGAGGCCGA AAGGCCGAAA UGCCAG    36

( 2 ) INFORMATION FOR SEQ ID NO: 543:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 543:

AGUUCCCUG AUGAGGCCGA AAGGCCGAAA CCGAAG    36

( 2 ) INFORMATION FOR SEQ ID NO: 544:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 544:

AAACUCUCUG AUGAGGCCGA AAGGCCGAAA GUUGUC    36

( 2 ) INFORMATION FOR SEQ ID NO: 545:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 545:

CUGCUGACUG AUGAGGCCGA AAGGCCGAAA CUCUGA    36

( 2 ) INFORMATION FOR SEQ ID NO: 546:

( i ) SEQUENCE CHARACTERISTICS:
      ( A ) LENGTH: 36 base pairs (B) TYPE: nucleic acid
        (C) STRANDEDNESS: single
        (D) TOPOLOGY: linear (xi) SEQUENCE DESCRIPTION: SEQ ID NO: 546:

GCUGCUGCUG AUGAGGCCGA AAGGCCGAAA ACUCUG                        36

(2) INFORMATION FOR SEQ ID NO: 547:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 547:

AGCUGCUCUG AUGAGGCCGA AAGGCCGAAA AACUCU                        36

(2) INFORMATION FOR SEQ ID NO: 548:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 548:

ACACAGGCUG AUGAGGCCGA AAGGCCGAAA UGCACC                        36

(2) INFORMATION FOR SEQ ID NO: 549:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 549:

UUCAGGGCUG AUGAGGCCGA AAGGCCGAAA CUCCAU                        36

(2) INFORMATION FOR SEQ ID NO: 550:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 550:

CGAGUUACUG AUGAGGCCGA AAGGCCGAAA GCUUCA                        36

(2) INFORMATION FOR SEQ ID NO: 551:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 551:

GGCGAGUCUG AUGAGGCCGA AAGGCCGAAA UAGCUU                        36

(2) INFORMATION FOR SEQ ID NO: 552:

(i) SEQUENCE CHARACTERISTICS:
        (A) LENGTH: 36 base pairs
        (B) TYPE: nucleic acid
        (C) STRANDEDNESS: single ( D ) TOPOLOGY: linear ( x i ) SEQUENCE DESCRIPTION: SEQ ID NO: 552:

ACCAGGCUG AUGAGGCCGA AAGGCCGAAA GUUAUA                36

( 2 ) INFORMATION FOR SEQ ID NO: 553:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 553:

CCCUCUCCUG AUGAGGCCGA AAGGCCGAAA GGAGAG                36

( 2 ) INFORMATION FOR SEQ ID NO: 554:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 554:

GGGGCAGCUG AUGAGGCCGA AAGGCCGAAA GCUGGG                36

( 2 ) INFORMATION FOR SEQ ID NO: 555:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 555:

CCUACCGCUG AUGAGGCCGA AAGGCCGAAA GCAGGA                36

( 2 ) INFORMATION FOR SEQ ID NO: 556:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 556:

CAUUGGGCUG AUGAGGCCGA AAGGCCGAAA GCCCCG                36

( 2 ) INFORMATION FOR SEQ ID NO: 557:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 557:

CUGGGCACUG AUGAGGCCGA AAGGCCGAAA GGUCAG                36

( 2 ) INFORMATION FOR SEQ ID NO: 558:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 558:

CACCUGGCUG AUGAGGCCGA AAGGCCGAAA GCAGAG    36

( 2 ) INFORMATION FOR SEQ ID NO: 559:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 559:

UCACCUGCUG AUGAGGCCGA AAGGCCGAAA AGCAGA    36

( 2 ) INFORMATION FOR SEQ ID NO: 560:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 560:

ACCUCCGCUG AUGAGGCCGA AAGGCCGAAA AGCGAG    36

( 2 ) INFORMATION FOR SEQ ID NO: 561:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 561:

GGAGGAGCUG AUGAGGCCGA AAGGCCGAAA GUCUUC    36

( 2 ) INFORMATION FOR SEQ ID NO: 562:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 562:

UGGAGGACUG AUGAGGCCGA AAGGCCGAAA AGUCUU    36

( 2 ) INFORMATION FOR SEQ ID NO: 563:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 563:

AAUGGAGCUG AUGAGGCCGA AAGGCCGAAA GAAGUC    36

( 2 ) INFORMATION FOR SEQ ID NO: 564:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 564:

```
CGCAAUGCUG AUGAGGCCGA AAGGCCGAAA GGAGAA                                    36
```

( 2 ) INFORMATION FOR SEQ ID NO: 565:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 565:

```
UGUCCGCCUG AUGAGGCCGA AAGGCCGAAA UGGAGG                                    36
```

( 2 ) INFORMATION FOR SEQ ID NO: 566:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 566:

```
AGCAGAGCUG AUGAGGCCGA AAGGCCGAAA GUCCAU                                    36
```

( 2 ) INFORMATION FOR SEQ ID NO: 567:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 567:

```
GAGCAGACUG AUGAGGCCGA AAGGCCGAAA AGUCCA                                    36
```

( 2 ) INFORMATION FOR SEQ ID NO: 568:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 568:

```
AAGAGCACUG AUGAGGCCGA AAGGCCGAAA GAAGUC                                    36
```

( 2 ) INFORMATION FOR SEQ ID NO: 569:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 569:

```
CUGAUCUCUG AUGAGGCCGA AAGGCCGAAA CUCAAA                                    36
```

( 2 ) INFORMATION FOR SEQ ID NO: 570:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 570:

```
AGGAGCUCUG AUGAGGCCGA AAGGCCGAAA UCUGAC                                    36
```

( 2 ) INFORMATION FOR SEQ ID NO: 571:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 571:

ACCUUAGCUG AUGAGGCCGA AAGGCCGAAA GCUGAU             36

( 2 ) INFORMATION FOR SEQ ID NO: 572:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 572:

AGCACCUCUG AUGAGGCCGA AAGGCCGAAA GGAGCU             36

( 2 ) INFORMATION FOR SEQ ID NO: 573:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 573:

CUCUUGGCUG AUGAGGCCGA AAGGCCGAAA GCACUG             36

( 2 ) INFORMATION FOR SEQ ID NO: 574:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 574:

UACAGACCUG AUGAGGCCGA AAGGCCGAAA GCCAUU             36

( 2 ) INFORMATION FOR SEQ ID NO: 575:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 575:

CACUACACUG AUGAGGCCGA AAGGCCGAAA CGAGCC             36

( 2 ) INFORMATION FOR SEQ ID NO: 576:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 576:

CGUGCACCUG AUGAGGCCGA AAGGCCGAAA CAGACG             36

( 2 ) INFORMATION FOR SEQ ID NO: 577:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 577:

GAGGGGGCUG AUGAGGCCGA AAGGCCGAAA CAGUUC      36

( 2 ) INFORMATION FOR SEQ ID NO: 578:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 578:

UGAGGGGCUG AUGAGGCCGA AAGGCCGAAA ACAGUU      36

( 2 ) INFORMATION FOR SEQ ID NO: 579:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 579:

GGAAGAUCUG AUGAGGCCGA AAGGCCGAAA GGGGGA      36

( 2 ) INFORMATION FOR SEQ ID NO: 580:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 580:

CCGGGAACUG AUGAGGCCGA AAGGCCGAAA UGAGGG      36

( 2 ) INFORMATION FOR SEQ ID NO: 581:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 581:

UGCCGGGCUG AUGAGGCCGA AAGGCCGAAA GAUGAG      36

( 2 ) INFORMATION FOR SEQ ID NO: 582:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 582:

CUGCCGGCUG AUGAGGCCGA AAGGCCGAAA AGAUGA      36

( 2 ) INFORMATION FOR SEQ ID NO: 583:

( i ) SEQUENCE CHARACTERISTICS:

( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 583:

GGGGCCACUG AUGAGGCCGA AAGGCCGAAA GGCCUG 36

( 2 ) INFORMATION FOR SEQ ID NO: 584:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 584:

CUCCACACUG AUGAGGCCGA AAGGCCGAAA GGGGCC 36

( 2 ) INFORMATION FOR SEQ ID NO: 585:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 585:

GCUCAAUCUG AUGAGGCCGA AAGGCCGAAA UCUCCA 36

( 2 ) INFORMATION FOR SEQ ID NO: 586:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 586:

GCUGCUCCUG AUGAGGCCGA AAGGCCGAAA UGAUCU 36

( 2 ) INFORMATION FOR SEQ ID NO: 587:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 587:

GUAGCGGCUG AUGAGGCCGA AAGGCCGAAA GCGCAU 36

( 2 ) INFORMATION FOR SEQ ID NO: 588:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 588:

UGUAGCGCUG AUGAGGCCGA AAGGCCGAAA AGCGCA 36

( 2 ) INFORMATION FOR SEQ ID NO: 589:

( i ) SEQUENCE CHARACTERISTICS:
( A ) LENGTH: 36 base pairs
( B ) TYPE: nucleic acid ( C ) STRANDEDNESS: single
            ( D ) TOPOLOGY: linear ( x i ) SEQUENCE DESCRIPTION: SEQ ID NO: 589:

GCACUUGCUG AUGAGGCCGA AAGGCCGAAA GCGGAA                36

( 2 ) INFORMATION FOR SEQ ID NO: 590:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 590:

GCCCGCGCUG AUGAGGCCGA AAGGCCGAAA GCGCCC                36

( 2 ) INFORMATION FOR SEQ ID NO: 591:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 591:

CGCCUGGCUG AUGAGGCCGA AAGGCCGAAA UGCUGC                36

( 2 ) INFORMATION FOR SEQ ID NO: 592:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 592:

UUGGUGGCUG AUGAGGCCGA AAGGCCGAAA UCUGUG                36

( 2 ) INFORMATION FOR SEQ ID NO: 593:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 593:

UGAUCUUCUG AUGAGGCCGA AAGGCCGAAA UGGUGG                36

( 2 ) INFORMATION FOR SEQ ID NO: 594:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 594:

AGCCAUUCUG AUGAGGCCGA AAGGCCGAAA UCUUGA                36

( 2 ) INFORMATION FOR SEQ ID NO: 595:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 595:

UCCUGUGCUG AUGAGGCCGA AAGGCCGAAA GCCAUU 36

( 2 ) INFORMATION FOR SEQ ID NO: 596:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 596:

CCAGGGACUG AUGAGGCCGA AAGGCCGAAA UGCGCA 36

( 2 ) INFORMATION FOR SEQ ID NO: 597:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 597:

GACCAGGCUG AUGAGGCCGA AAGGCCGAAA GAUGCG 36

( 2 ) INFORMATION FOR SEQ ID NO: 598:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 598:

CCUUGGUCUG AUGAGGCCGA AAGGCCGAAA CCAGGG 36

( 2 ) INFORMATION FOR SEQ ID NO: 599:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 599:

CGGUGAGCUG AUGAGGCCGA AAGGCCGAAA GGGUCC 36

( 2 ) INFORMATION FOR SEQ ID NO: 600:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 600:

GGCCGGUCUG AUGAGGCCGA AAGGCCGAAA GGAGGG 36

( 2 ) INFORMATION FOR SEQ ID NO: 601:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 601:

UGGGGGUCUG AUGAGGCCGA AAGGCCGAAA GGCCGG　　　　　　　　　　　　　　36

( 2 ) INFORMATION FOR SEQ ID NO: 602:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 602:

UUCCUACCUG AUGAGGCCGA AAGGCCGAAA GCUCGU　　　　　　　　　　　　　　36

( 2 ) INFORMATION FOR SEQ ID NO: 603:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 603:

CCUUUCCCUG AUGAGGCCGA AAGGCCGAAA CAAGCU　　　　　　　　　　　　　　36

( 2 ) INFORMATION FOR SEQ ID NO: 604:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 604:

CUCAUAGCUG AUGAGGCCGA AAGGCCGAAA GCCAUC　　　　　　　　　　　　　　36

( 2 ) INFORMATION FOR SEQ ID NO: 605:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 605:

CCUCAUACUG AUGAGGCCGA AAGGCCGAAA AGCCAU　　　　　　　　　　　　　　36

( 2 ) INFORMATION FOR SEQ ID NO: 606:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 606:

AGCCUCACUG AUGAGGCCGA AAGGCCGAAA GAAGCC　　　　　　　　　　　　　　36

( 2 ) INFORMATION FOR SEQ ID NO: 607:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 607:

CCGGGCACUG AUGAGGCCGA AAGGCCGAAA GCUCAG　　　　　　　　　　　　　　36

( 2 ) INFORMATION FOR SEQ ID NO: 608:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 608:

AACUGUGCUG AUGAGGCCGA AAGGCCGAAA UGCAGC    36

( 2 ) INFORMATION FOR SEQ ID NO: 609:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 609:

UUCUGGACUG AUGAGGCCGA AAGGCCGAAA CUGUGG    36

( 2 ) INFORMATION FOR SEQ ID NO: 610:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 610:

GUUCUGGCUG AUGAGGCCGA AAGGCCGAAA ACUGUG    36

( 2 ) INFORMATION FOR SEQ ID NO: 611:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 611:

GGUUCUGCUG AUGAGGCCGA AAGGCCGAAA AACUGU    36

( 2 ) INFORMATION FOR SEQ ID NO: 612:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 612:

CACACUGCUG AUGAGGCCGA AAGGCCGAAA UUCCCA    36

( 2 ) INFORMATION FOR SEQ ID NO: 613:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 613:

UGACUGACUG AUGAGGCCGA AAGGCCGAAA GCCUGC    36

( 2 ) INFORMATION FOR SEQ ID NO: 614:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 614:

GCUGACUCUG AUGAGGCCGA AAGGCCGAAA UAGCCU     36

( 2 ) INFORMATION FOR SEQ ID NO: 615:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 615:

AUGCGCUCUG AUGAGGCCGA AAGGCCGAAA CUGAUA     36

( 2 ) INFORMATION FOR SEQ ID NO: 616:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 616:

UGGUCUGCUG AUGAGGCCGA AAGGCCGAAA UGCGCU     36

( 2 ) INFORMATION FOR SEQ ID NO: 617:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 617:

AACUUGGCUG AUGAGGCCGA AAGGCCGAAA GGGGUU     36

( 2 ) INFORMATION FOR SEQ ID NO: 618:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 618:

GAACUUGCUG AUGAGGCCGA AAGGCCGAAA AGGGGU     36

( 2 ) INFORMATION FOR SEQ ID NO: 619:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 619:

CUAUAGGCUG AUGAGGCCGA AAGGCCGAAA CUUGGA     36

( 2 ) INFORMATION FOR SEQ ID NO: 620:

5,658,780

233

234

-continued ( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 620:

UCUAUAGCUG AUGAGGCCGA AAGGCCGAAA ACUUGG      36

( 2 ) INFORMATION FOR SEQ ID NO: 621:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 621:

UCUUCUACUG AUGAGGCCGA AAGGCCGAAA GGAACU      36

( 2 ) INFORMATION FOR SEQ ID NO: 622:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 622:

GCUCUUCCUG AUGAGGCCGA AAGGCCGAAA UAGGAA      36

( 2 ) INFORMATION FOR SEQ ID NO: 623:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 623:

CAGGUCGCUG AUGAGGCCGA AAGGCCGAAA GUCCCC      36

( 2 ) INFORMATION FOR SEQ ID NO: 624:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 624:

GGAAGCACUG AUGAGGCCGA AAGGCCGAAA GCCGCA      36

( 2 ) INFORMATION FOR SEQ ID NO: 625:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 625:

CACCUGGCUG AUGAGGCCGA AAGGCCGAAA GCAGAG      36

( 2 ) INFORMATION FOR SEQ ID NO: 626:

( i ) SEQUENCE CHARACTERISTICS:
        ( A ) LENGTH: 36 base pairs ( B ) TYPE: nucleic acid
( C ) STRANDEDNESS: single
( D ) TOPOLOGY: linear ( x i ) SEQUENCE DESCRIPTION: SEQ ID NO: 626:

UCACCUGCUG AUGAGGCCGA AAGGCCGAAA AGCAGA 36

( 2 ) INFORMATION FOR SEQ ID NO: 627:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 627:

CCUGCCUCUG AUGAGGCCGA AAGGCCGAAA UGGGUC 36

( 2 ) INFORMATION FOR SEQ ID NO: 628:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 628:

GCAGGCGCUG AUGAGGCCGA AAGGCCGAAA GGGGCC 36

( 2 ) INFORMATION FOR SEQ ID NO: 629:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 629:

GAGGAAGCUG AUGAGGCCGA AAGGCCGAAA CAGGCG 36

( 2 ) INFORMATION FOR SEQ ID NO: 630:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 630:

GAUGAGGCUG AUGAGGCCGA AAGGCCGAAA GGACAG 36

( 2 ) INFORMATION FOR SEQ ID NO: 631:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 631:

GGAUGAGCUG AUGAGGCCGA AAGGCCGAAA AGGACA 36

( 2 ) INFORMATION FOR SEQ ID NO: 632:

( i ) SEQUENCE CHARACTERISTICS:
( A ) LENGTH: 36 base pairs
( B ) TYPE: nucleic acid
( C ) STRANDEDNESS: single ( D ) TOPOLOGY: linear ( x i ) SEQUENCE DESCRIPTION: SEQ ID NO: 632:

AUGGGAUCUG AUGAGGCCGA AAGGCCGAAA GGAAGG                        36

( 2 ) INFORMATION FOR SEQ ID NO: 633:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 633:

AAGAUGGCUG AUGAGGCCGA AAGGCCGAAA UGAGGA                        36

( 2 ) INFORMATION FOR SEQ ID NO: 634:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 634:

UGUCAAACUG AUGAGGCCGA AAGGCCGAAA UGGGAU                        36

( 2 ) INFORMATION FOR SEQ ID NO: 635:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 635:

AUUGUCACUG AUGAGGCCGA AAGGCCGAAA GAUGGG                        36

( 2 ) INFORMATION FOR SEQ ID NO: 636:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 636:

GAUUGUCCUG AUGAGGCCGA AAGGCCGAAA AGAUGG                        36

( 2 ) INFORMATION FOR SEQ ID NO: 637:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 637:

GGGGCACCUG AUGAGGCCGA AAGGCCGAAA UUGUCA                        36

( 2 ) INFORMATION FOR SEQ ID NO: 638:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 638:

AGAUCUUCUG AUGAGGCCGA AAGGCCGAAA GCUCGG    36

( 2 ) INFORMATION FOR SEQ ID NO: 639:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 639:

CUCGGCACUG AUGAGGCCGA AAGGCCGAAA UCUUGA    36

( 2 ) INFORMATION FOR SEQ ID NO: 640:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 640:

GCUGCCACUG AUGAGGCCGA AAGGCCGAAA GUUUCG    36

( 2 ) INFORMATION FOR SEQ ID NO: 641:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 641:

CCCCACCCUG AUGAGGCCGA AAGGCCGAAA GGCAGC    36

( 2 ) INFORMATION FOR SEQ ID NO: 642:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 642:

GUAGGAACUG AUGAGGCCGA AAGGCCGAAA UCUCAU    36

( 2 ) INFORMATION FOR SEQ ID NO: 643:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 643:

CAGUAGGCUG AUGAGGCCGA AAGGCCGAAA GAUCUC    36

( 2 ) INFORMATION FOR SEQ ID NO: 644:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 644:

ACAGUAGCUG AUGAGGCCGA AAGGCCGAAA AGAUCU 36

(2) INFORMATION FOR SEQ ID NO: 645:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 645:

CACACAGCUG AUGAGGCCGA AAGGCCGAAA GGAAGA 36

(2) INFORMATION FOR SEQ ID NO: 646:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 646:

ACACCUCCUG AUGAGGCCGA AAGGCCGAAA UGUCCU 36

(2) INFORMATION FOR SEQ ID NO: 647:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 647:

CGUGAAACUG AUGAGGCCGA AAGGCCGAAA CACCUC 36

(2) INFORMATION FOR SEQ ID NO: 648:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 648:

CCCGUGACUG AUGAGGCCGA AAGGCCGAAA UACACC 36

(2) INFORMATION FOR SEQ ID NO: 649:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 649:

UCCCGUGCUG AUGAGGCCGA AAGGCCGAAA AUACAC 36

(2) INFORMATION FOR SEQ ID NO: 650:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 650:

GUCCCGUCUG AUGAGGCCGA AAGGCCGAAA AAUACA 36

( 2 ) INFORMATION FOR SEQ ID NO: 651:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 651:

CGAAAAGCUG AUGAGGCCGA AAGGCCGAAA GCCUCG    36

( 2 ) INFORMATION FOR SEQ ID NO: 652:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 652:

UUGCGAACUG AUGAGGCCGA AAGGCCGAAA GGAGCC    36

( 2 ) INFORMATION FOR SEQ ID NO: 653:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 653:

CUUGCGACUG AUGAGGCCGA AAGGCCGAAA AGGAGC    36

( 2 ) INFORMATION FOR SEQ ID NO: 654:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 654:

GCUUGCGCUG AUGAGGCCGA AAGGCCGAAA AAGGAG    36

( 2 ) INFORMATION FOR SEQ ID NO: 655:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 655:

AGCUUGCCUG AUGAGGCCGA AAGGCCGAAA AAAGGA    36

( 2 ) INFORMATION FOR SEQ ID NO: 656:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 656:

GGAACACCUG AUGAGGCCGA AAGGCCGAAA UGGCCA    36

( 2 ) INFORMATION FOR SEQ ID NO: 657:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 657:

GGUCCGGCUG AUGAGGCCGA AAGGCCGAAA CACAAU    36

( 2 ) INFORMATION FOR SEQ ID NO: 658:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 658:

GGGUCCGCUG AUGAGGCCGA AAGGCCGAAA ACACAA    36

( 2 ) INFORMATION FOR SEQ ID NO: 659:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 659:

GCGUAGGCUG AUGAGGCCGA AAGGCCGAAA GGGGUC    36

( 2 ) INFORMATION FOR SEQ ID NO: 660:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 660:

GUCUGCGCUG AUGAGGCCGA AAGGCCGAAA GGGAGG    36

( 2 ) INFORMATION FOR SEQ ID NO: 661:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 661:

CGCACAGCUG AUGAGGCCGA AAGGCCGAAA GCCUGC    36

( 2 ) INFORMATION FOR SEQ ID NO: 662:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 662:

GCAUGGACUG AUGAGGCCGA AAGGCCGAAA CACGCA    36

( 2 ) INFORMATION FOR SEQ ID NO: 663:

( i ) SEQUENCE CHARACTERISTICS:

(A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 663:

CUGCAUGCUG AUGAGGCCGA AAGGCCGAAA GACACG    36

(2) INFORMATION FOR SEQ ID NO: 664:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 664:

CGGUCGGCUG AUGAGGCCGA AAGGCCGAAA GGCCGC    36

(2) INFORMATION FOR SEQ ID NO: 665:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 665:

CCGGUCGCUG AUGAGGCCGA AAGGCCGAAA AGGCCG    36

(2) INFORMATION FOR SEQ ID NO: 666:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 666:

GCUCACUCUG AUGAGGCCGA AAGGCCGAAA GCUCCC    36

(2) INFORMATION FOR SEQ ID NO: 667:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 667:

GUACUGGCUG AUGAGGCCGA AAGGCCGAAA UUCCAU    36

(2) INFORMATION FOR SEQ ID NO: 668:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 668:

GGUACUGCUG AUGAGGCCGA AAGGCCGAAA AUUCCA    36

(2) INFORMATION FOR SEQ ID NO: 669:

(i) SEQUENCE CHARACTERISTICS:
        (A) LENGTH: 36 base pairs
        (B) TYPE: nucleic acid ( C ) STRANDEDNESS: single
( D ) TOPOLOGY: linear ( x i ) SEQUENCE DESCRIPTION: SEQ ID NO: 669:

UGGCAGGCUG AUGAGGCCGA AAGGCCGAAA CUGGAA        36

( 2 ) INFORMATION FOR SEQ ID NO: 670:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 670:

UCGUCUGCUG AUGAGGCCGA AAGGCCGAAA UCUGGC        36

( 2 ) INFORMATION FOR SEQ ID NO: 671:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 671:

CGGUGACCUG AUGAGGCCGA AAGGCCGAAA UCGUCU        36

( 2 ) INFORMATION FOR SEQ ID NO: 672:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 672:

AUCCGGUCUG AUGAGGCCGA AAGGCCGAAA CGAUCG        36

( 2 ) INFORMATION FOR SEQ ID NO: 673:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 673:

UCUCCUCCUG AUGAGGCCGA AAGGCCGAAA UCCGGU        36

( 2 ) INFORMATION FOR SEQ ID NO: 674:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 674:

GUCCUUUCUG AUGAGGCCGA AAGGCCGAAA CGUUUC        36

( 2 ) INFORMATION FOR SEQ ID NO: 675:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 675:

GGUCUCACUG AUGAGGCCGA AAGGCCGAAA UGUCCU    36

( 2 ) INFORMATION FOR SEQ ID NO: 676:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 676:

GCUCUUGCUG AUGAGGCCGA AAGGCCGAAA GGUCUC    36

( 2 ) INFORMATION FOR SEQ ID NO: 677:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 677:

UGCUCUUCUG AUGAGGCCGA AAGGCCGAAA AGGUCU    36

( 2 ) INFORMATION FOR SEQ ID NO: 678:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 678:

UCUUCAUCUG AUGAGGCCGA AAGGCCGAAA UGCUCU    36

( 2 ) INFORMATION FOR SEQ ID NO: 679:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 679:

CUGAAAGCUG AUGAGGCCGA AAGGCCGAAA CUCUUC    36

( 2 ) INFORMATION FOR SEQ ID NO: 680:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 680:

CCGCUGACUG AUGAGGCCGA AAGGCCGAAA GGACUC    36

( 2 ) INFORMATION FOR SEQ ID NO: 681:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 681:

UCCGCUGCUG AUGAGGCCGA AAGGCCGAAA AGGACU 36

( 2 ) INFORMATION FOR SEQ ID NO: 682:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 682:

GUCCGCUCUG AUGAGGCCGA AAGGCCGAAA AAGGAC 36

( 2 ) INFORMATION FOR SEQ ID NO: 683:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 683:

CGAGGUGCUG AUGAGGCCGA AAGGCCGAAA GGCCGG 36

( 2 ) INFORMATION FOR SEQ ID NO: 684:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 684:

AUGCGUCCUG AUGAGGCCGA AAGGCCGAAA GGUGGA 36

( 2 ) INFORMATION FOR SEQ ID NO: 685:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 685:

GCACAGCCUG AUGAGGCCGA AAGGCCGAAA UGCGUC 36

( 2 ) INFORMATION FOR SEQ ID NO: 686:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 686:

CUGCGGGCUG AUGAGGCCGA AAGGCCGAAA GGCACA 36

( 2 ) INFORMATION FOR SEQ ID NO: 687:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 687:

GCUGCGGCUG AUGAGGCCGA AAGGCCGAAA AGGCAC 36

( 2 ) INFORMATION FOR SEQ ID NO: 688:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 688:

AGAAGCUCUG AUGAGGCCGA AAGGCCGAAA GCUGCG      36

( 2 ) INFORMATION FOR SEQ ID NO: 689:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 689:

GGGACAGCUG AUGAGGCCGA AAGGCCGAAA GCUGAG      36

( 2 ) INFORMATION FOR SEQ ID NO: 690:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 690:

GGGGACACUG AUGAGGCCGA AAGGCCGAAA AGCUGA      36

( 2 ) INFORMATION FOR SEQ ID NO: 691:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 691:

GCUUGGGCUG AUGAGGCCGA AAGGCCGAAA CAGAAG      36

( 2 ) INFORMATION FOR SEQ ID NO: 692:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 692:

AAAGGGACUG AUGAGGCCGA AAGGCCGAAA GGGCUG      36

( 2 ) INFORMATION FOR SEQ ID NO: 693:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 693:

GUAAAGGCUG AUGAGGCCGA AAGGCCGAAA UAGGGC      36

( 2 ) INFORMATION FOR SEQ ID NO: 694:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 694:

UGACGUACUG AUGAGGCCGA AAGGCCGAAA GGGAUA                    36

( 2 ) INFORMATION FOR SEQ ID NO: 695:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 695:

AUGACGUCUG AUGAGGCCGA AAGGCCGAAA AGGGAU                    36

( 2 ) INFORMATION FOR SEQ ID NO: 696:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 696:

GAUGACGCUG AUGAGGCCGA AAGGCCGAAA AAGGGA                    36

( 2 ) INFORMATION FOR SEQ ID NO: 697:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 697:

CAGGGAUCUG AUGAGGCCGA AAGGCCGAAA CGUAAA                    36

( 2 ) INFORMATION FOR SEQ ID NO: 698:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 698:

GCUCAGGCUG AUGAGGCCGA AAGGCCGAAA UGACGU                    36

( 2 ) INFORMATION FOR SEQ ID NO: 699:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 699:

CAUAGUUCUG AUGAGGCCGA AAGGCCGAAA UGGUGC                    36

( 2 ) INFORMATION FOR SEQ ID NO: 700:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 700:

CUCAUCACUG AUGAGGCCGA AAGGCCGAAA GUUGAU 36

( 2 ) INFORMATION FOR SEQ ID NO: 701:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 701:

GGUGGGACUG AUGAGGCCGA AAGGCCGAAA CUCAUC 36

( 2 ) INFORMATION FOR SEQ ID NO: 702:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 702:

UGGUGGGCUG AUGAGGCCGA AAGGCCGAAA ACUCAU 36

( 2 ) INFORMATION FOR SEQ ID NO: 703:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 703:

AUGGUGGCUG AUGAGGCCGA AAGGCCGAAA AACUCA 36

( 2 ) INFORMATION FOR SEQ ID NO: 704:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 704:

AGAAGGACUG AUGAGGCCGA AAGGCCGAAA CACCAU 36

( 2 ) INFORMATION FOR SEQ ID NO: 705:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 705:

CAGAAGGCUG AUGAGGCCGA AAGGCCGAAA ACACCA 36

( 2 ) INFORMATION FOR SEQ ID NO: 706:

( i ) SEQUENCE CHARACTERISTICS:
  ( A ) LENGTH: 36 base pairs (B) TYPE: nucleic acid
    (C) STRANDEDNESS: single
    (D) TOPOLOGY: linear (xi) SEQUENCE DESCRIPTION: SEQ ID NO: 706:

CCAGAAGCUG AUGAGGCCGA AAGGCCGAAA AACACC                36

(2) INFORMATION FOR SEQ ID NO: 707:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO: 707:

UGCCCAGCUG AUGAGGCCGA AAGGCCGAAA GGAAAC                36

(2) INFORMATION FOR SEQ ID NO: 708:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO: 708:

CUGCCCACUG AUGAGGCCGA AAGGCCGAAA AGGAAA                36

(2) INFORMATION FOR SEQ ID NO: 709:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO: 709:

CCUGGCUCUG AUGAGGCCGA AAGGCCGAAA UCUGCC                36

(2) INFORMATION FOR SEQ ID NO: 710:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO: 710:

CAAGGCCCUG AUGAGGCCGA AAGGCCGAAA GGCCUG                36

(2) INFORMATION FOR SEQ ID NO: 711:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO: 711:

CGGGGCCCUG AUGAGGCCGA AAGGCCGAAA GGCCGA                36

(2) INFORMATION FOR SEQ ID NO: 712:

(i) SEQUENCE CHARACTERISTICS:
    (A) LENGTH: 36 base pairs
    (B) TYPE: nucleic acid
    (C) STRANDEDNESS: single ( D ) TOPOLOGY: linear ( x i ) SEQUENCE DESCRIPTION: SEQ ID NO: 712:

ACUUGGGCUG AUGAGGCCGA AAGGCCGAAA GGGGCC 36

( 2 ) INFORMATION FOR SEQ ID NO: 713:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 713:

GGGGCAGCUG AUGAGGCCGA AAGGCCGAAA CUUGGG 36

( 2 ) INFORMATION FOR SEQ ID NO: 714:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 714:

GGGGCUGCUG AUGAGGCCGA AAGGCCGAAA GCCUGG 36

( 2 ) INFORMATION FOR SEQ ID NO: 715:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 715:

AUGGCUGCUG AUGAGGCCGA AAGGCCGAAA GCAGGG 36

( 2 ) INFORMATION FOR SEQ ID NO: 716:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 716:

GAGCUGACUG AUGAGGCCGA AAGGCCGAAA CCAUGG 36

( 2 ) INFORMATION FOR SEQ ID NO: 717:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 717:

CAGAGCUCUG AUGAGGCCGA AAGGCCGAAA UACCAU 36

( 2 ) INFORMATION FOR SEQ ID NO: 718:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear (x i) SEQUENCE DESCRIPTION: SEQ ID NO: 718:

UGGGCCACUG AUGAGGCCGA AAGGCCGAAA GCUGAU                                 36

(2) INFORMATION FOR SEQ ID NO: 719:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 719:

GGACUGGCUG AUGAGGCCGA AAGGCCGAAA CAGGGG                                 36

(2) INFORMATION FOR SEQ ID NO: 720:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 720:

GGGCUAGCUG AUGAGGCCGA AAGGCCGAAA CUGGGA                                 36

(2) INFORMATION FOR SEQ ID NO: 721:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 721:

CUGGGGCCUG AUGAGGCCGA AAGGCCGAAA GGACUG                                 36

(2) INFORMATION FOR SEQ ID NO: 722:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 722:

GCCUGAGCUG AUGAGGCCGA AAGGCCGAAA GGGCCU                                 36

(2) INFORMATION FOR SEQ ID NO: 723:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 723:

ACAGCCUCUG AUGAGGCCGA AAGGCCGAAA GGAGGG                                 36

(2) INFORMATION FOR SEQ ID NO: 724:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 724:

GGCCUCUCUG AUGAGGCCGA AAGGCCGAAA CAGCGU                    36

( 2 ) INFORMATION FOR SEQ ID NO: 725:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 725:

AUCAUCACUG AUGAGGCCGA AAGGCCGAAA CUGCAG                    36

( 2 ) INFORMATION FOR SEQ ID NO: 726:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 726:

CAUCAUCCUG AUGAGGCCGA AAGGCCGAAA ACUGCA                    36

( 2 ) INFORMATION FOR SEQ ID NO: 727:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 727:

GCCAAGCCUG AUGAGGCCGA AAGGCCGAAA GGCCCC                    36

( 2 ) INFORMATION FOR SEQ ID NO: 728:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 728:

UGUUGCCCUG AUGAGGCCGA AAGGCCGAAA GCAAGG                    36

( 2 ) INFORMATION FOR SEQ ID NO: 729:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 729:

GUCUGUGCUG AUGAGGCCGA AAGGCCGAAA CACAGC                    36

( 2 ) INFORMATION FOR SEQ ID NO: 730:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 730:

GGUCUGUCUG AUGAGGCCGA AAGGCCGAAA ACACAG                    36

( 2 ) INFORMATION FOR SEQ ID NO: 731:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 731:

GUCGACGCUG AUGAGGCCGA AAGGCCGAAA UGCCAG    36

( 2 ) INFORMATION FOR SEQ ID NO: 732:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 732:

AGUUGUCCUG AUGAGGCCGA AAGGCCGAAA CGGAUG    36

( 2 ) INFORMATION FOR SEQ ID NO: 733:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 733:

AAACUCGCUG AUGAGGCCGA AAGGCCGAAA GUUGUC    36

( 2 ) INFORMATION FOR SEQ ID NO: 734:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 734:

CUGCUGACUG AUGAGGCCGA AAGGCCGAAA CUCGGA    36

( 2 ) INFORMATION FOR SEQ ID NO: 735:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 735:

GCUGCUGCUG AUGAGGCCGA AAGGCCGAAA ACUCGG    36

( 2 ) INFORMATION FOR SEQ ID NO: 736:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 736:

AGCUGCUCUG AUGAGGCCGA AAGGCCGAAA AACUCG    36

( 2 ) INFORMATION FOR SEQ ID NO: 737:

( i ) SEQUENCE CHARACTERISTICS:
: ( A ) LENGTH: 36 base pairs
: ( B ) TYPE: nucleic acid
: ( C ) STRANDEDNESS: single
: ( D ) TOPOLOGY: linear ( x i ) SEQUENCE DESCRIPTION: SEQ ID NO: 737:

CCACAGGCUG AUGAGGCCGA AAGGCCGAAA UGCCCU 36

( 2 ) INFORMATION FOR SEQ ID NO: 738:

: ( i ) SEQUENCE CHARACTERISTICS:
: ( A ) LENGTH: 36 base pairs
: ( B ) TYPE: nucleic acid
: ( C ) STRANDEDNESS: single
: ( D ) TOPOLOGY: linear ( x i ) SEQUENCE DESCRIPTION: SEQ ID NO: 738:

CUCAGGGCUG AUGAGGCCGA AAGGCCGAAA CUCCAU 36

( 2 ) INFORMATION FOR SEQ ID NO: 739:

: ( i ) SEQUENCE CHARACTERISTICS:
: ( A ) LENGTH: 36 base pairs
: ( B ) TYPE: nucleic acid
: ( C ) STRANDEDNESS: single
: ( D ) TOPOLOGY: linear ( x i ) SEQUENCE DESCRIPTION: SEQ ID NO: 739:

CGAGUUACUG AUGAGGCCGA AAGGCCGAAA GCCUCA 36

( 2 ) INFORMATION FOR SEQ ID NO: 740:

: ( i ) SEQUENCE CHARACTERISTICS:
: ( A ) LENGTH: 36 base pairs
: ( B ) TYPE: nucleic acid
: ( C ) STRANDEDNESS: single
: ( D ) TOPOLOGY: linear ( x i ) SEQUENCE DESCRIPTION: SEQ ID NO: 740:

GGCGAGUCUG AUGAGGCCGA AAGGCCGAAA UAGCCU 36

( 2 ) INFORMATION FOR SEQ ID NO: 741:

: ( i ) SEQUENCE CHARACTERISTICS:
: ( A ) LENGTH: 36 base pairs
: ( B ) TYPE: nucleic acid
: ( C ) STRANDEDNESS: single
: ( D ) TOPOLOGY: linear ( x i ) SEQUENCE DESCRIPTION: SEQ ID NO: 741:

ACUAGGCCUG AUGAGGCCGA AAGGCCGAAA GUUAUA 36

( 2 ) INFORMATION FOR SEQ ID NO: 742:

: ( i ) SEQUENCE CHARACTERISTICS:
: ( A ) LENGTH: 36 base pairs
: ( B ) TYPE: nucleic acid
: ( C ) STRANDEDNESS: single
: ( D ) TOPOLOGY: linear ( x i ) SEQUENCE DESCRIPTION: SEQ ID NO: 742:

CUGUCACCUG AUGAGGCCGA AAGGCCGAAA GGCGAG 36

( 2 ) INFORMATION FOR SEQ ID NO: 743:

: ( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 743:

GGAGCAGCUG AUGAGGCCGA AAGGCCGAAA GCUGGG 36

(2) INFORMATION FOR SEQ ID NO: 744:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 744:

CCCAGUGCUG AUGAGGCCGA AAGGCCGAAA GCAGGA 36

(2) INFORMATION FOR SEQ ID NO: 745:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 745:

CAUUGGGCUG AUGAGGCCGA AAGGCCGAAA GCCCCG 36

(2) INFORMATION FOR SEQ ID NO: 746:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 746:

CUGAAAGCUG AUGAGGCCGA AAGGCCGAAA GGCCAU 36

(2) INFORMATION FOR SEQ ID NO: 747:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 747:

CUCCUGACUG AUGAGGCCGA AAGGCCGAAA GGAGGC 36

(2) INFORMATION FOR SEQ ID NO: 748:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 748:

UCUCCUGCUG AUGAGGCCGA AAGGCCGAAA AGGAGG 36

(2) INFORMATION FOR SEQ ID NO: 749:

(i) SEQUENCE CHARACTERISTICS:
(A) LENGTH: 36 base pairs
(B) TYPE: nucleic acid (C) STRANDEDNESS: single
                (D) TOPOLOGY: linear (xi) SEQUENCE DESCRIPTION: SEQ ID NO: 749:

AUCUCCUCUG AUGAGGCCGA AAGGCCGAAA AAGGAG      36

(2) INFORMATION FOR SEQ ID NO: 750:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO: 750:

GGAGGAGCUG AUGAGGCCGA AAGGCCGAAA GUCUUC      36

(2) INFORMATION FOR SEQ ID NO: 751:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO: 751:

UGGAGGACUG AUGAGGCCGA AAGGCCGAAA AGUCUU      36

(2) INFORMATION FOR SEQ ID NO: 752:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO: 752:

AAUGGAGCUG AUGAGGCCGA AAGGCCGAAA GAAGUC      36

(2) INFORMATION FOR SEQ ID NO: 753:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO: 753:

CGCAAUGCUG AUGAGGCCGA AAGGCCGAAA GGAGAA      36

(2) INFORMATION FOR SEQ ID NO: 754:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO: 754:

UGUCCGCCUG AUGAGGCCGA AAGGCCGAAA UGGAGG      36

(2) INFORMATION FOR SEQ ID NO: 755:

(i) SEQUENCE CHARACTERISTICS:
                (A) LENGTH: 36 base pairs
                (B) TYPE: nucleic acid
                (C) STRANDEDNESS: single
                (D) TOPOLOGY: linear ( x i ) SEQUENCE DESCRIPTION: SEQ ID NO: 755:

GGCUGAGCUG AUGAGGCCGA AAGGCCGAAA GUCCAU                36

( 2 ) INFORMATION FOR SEQ ID NO: 756:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 756:

GGGCUGACUG AUGAGGCCGA AAGGCCGAAA AGUCCA                36

( 2 ) INFORMATION FOR SEQ ID NO: 757:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 757:

CAGGGCUCUG AUGAGGCCGA AAGGCCGAAA GAAGUC                36

( 2 ) INFORMATION FOR SEQ ID NO: 758:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 758:

CUGAUCUCUG AUGAGGCCGA AAGGCCGAAA CUCAGC                36

( 2 ) INFORMATION FOR SEQ ID NO: 759:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 759:

AGGAGCUCUG AUGAGGCCGA AAGGCCGAAA UCUGAC                36

( 2 ) INFORMATION FOR SEQ ID NO: 760:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 760:

CCCUUAGCUG AUGAGGCCGA AAGGCCGAAA GCUGAU                36

( 2 ) INFORMATION FOR SEQ ID NO: 761:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 761:

```
ACCCCCUCUG  AUGAGGCCGA  AAGGCCGAAA  GGAGCU                                         36
```

( 2 ) INFORMATION FOR SEQ ID NO: 762:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 762:

```
CUCUGGGCUG  AUGAGGCCGA  AAGGCCGAAA  GGGCAG                                         36
```

( 2 ) INFORMATION FOR SEQ ID NO: 763:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 763:

```
UGAGGGGAG  AAGUUCACCA  GAGAAACACA  CGUUGUGGUA  CAUUACCUGG  UA                      52
```

( 2 ) INFORMATION FOR SEQ ID NO: 764:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 764:

```
GCUGCUUGAG  AAGCUCACCA  GAGAAACACA  CGUUGUGGUA  CAUUACCUGG  UA                     52
```

( 2 ) INFORMATION FOR SEQ ID NO: 765:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 765:

```
GCCAUCCCAG  AAGUCCACCA  GAGAAACACA  CGUUGUGGUA  CAUUACCUGG  UA                     52
```

( 2 ) INFORMATION FOR SEQ ID NO: 766:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 766:

```
GUUCUGGAAG  AAGUGGACCA  GAGAAACACA  CGUUGUGGUA  CAUUACCUGG  UA                     52
```

( 2 ) INFORMATION FOR SEQ ID NO: 767:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 767:

```
GAAGGACAAG  AAGCAGACCA  GAGAAACACA  CGUUGUGGUA  CAUUACCUGG  UA                     52
```

( 2 ) INFORMATION FOR SEQ ID NO: 768:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 768:

UUGAGCUCAG AAGUGUACCA GAGAAACACA CGUUGUGGUA CAUUACCUGG UA    52

( 2 ) INFORMATION FOR SEQ ID NO: 769:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 769:

CCCACCGAAG AAGCUGACCA GAGAAACACA CGUUGUGGUA CAUUACCUGG UA    52

( 2 ) INFORMATION FOR SEQ ID NO: 770:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 770:

AGGCUGGGAG AAGCGUACCA GAGAAACACA CGUUGUGGUA CAUUACCUGG UA    52

( 2 ) INFORMATION FOR SEQ ID NO: 771:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 771:

GGUCGGAAAG AAGCCGACCA GAGAAACACA CGUUGUGGUA CAUUACCUGG UA    52

( 2 ) INFORMATION FOR SEQ ID NO: 772:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 772:

UGACGAUCAG AAGUAUACCA GAGAAACACA CGUUGUGGUA CAUUACCUGG UA    52

( 2 ) INFORMATION FOR SEQ ID NO: 773:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 773:

GUCGGUGGAG AAGCUGACCA GAGAAACACA CGUUGUGGUA CAUUACCUGG UA    52

( 2 ) INFORMATION FOR SEQ ID NO: 774:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 774:

GGCCGGGGAG AAGUGGACCA GAGAAACACA CGUUGUGGUA CAUUACCUGG UA    52

( 2 ) INFORMATION FOR SEQ ID NO: 775:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 775:

CAUCAUCAAG AAGCAGACCA GAGAAACACA CGUUGUGGUA CAUUACCUGG UA    52

( 2 ) INFORMATION FOR SEQ ID NO: 776:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 776:

ACAGCUGGAG AAGUGCACCA GAGAAACACA CGUUGUGGUA CAUUACCUGG UA    52

( 2 ) INFORMATION FOR SEQ ID NO: 777:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 777:

GAUGCCAGAG AAGUGAACCA GAGAAACACA CGUUGUGGUA CAUUACCUGG UA    52

( 2 ) INFORMATION FOR SEQ ID NO: 778:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 778:

GAACUGUUCC CCCUCA    16

( 2 ) INFORMATION FOR SEQ ID NO: 779:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 779:

GAGCAGCCCA AGCAGC    16

( 2 ) INFORMATION FOR SEQ ID NO: 780:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 780:

GGACUGCCGG GAUGGC 16

( 2 ) INFORMATION FOR SEQ ID NO: 781:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 781:

CCACAGUUUC CAGAAC 16

( 2 ) INFORMATION FOR SEQ ID NO: 782:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 782:

CUGCCGCCUG UCCUUC 16

( 2 ) INFORMATION FOR SEQ ID NO: 783:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 783:

ACACUGCCGA GCUCAA 16

( 2 ) INFORMATION FOR SEQ ID NO: 784:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 784:

CAGCUGCCUC GGUGGG 16

( 2 ) INFORMATION FOR SEQ ID NO: 785:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 785:

ACGCAGACCC CAGCCU 16

( 2 ) INFORMATION FOR SEQ ID NO: 786:

( i ) SEQUENCE CHARACTERISTICS:
    ( A ) LENGTH: 16 base pairs ( B ) TYPE: nucleic acid
                ( C ) STRANDEDNESS: single
                ( D ) TOPOLOGY: linear ( x i ) SEQUENCE DESCRIPTION: SEQ ID NO: 786:

CGGCGGCCUU CCGACC                                                                                          16

( 2 ) INFORMATION FOR SEQ ID NO: 787:

( i ) SEQUENCE CHARACTERISTICS:
                ( A ) LENGTH: 16 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 787:

AUACAGACGA UCGUCA                                                                                          16

( 2 ) INFORMATION FOR SEQ ID NO: 788:

( i ) SEQUENCE CHARACTERISTICS:
                ( A ) LENGTH: 16 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 788:

CAGCGGACCC ACCGAC                                                                                          16

( 2 ) INFORMATION FOR SEQ ID NO: 789:

( i ) SEQUENCE CHARACTERISTICS:
                ( A ) LENGTH: 16 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 789:

CCACCGACCC CCGGCC                                                                                          16

( 2 ) INFORMATION FOR SEQ ID NO: 790:

( i ) SEQUENCE CHARACTERISTICS:
                ( A ) LENGTH: 16 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 790:

CUGCAGUUUG AUGAUG                                                                                          16

( 2 ) INFORMATION FOR SEQ ID NO: 791:

( i ) SEQUENCE CHARACTERISTICS:
                ( A ) LENGTH: 16 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 791:

GCACAGACCC AGCUGU                                                                                          16

( 2 ) INFORMATION FOR SEQ ID NO: 792:

( i ) SEQUENCE CHARACTERISTICS:
                ( A ) LENGTH: 16 base pairs
                ( B ) TYPE: nucleic acid
                ( C ) STRANDEDNESS: single ( D ) TOPOLOGY: linear ( x i ) SEQUENCE DESCRIPTION: SEQ ID NO: 792:

UCACAGACCU GGCAUC       16

( 2 ) INFORMATION FOR SEQ ID NO: 793:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 793:

GUUGCUUCAG AAGUUCACCA GAGAAACACA CGUUGUGGUA CAUUACCUGG UA       52

( 2 ) INFORMATION FOR SEQ ID NO: 794:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 794:

GAGAUUCGAG AAGUUCACCA GAGAAACACA CGUUGUGGUA CAUUACCUGG UA       52

( 2 ) INFORMATION FOR SEQ ID NO: 795:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 795:

GCCAUCCCAG AAGUCCACCA GAGAAACACA CGUUGUGGUA CAUUACCUGG UA       52

( 2 ) INFORMATION FOR SEQ ID NO: 796:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 796:

GGGCAGAGAG AAGCCUACCA GAGAAACACA CGUUGUGGUA CAUUACCUGG UA       52

( 2 ) INFORMATION FOR SEQ ID NO: 797:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 797:

UUGAGCUCAG AAGUGUACCA GAGAAACACA CGUUGUGGUA CAUUACCUGG UA       52

( 2 ) INFORMATION FOR SEQ ID NO: 798:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear 5,658,780

291

292

-continued ( x i ) SEQUENCE DESCRIPTION: SEQ ID NO: 798:

CCCACCGAAG AAGCUCACCA GAGAAACACA CGUUGUGGUA CAUUACCUGG UA    52

( 2 ) INFORMATION FOR SEQ ID NO: 799:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 799:

AGGCUGGGAG AAGCGUACCA GAGAAACACA CGUUGUGGUA CAUUACCUGG UA    52

( 2 ) INFORMATION FOR SEQ ID NO: 800:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 800:

GAUCAGAAAG AAGCCGACCA GAGAAACACA CGUUGUGGUA CAUUACCUGG UA    52

( 2 ) INFORMATION FOR SEQ ID NO: 801:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 801:

AGGUGUAGAG AAGCGGACCA GAGAAACACA CGUUGUGGUA CAUUACCUGG UA    52

( 2 ) INFORMATION FOR SEQ ID NO: 802:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 802:

GGGCAGAGAG AAGUGCACCA GAGAAACACA CGUUGUGGUA CAUUACCUGG UA    52

( 2 ) INFORMATION FOR SEQ ID NO: 803:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 803:

GGGCUUCCAG AAGCGUACCA GAGAAACACA CGUUGUGGUA CAUUACCUGG UA    52

( 2 ) INFORMATION FOR SEQ ID NO: 804:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 804:

CAGCAUCAAG AAGCAGACCA GAGAAACACA CGUUGUGGUA CAUUACCUGG UA 52

( 2 ) INFORMATION FOR SEQ ID NO: 805:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 805:

ACUCCUGGAG AAGUGCACCA GAGAAACACA CGUUGUGGUA CAUUACCUGG UA 52

( 2 ) INFORMATION FOR SEQ ID NO: 806:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 806:

GAUGCCAGAG AAGUGAACCA GAGAAACACA CGUUGUGGUA CAUUACCUGG UA 52

( 2 ) INFORMATION FOR SEQ ID NO: 807:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 807:

AAGUCGGGAG AAGCUGACCA GAGAAACACA CGUUGUGGUA CAUUACCUGG UA 52

( 2 ) INFORMATION FOR SEQ ID NO: 808:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 808:

UGGCUCCAAG AAGUCCACCA GAGAAACACA CGUUGUGGUA CAUUACCUGG UA 52

( 2 ) INFORMATION FOR SEQ ID NO: 809:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 809:

UGGUGUCGAG AAGCACACCA GAGAAACACA CGUUGUGGUA CAUUACCUGG UA 52

( 2 ) INFORMATION FOR SEQ ID NO: 810:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 810:

AUUCUGAAAG AAGCCAACCA GAGAAACACA CGUUGUGGUA CAUUACCUGG UA 52

( 2 ) INFORMATION FOR SEQ ID NO: 811:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 811:

UCAGUAAAAG AAGUCUACCA GAGAAACACA CGUUGUGGUA CAUUACCUGG UA    52

( 2 ) INFORMATION FOR SEQ ID NO: 812:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 812:

GAACAGCCGA AGCAAC    16

( 2 ) INFORMATION FOR SEQ ID NO: 813:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 813:

GAACAGUUCG AAUCUC    16

( 2 ) INFORMATION FOR SEQ ID NO: 814:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 814:

GGACUGCCGG GAUGGC    16

( 2 ) INFORMATION FOR SEQ ID NO: 815:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 815:

AGGCUGACCU CUGCCC    16

( 2 ) INFORMATION FOR SEQ ID NO: 816:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 816:

ACACUGCCGA GCUCAA    16

( 2 ) INFORMATION FOR SEQ ID NO: 817:

( i ) SEQUENCE CHARACTERISTICS:
   ( A ) LENGTH: 16 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 817:

GAGCUGCCUC GGUGGG                    16

( 2 ) INFORMATION FOR SEQ ID NO: 818:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 818:

ACGCCGACCC CAGCCU                    16

( 2 ) INFORMATION FOR SEQ ID NO: 819:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 819:

CGGCGGCCUU CUGAUC                    16

( 2 ) INFORMATION FOR SEQ ID NO: 820:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 820:

CCGCAGCCCU ACACCU                    16

( 2 ) INFORMATION FOR SEQ ID NO: 821:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 821:

GCACCGUCCU CUGCCC                    16

( 2 ) INFORMATION FOR SEQ ID NO: 822:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 822:

ACGCUGUCGG AAGCCC                    16

( 2 ) INFORMATION FOR SEQ ID NO: 823:

( i ) SEQUENCE CHARACTERISTICS:

(A) LENGTH: 16 base pairs
(B) TYPE: nucleic acid
(C) STRANDEDNESS: single
(D) TOPOLOGY: linear (xi) SEQUENCE DESCRIPTION: SEQ ID NO: 823:

CUGCAGUUUG AUGCUG                                                                         16

(2) INFORMATION FOR SEQ ID NO: 824:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO: 824:

GCACAGACCC AGGAGU                                                                         16

(2) INFORMATION FOR SEQ ID NO: 825:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO: 825:

UCACAGACCU GGCAUC                                                                         16

(2) INFORMATION FOR SEQ ID NO: 826:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO: 826:

CAGCUGCCCC CGACUU                                                                         16

(2) INFORMATION FOR SEQ ID NO: 827:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO: 827:

GGACAGACUG GAGCCA                                                                         16

(2) INFORMATION FOR SEQ ID NO: 828:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO: 828:

GUGCUGCCCG ACACCA                                                                         16

(2) INFORMATION FOR SEQ ID NO: 829:

(i) SEQUENCE CHARACTERISTICS:
(A) LENGTH: 16 base pairs
(B) TYPE: nucleic acid

```
        ( C ) STRANDEDNESS: single
        ( D ) TOPOLOGY: linear ( x i ) SEQUENCE DESCRIPTION: SEQ ID NO: 829:

UGGCCGCCUU CAGAAU                                                           16

( 2 ) INFORMATION FOR SEQ ID NO: 830:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 830:

AGACAGCCUU UACUGA                                                           16
```

REL A TARGETED RIBOZYMES

RELATED APPLICATIONS

This application is a continuation-in-part of Stinchcomb et al., "Method and Composition for Treatment of Restenosis and Cancer Using Ribozymes," filed May 18, 1994, U.S. Ser. No. 08/245,466, now abandoned, which is a continuation-in-part of Draper, "Method and Reagent for Treatment of a Stenotic Condition", filed December 7, 1992, U.S. Ser. No. 07/987,132, now abandoned, both hereby incorporated by reference herein.

FIELD OF THE INVENTION

The present invention relates to therapeutic compositions and methods for the treatment or diagnosis of diseases or conditions related to NF-κB levels, such as restenosis, rheumatoid arthritis, asthma, inflammatory or autoimmune disorders and transplant rejection.

BACKGROUND OF THE INVENTION

The following is a brief description of the physiological role of NF-κB. The discussion is not meant to be complete and is provided only for understanding of the invention that follows. This summary is not an admission that any of the work described below is prior art to the claimed invention.

The nuclear DNA-binding activity, NF-κB, was first identified as a factor that binds and activates the immunoglobulin κ light chain enhancer in B cells. NF-κB now is known to activate transcription of a variety of other cellular genes (e.g., cytokines, adhesion proteins, oncogenes and viral proteins) in response to a variety of stimuli (e.g., phorbol esters, mitogens, cytokines and oxidative stress). In addition, molecular and biochemical characterization of NF-κB has shown that the activity is due to a homodimer or heterodimer of a family of DNA binding subunits. Each subunit bears a stretch of 300 amino acids that is homologous to the oncogene, v-rel. The activity first described as NF-κB is a heterodimer of p49 or p50 with p65. The p49 and p50 subunits of NF-κB (encoded by the nf-κB2 or nf-κB1 genes, respectively) are generated from the precursors NF-κB1 (p105) or NF-κB2 (p100). The p65 subunit of NF-κB (now termed Rel A) is encoded by the rel A locus.

The roles of each specific transcription-activating complex now are being elucidated in cells (N. D. Perkins, et al., 1992 *Proc. Natl Acad. Sci U.S.A.* 89, 1529–1533). For instance, the heterodimer of NF-κB1 and Rel A (p50/p65) activates transcription of the promoter for the adhesion molecule, VCAM-1, while NF-κB2/RelA heterodimers (p49/p65) actually inhibit transcription (H. B. Shu, et al., Mol. Cell. Biol. 13, 6283–6289 (1993)). Conversely, heterodimers of NF-κB2/RelA (p49/p65) act with Tat-I to activate transcription of the HIV genome, while NF-κB1/RelA (p50/p65) heterodimers have little effect (J. Liu, N. D. Perkins, R. M. Schmid, G. J. Nabel, *J. Virol.* 1992 66, 3883–3887). Similarly, blocking rel A gene expression with antisense oligonucleotides specifically blocks embryonic stem cell adhesion; blocking NF-κB1 gene expression with antisense oligonucleotides had no effect on cellular adhesion (Narayanan et al., 1993 *Mol. Cell. Biol.* 13, 3802–3810). Thus, the promiscuous role initially assigned to NF-κB in transcriptional activation (M. J. Lenardo, D. Baltimore, 1989 *Cell* 58, 227–229) represents the sum of the activities of the rel family of DNA-binding proteins. This conclusion is supported by recent transgenic "knock-out" mice of individual members of the rel family. Such "knock-outs" show few developmental defects, suggesting that essential transcriptional activation functions can be performed by more than one member of the rel family.

A number of specific inhibitors of NF-κB function in cells exist, including treatment with phosphorothioate antisense oliogonuoleotide, treatment with double-stranded NF-κB binding sites, and over expression of the natural inhibitor MAD-3 (an IκB family member). These agents have been used to show that NF-κB is required for induction of a number of molecules involved in inflammation, as described below.

NF-κB is required for phorbol ester-mediated induction of IL-6 (I. Kitajima, et al., Science 258, 1792–5 (1992)) and IL-8 (Kunsch and Rosen, 1993 *Mol. Cell. Biol.* 13, 6137–46).

NF-κB is required for induction of the adhesion molecules ICAM-1 (Eck, et al., 1993 *Mol. Cell. Biol.* 13, 6530–6536), VCAM-1 (Shu et al., supra), and E-selectin (Read, et al., 1994 *J. Exp. Med.* 179, 503–512) on endothelial cells.

NF-κB is involved in the induction of the integrin subunit, CD18, and other adhesive properties of leukocytes (Eck et al., 1993 supra).

The above studies suggest that NF-κB is integrally involved in the induction of cytokines and adhesion molecules by inflammatory mediators. Two recent papers point to another connection between NF-κB and inflammation: glucocorticoids may exert their anti-inflammatory effects by inhibiting NF-κB. The glucocorticoid receptor and p65 both act at NF-κB binding sites in the ICAM-1 promoter (van de Stolpe, et al., 1994 *J. Biol. Chem.* 269, 6185–6192). Glucocorticoid receptor inhibits NF-κB-mediated induction of IL-6 (Ray and Prefontaine, 1994 *Proc. Natl Acad. Sci U.S.A.* 91, 752–756). Conversely, overexpression of p65 inhibits glucocorticoid induction of the mouse mammary tumor virus promoter. Finally, protein cross-linking and co-immunoprecipitation experiments demonstrated direct physical interaction between p65 and the glucocorticoid receptor (Id.).

SUMMARY OF THE INVENTION

This invention relates to ribozymes, or enzymatic RNA molecules, directed to cleave mRNA species encoding Rel A protein (p65). In particular, applicant describes the selection and function of ribozymes capable of cleaving this RNA and their use to reduce activity of NF-κB in various tissues to treat the diseases discussed herein. Such ribozymes are also useful for diagnostic applications.

Ribozymes that cleave rel A mRNA represent a novel therapeutic approach to inflammatory or autoimmune disorders. Antisense DNA molecules have been described that block NF-κB activity. See Narayanan et al., supra. However, ribozymes may show greater perdurance or lower effective doses than antisense molecules due to their catalytic properties and their inherent secondary and tertiary structures. Such ribozymes, with their catalytic activity and increased site specificity (as described below), represent more potent and safe therapeutic molecules than antisense oligonucleotides.

Applicant indicates that these ribozymes are able to inhibit the activity of NF-κB and that the catalytic activity of the ribozymes is required for their inhibitory effect. Those of ordinary skill in the art, will find that it is clear from the examples described that other ribozymes that cleave rel A encoding mRNAs may be readily designed and are within the invention.

Six basic varieties of naturally-occurring enzymatic RNAs are known presently. Each can catalyze the hydrolysis of RNA phosphodiester bonds in trans (and thus can cleave other RNA molecules) under physiological conditions. Table 1 summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf, T. M., et al., 1992, *Proc. Natl. Acad. Sci. U.S.A.*, 89, 7305-7309). Thus, the specificity of action of a ribozyme is greater than that of an antisense oligonucleotide binding the same RNA site.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al., 1992, *Aids Research and Human Retroviruses*, 8, 183, of hairpin motifs by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, 1989, *Biochemistry*, 28, 4929, and Hampel et al., 1990, *Nucleic Acids Research*, 18,299, and an example of the hepatitis delta virus motif is described by Perrotta and Been, 1992, *Biochemistry*, 31, 16, of the RNaseP motif by Guerrier-Takada et al., 1983, *Cell*, 35, 849, Neurospora VS RNA ribozyme motif is described by Collins (Saville and Collins, 1990 *Cell* 61, 685–696; Saville and Collins, 1991 *Proc. Natl. Acad. Sci. U.S.A.* 88, 8826–8830; Collins and Olive, 1993 *Biochemistry* 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

The invention provides a method for producing a class of enzymatic cleaving agents which exhibit a high degree of specificity for the RNA of a desired target. The enzymatic nucleic acid molecule is preferably targeted to a highly conserved sequence region of a target Rel A encoding mRNA such that specific treatment of a disease or condition can be provided with either one or several enzymatic nucleic acids. Such enzymatic nucleic acid molecules can be delivered exogenously to specific cells as required. Alternatively, the ribozymes can be expressed from DNA vectors that are delivered to specific cells.

Synthesis of nucleic acids greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure. However, these catalytic RNA molecules can also be expressed within cells from eukaryotic promoters (e.g., Scanlon, K. J., et al., 1991, *Proc. Natl. Acad. Sci. U.S.A.*, 88, 10591–5; Kashani-Sabet, M., et al., 1992, *Antisense Res. Dev.*, 2, 3–15; Dropulic, B., et al., 1992, *J Virol*, 66, 1432–41; Weerasinghe, M., et al., 1991, *J Virol*, 65, 5531–4; Ojwang, J. O., et al., 1992, *Proc. Natl. Acad. Sci. U.S.A.*, 89, 10802–6; Chen, C. J., et al., 1992, *Nucleic Acids Res.*, 20, 4581–9; Sarver, H., et al., 1990, *Science*, 247, 1222–1225)). Those skilled in the art realize that any ribozyme can be expressed in eukaryotic cells from the appropriate DNA vector. The activity of such ribozymes can be augmented by their release from the primary transcript by a second ribozyme (Draper et al., PCT WO93/23569, and Sullivan et al., PCT WO94/02595, both hereby incorporated in their totality by reference herein; Ohkawa, J., et al., 1992, *Nucleic Acids Symp. Ser.*, 27, 15–6; Taira, K., et al., 1991, *Nucleic Acids Res.*, 19, 5125–30; Ventura, M., et al., 1993, *Nucleic Acids Res.*, 21, 3249–55).

Inflammatory mediators such as lipopolysaccharide (LPS), interleukin-1 (IL-1) or tumor necrosis factor-a (TNF-α) act on cells by inducing transcription of a number of secondary mediators, including other cytokines and adhesion molecules. In many cases, this gene activation is known to be mediated by the transcriptional regulator, NF-κB. One subunit of NF-κB, the relA gene product (termed RelA or p65) is implicated specifically in the induction of inflammatory responses. Ribozyme therapy, due to its exquisite specificity, is particularly well-suited to target intracellular factors that contribute to disease pathology. Thus, ribozymes that cleave mRNA encoded by rel A may represent novel therapeutics for the treatment of inflammatory and autoimmune disorders.

Thus, in a first aspect, the invention features ribozymes that inhibit RelA production. These chemically or enzymatically synthesized RNA molecules contain substrate binding domains that bind to accessible regions of their target mRNAs. The RNA molecules also contain domains that catalyze the cleavage of RNA. The RNA molecules are preferably ribozymes of the hammerhead or hairpin motif. Upon binding, the ribozymes cleave the target RelA encoding mRNAs, preventing translation and p65 protein accumulation. In the absence of the expression of the target gene, a therapeutic effect may be observed.

By "inhibit" is meant that the activity or level of RelA encoding mRNA is reduced below that observed in the absense of the ribozyme, and preferably is below that level observed in the presence of an inactive RNA molecule able to bind to the same site on the mRNA, but unable to cleave that RNA.

Such ribozymes are useful for the prevention of the diseases and conditions discussed above, and any other diseases or conditions that are related to the level of NF-κB activity in a cell or tissue. By "related" is meant that the inhibition of relA mRNA and thus reduction in the level of NF-κB activity will relieve to some extent the symptoms of the disease or condition.

Ribozymes are added directly, or can be complexed with cationic lipids, packaged within liposomes, or otherwise delivered to target cells. The RNA or RNA complexes can be locally administered to relevant tissues ex vivo, or in vivo through injection or the use of a catheter, infusion pump or stent, with or without their incorporation in biopolymers. In preferred embodiments, the ribozymes have binding arms which are complementary to the sequences in Tables II, III, VI–VII. Examples of such ribozymes are shown in Tables IV–VII. Examples of such ribozymes consist essentially of sequences defined in these Tables. By "consists essentially of" is meant that the active ribozyme contains an enzymatic center equivalent to those in the examples, and binding arms able to bind mRNA such that cleavage at the target site occurs. Other sequences may be present which do not interfere with such cleavage.

In another aspect of the invention, ribozymes that cleave target molecules and inhibit NF-κB activity are expressed from transcription units inserted into DNA, RNA, or viral vectors. Preferably, the recombinant vectors capable of expressing the ribozymes are locally delivered as described above, and transiently persist in target cells. Once expressed, the ribozymes cleave the target mRNA. The recombinant vectors are preferably DNA plasmids or adenovirus vectors. However, other mammalian cell vectors that direct the expression of RNA may be used for this purpose.

Other features and advantages of the invention will be apparent from the following description of the preferred embodiments thereof, and from the claims.

DESCRIPTION OF THE PREFERRED EMBODIMENTS

The drawings will first briefly be described.

Drawings FIG. 1 is a diagrammatic representation of the hammerhead ribozyme domain known in the art.

FIG. 2a is a diagrammatic representation of the hammerhead ribozyme domain known in the art; FIG. 2b is a diagrammatic representation of the hammerhead ribozyme as divided by Uhlenbeck (1987,*Nature*, 327, 596–600) into a substrate and enzyme portion; FIG. 2c is a similar diagram showing the hammerhead divided by Haseloff and Gerlach (1988, Nature, 334, 585–591) into two portions; and FIG. 2d is a similar diagram showing the hammerhead divided by Jeffries and Symons (1989, *Nucl. Acids. Res.*, 17, 1371–1371) into two portions.

Figure 6B:
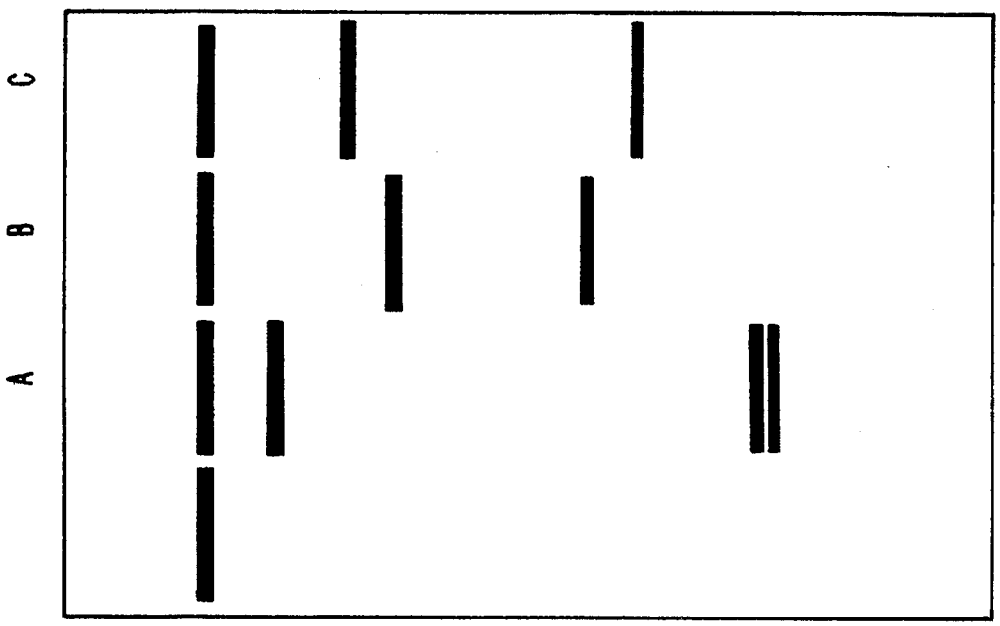
Figure 6A:
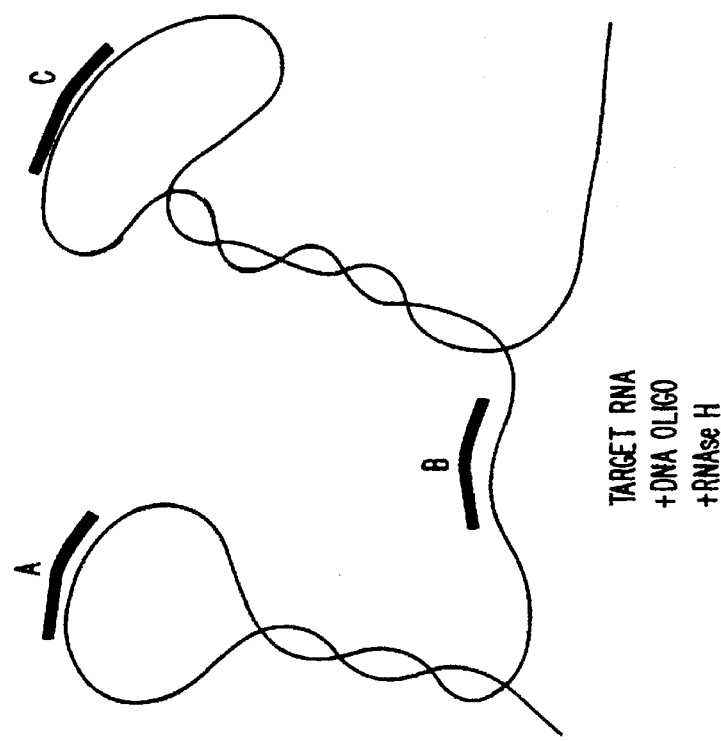

FIG. 6 is a schematic representation of an RNAseH accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

Ribozymes

Ribozymes of this invention block to some extent NF-κB expression and can be used to treat disease or diagnose such disease. Ribozymes will be delivered to cells in culture and to cells or tissues in animal models of restenosis, transplant rejection and rheumatoid arthritis. Ribozyme cleavage of re/A mRNA in these systems may prevent inflammatory cell function and alleviate disease symptoms.

Target Sites

Targets for useful ribozymes can be determined as disclosed in Draper et al supra, Sullivan et al., supra, as well as by Draper et al., "Method and reagent for treatment of arthritic conditions" U.S. Ser. No. 08/152,487, filed Nov. 12, 1993, and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described. Such ribozymes can also be optimized and delivered as described therein. While specific examples to mouse and human RNA are provided, those in the art will recognize that the equivalent human RNA targets described can be used as described below. Thus, the same target may be used, but binding arms suitable for targeting human RNA sequences are present in the ribozyme. Such targets may also be selected as described below.

The sequence of human and mouse relA mRNA can be screened for accessible sites using a computer folding algorithm. Potential hammerhead or hairpin ribozyme cleavage sites were identified. These sites are shown in Tables II, III, and VI–VII. (All sequences are 5' to 3' in the tables.) While mouse and human sequences can be screened and ribozymes thereafter designed, the human targetted sequences are of most utility. However, as discussed in Stinchcomb et al. supra, mouse targetted ribozmes are useful to test efficacy of action of the ribozyme prior to testing in humans. The nucleotide base position is noted in the Tables as that site to be cleaved by the designated type of ribozyme. (In Table II, lower case letters indicate positions that are not conserved between the Human and the Mouse rel A sequences.)

Hammerhead ribozymes are designed that could bind and are individually analyzed by computer folding (Jaeger, J. A., et al., 1989, *Proc. Natl. Acad. Sci. U.S.A.*, 86, 7706–7710) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

Referring to FIG. 6, mRNA is screened for accessible cleavage sites by the method described generally in Draper et al., WO/US93/04020 hereby incorporated by reference herein. Briefly, DNA oligonucleotides representing potential hammerhead ribozyme cleavage sites are synthesized. A polymerase chain reaction is used to generate a substrate for T7 RNA polymerase transcription from human or murine rel A cDNA clones. Labeled RNA transcripts are synthesized in vitro from the two templates. The oligonucleotides and the labeled transcripts are annealed, RNAseH is added and the mixtures are incubated for the designated times at 37° C. Reactions are stopped and RNA separated on sequencing polyacrylamide gels. The percentage of the substrate cleaved is determined by autoradiographic quantitation using a phosphor imaging system. From these data, hammerhead ribozyme sites are chosen as the most accessible.

Ribozymes of the hammerhead motif are designed to anneal to various sites in the mRNA message. The binding arms are complementary to the target site sequences described above. The ribozymes are chemically synthesized. The method of synthesis used follows the procedure for normal RNA synthesis as described in Usman, N.; Ogilvie, K. K.; Jiang, M.-Y.; Cedergren, R. J. 1987, *J. Am. Chem. Soc.*, 109, 7845–7854 and in Scaringe, S. A.; Franklyn, C.; Usman, N., 1990, *Nucleic Acids Res.*, 18, 5433–5441 and makes use of common nucleic acid protecting and coupling groups, such as dimethoxytrityl at the 5'-end, and phosphoramidites at the 3'-end. The average stepwise coupling yields were >98%. Inactive ribozymes were synthesized by substituting a U for $G_5$ and a U for $A_{14}$ (numbering from (Hertel, K. J., et al., 1992, *Nucleic Acids Res.*, 20, 3252)). Hairpin dbozymes are synthesized in two parts and annealed to reconstruct the active ribozyme (Chowrira, B. M. and Burke, J. M., 1992, *Nucleic Acids Res.*, 20, 2835–2840). All ribozymes are modified to enhance stability by modification of five ribonucleotides at both the 5' and 3' ends with 2'-O-methyl groups. Ribozymes are purified by gel electrophoresis using general methods or are purified by high pressure liquid chromatography (HPLC; See Usman et al., Synthesis, deprotection, analysis and purification of RNA and ribozymes, filed May, 18, 1994, U.S. Ser. No. 08/245, 736 the totality of which is hereby incorporated herein by reference.) and are resuspended in water.

The sequences of the chemically synthesized ribozymes useful in this study are shown in Tables IV–VII. Those in the art will recognize that these sequences are representative only of many more such sequences where the enzymatic portion of the ribozyme (all but the binding arms) is altered to affect activity and may be formed of ribonucleotides or other nucleotides or non-nucleotides. Such ribozymes are equivalent to the ribozymes described specifically in the Tables.

Optimizing Ribozyme Activity

Figure 2B:
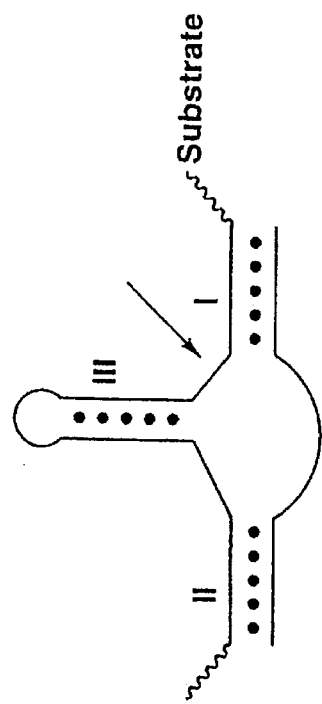
Figure 2D:
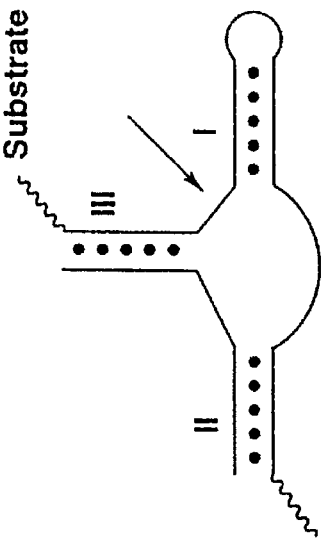
Figure 2A:
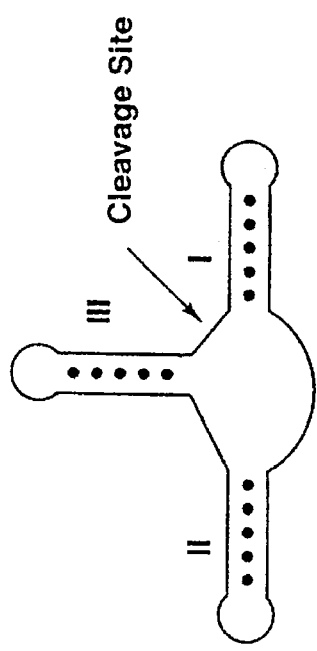
Figure 2C:
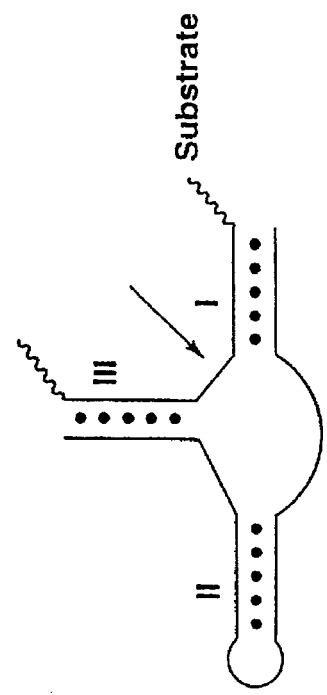

Ribozyme activity can be optimized as described by Stinchcomb et al., supra. The details will not be repeated here, but include altering the length of the ribozyme binding arms (stems I and III, see FIG. 2c), or chemically synthesizing ribozymes with modifications that prevent their degradation by serum ribonucleases (see e.g., Eckstein et al., International Publication No. WO 92/07065; Perrault et aL, Nature 1990, 344:565; Pieken et al., Science 1991, 253:314; Usman and Cedergren, *Trends in Biochem. Sci.* 1992, 17:334; Usman et al., International Publication No. WO 93/15187; and Rossi et aL, International Publication No. WO 91/03162, as well as Usman, N. et al. U.S. patent application No. 07/829,729, and Sproat, B. European Patent Application 92110298.4 which describe various chemical modifications that can be made to the sugar moieties of enzymatic RNA molecules. All these publications are hereby incorporated by reference herein.), modifications which enhance their efficacy in cells, and removal of stem II bases to shorten RNA synthesis times and reduce chemical requirements.

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intrvascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan, et al., supra and Draper, et al., supra which have been incorporated by reference herein.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein, O. and Moss, B., 1990, *Proc. Natl. Acad. Sci. U.S.A.*, 87, 6743–7; Gao, X. and Huang, L., 1993, *Nucleic Acids Res.*, 21, 2867–72; Lieber, A., et al., 1993, *Methods Enzymol.*, 217, 47–66; Zhou, Y., et al., 1990, *Mol. Cell. Biol.*, 10, 4529–37). Several investigators have demonstrated that ribozymes expressed from such promoters can function in mammalian cells (e.g. (Kashani-Sabet, M., et al., 1992, *Antisense Res. Dev.*, 2, 3–15; Ojwang, J. O., et al., 1992, *Proc. Natl. Acad. Sci. U.S.A.*, 89, 10802–6; Chen, C. J., et al., 1992, *Nucleic Acids Res.*, 20, 4581–9; Yu, M., et al., 1993, *Proc. Natl. Acad. Sci. U.S.A.*, 90, 6340–4; L'Huillier, P. J., et al., 1992, *Embo J.*, 11, 4411–8; Lisziewicz, J., et al., 1993, *Proc. Natl. Acad. Sci. U.S.A.*, 90, 8000–4)). The above ribozyme transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral vectors).

In a preferred embodiment of the invention, a transcription unit expressing a ribozyme that cleaves relA RNA is inserted into a plasmid DNA vector or an adenovirus DNA viral vector. Both vectors have been used to transfer genes to the intact vasculature or to joints of live animals (Willard, J. E., et al., 1992, *Circulation*, 86, 1–473.; Nabel, E. G., et al., 1990, *Science.*, 249, 1285–1288.) and both vectors lead to transient gene expression. The adenovirus vector is delivered as recombinant adenoviral particles. DNA may be delivered alone or complexed with vehicles (as described for RNA above). The DNA, DNA vehicle complexes, or the recombinant adenovirus particles are locally administered to the site of treatment, e.g., through the use of an injection catheter, stent or infusion pump or are directly added to cells or tissues ex vivo.

Example 1: NF-κB Hammerhead Ribozymes

By engineering ribozyme motifs we have designed several ribozymes directed against rel A mRNA sequences.

These ribozymes are synthesized with modifications that improve their nuclease resistance. The ability of ribozymes to cleave relA target sequences in vitro is evaluated.

The ribozymes will be tested for function in vivo by analyzing cytokine-induced VCAM-1, ICAM-1, IL-6 and IL-8 expression levels. Ribozymes will be delivered to cells by incorporation into liposomes, by complexing with cationic lipids, by microinjection, or by expression from DNA vectors. Cytokine-induced VCAM-1, ICAM-1, IL-6 and IL-8 expression will be monitored by ELISA, by indirect immunofluoresence, and/or by FACS analysis. Rel A mRNA levels will be assessed by Northern analysis, RNAse protection or primer extension analysis or quantitative RT-PCR. Activity of NF-κB will be monitored by gel-retardation assays. Ribozymes that block the induction of NF-κB activity and/or relA mRNA by more than 50% will be identified.

RNA ribozymes and/or genes encoding them will be locally delivered to transplant tissue ex vivo in animal models. Expression of the ribozyme will be monitored by its ability to block ex vivo induction of VCAM-1, ICAM-1, IL-6 and IL-8 mRNA and protein. The effect of the anti-rel A ribozymes on graft rejection will then be assessed. Similarly, ribozymes will be introduced into joints of mice with collagen-induced arthritis or rabbits with Streptococcal cell wall-induced arthritis. Liposome delivery, cationic lipid delivery, or adeno-associated virus vector delivery can be used. One dose (or a few infrequent doses) of a stable anti-relA ribozyme or a gene construct that constitutively expresses the ribozyme may abrogate inflammatory and immune responses in these diseases.

Uses

A therapeutic agent that inhibits cytokine gene expression, inhibits adhesion molecule expression, and mimics the anti-inflammatory effects of glucocorticoids (without inducing steroid-responsive genes) is ideal for the treatment of inflammatory and autoimmune disorders. Disease targets for such a drug are numerous. Target indications and the delivery options each entails are summarized below. In all cases, because of the potential immunosuppressive properties of a ribozyme that cleaves rel A mRNA, uses are limited to local delivery, acute indications, or ex vivo treatment.

Rheumatoid Arthritis (RA)

Due to the chronic nature of RA, a gene therapy approach is logical. Delivery of a ribozyme to inflamed joints is mediated by adenovirus, retrovirus, or adeno-associated virus vectors. For instance, the appropriate adenovirus vector can be administered by direct injection into the synovium: high efficiency of gene transfer and expression for several months would be expected (B. J. Roessler, E. D. Allen, J. M. Wilson, J. W. Hartman, B. L. Davidson, J. Clin. Invest. 92, 1085–1092 (1993)). It is unlikely that the course of the disease could be reversed by the transient, local administration of an anti-inflammatory agent. Multiple administrations may be necessary. Retrovirus and adeno-associated virus vectors would lead to permanent gene transfer and expression in the joint. However, permanent expression of a potent anti-inflammatory agent may lead to local immune deficiency.

Restenosis

Expression of NF-κB in the vessel wall of pigs causes a narrowing of the luminal space due to excessive deposition of extracellular matrix components. This phenotype is similar to matrix deposition that occurs subsequent to coronary angioplasty. In addition, NF-κB is required for the expression of the oncogene c-myb (F. A. La Rosa, J. W. Pierce, G. E. Soneneshein, Mol. Cell. Biol. 14, 1039–44 (1994)). Thus NF-κB induces smooth muscle proliferation and the expression of excess matrix components: both processes are thought to contribute to reocclusion of vessels after coronary angioplasty.

Transplantation

NF-κB is required for the induction of adhesion molecules (Eck et al., supra, K. O'Brien, et al., J. Clin. Invest. 92, 945–951 (1993)) that function in immune recognition and inflammatory responses. At least two potential modes of treatment are possible. In the first, transplanted organs are treated ex vivo with ribozymes or ribozyme expression vectors. Transient inhibition of NF-κB in the transplanted endothelium may be sufficient to prevent transplant-associated vasculitis and may significantly modulate graft rejection. In the second, donor B cells are treated ex vivo with ribozymes or ribozyme expression vectors. Recipients would receive the treatment prior to transplant. Treatment of a recipient with B cells that do not express T cell co-stimulatory molecules (such as ICAM-1, VCAM-1, and/ or B7 an B7-2) can induce antigen-specific anergy. Tolerance to the donor's histocompatibility antigens could result; potentially, any donor could be used for any transplantation procedure.

Asthma

Granulocyte macrophage colony stimulating factor (GM-CSF) is thought to play a major role in recruitment of eosinophils and other inflammatory cells during the late phase reaction to asthmatic trauma. Again, blocking the local induction of GM-CSF and other inflammatory mediators is likely to reduce the persistent inflammation observed in chronic asthmatics. Aerosol delivery of ribozymes or adenovirus ribozyme expression vectors is a feasible treatment.

Gene Therapy

Immune responses limit the efficacy of many gene transfer techniques. Cells transfected with retrovirus vectors have short lifetimes in immune competent individuals. The length of expression of adenovirus vectors in terminally differentiated cells is longer in neonatal or immune-compromised animals. Insertion of a small ribozyme expression cassette that modulates inflammatory and immune responses into existing adenovirus or retrovirus constructs will greatly enhance their potential.

Thus, ribozymes of the present invention that cleave rel A mRNA and thereby NF-κB activity have many potential therapeutic uses, and there are reasonable modes of delivering the ribozymes in a number of the possible indications. Development of an effective ribozyme that inhibits NF-κB function is described above; available cellular and activity assays are number, reproducible, and accurate. Animal models for NF-κB function (Kitajima, et al., supra) and for each of the suggested disease targets exist and can be used to optimize activity.

Diagnostic Uses

Ribozymes of this invention may be used as diagnostic tools to examine genetic drift and mutations within diseased cells. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNA associated with an NF-κB related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., NF-κB) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

TABLE I

Characteristics of Ribozymes

Group I Introns

Size: ~200 to >1000 nucleotides.
Requires a U in the target sequence immediately 5' of the cleavage site.
Binds 4–6 nucleotides at 5' side of cleavage site.
Over 75 known members of this class. Found in *Tetrahymena*

TABLE I-continued

Characteristics of Ribozymes

*thermophila* rRNA, fungal mitochondria, chloroplasts, phage T4, blue-green algae, and others, RNAseP RNA (M1 RNA)

Size: ~290 to 400 nucleotides.
RNA portion of a ribonucleoprotein enzyme. Cleaves tRNA precursors to form mature tRNA.
Roughly 10 known members of this group all are bacterial in origin.

Hammerhead Ribozyme

Figure 1:
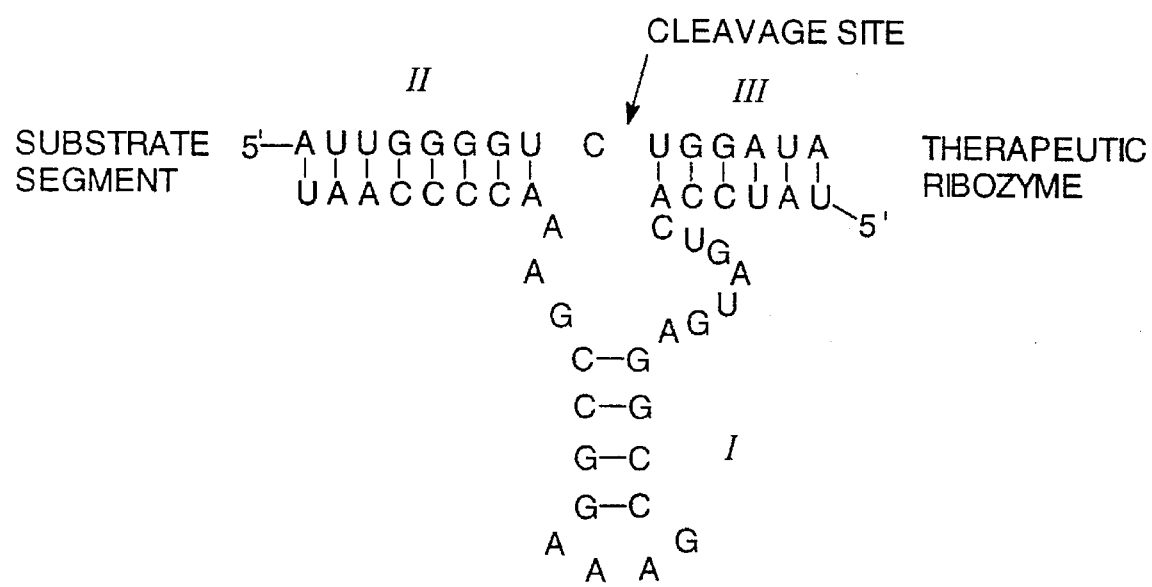

Size: ~13 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (FIGS. 1 and 2 show examples of various manifestations as used in the art).

Hairpin Ribozyme

Figure 3:
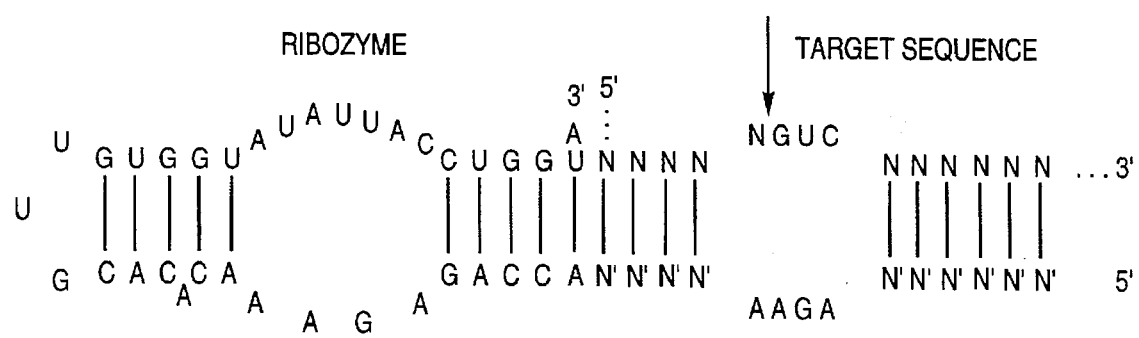
FIG. 3 is a representation of the general structure of the hairpin ribozyme domain known in the art.

Size: ~50 nucleotides.
Requires the target sequence GUC immediately 3' of the cleavage site.
Binds 4–6 nucleotides at 5' side of the cleavage site and a variable number to the 3' side of the cleavage site.
Only 3 known members of this class. Found in three plant pathogen (satellite RNAs of the tobacco (ringspot virus, arabis mosaic virus and chicory yellow mottle virus) which uses RNA as the infectious agent (FIG. 3).

Hepatitis Delta Virus (HDV) Ribozyme

Figure 4:
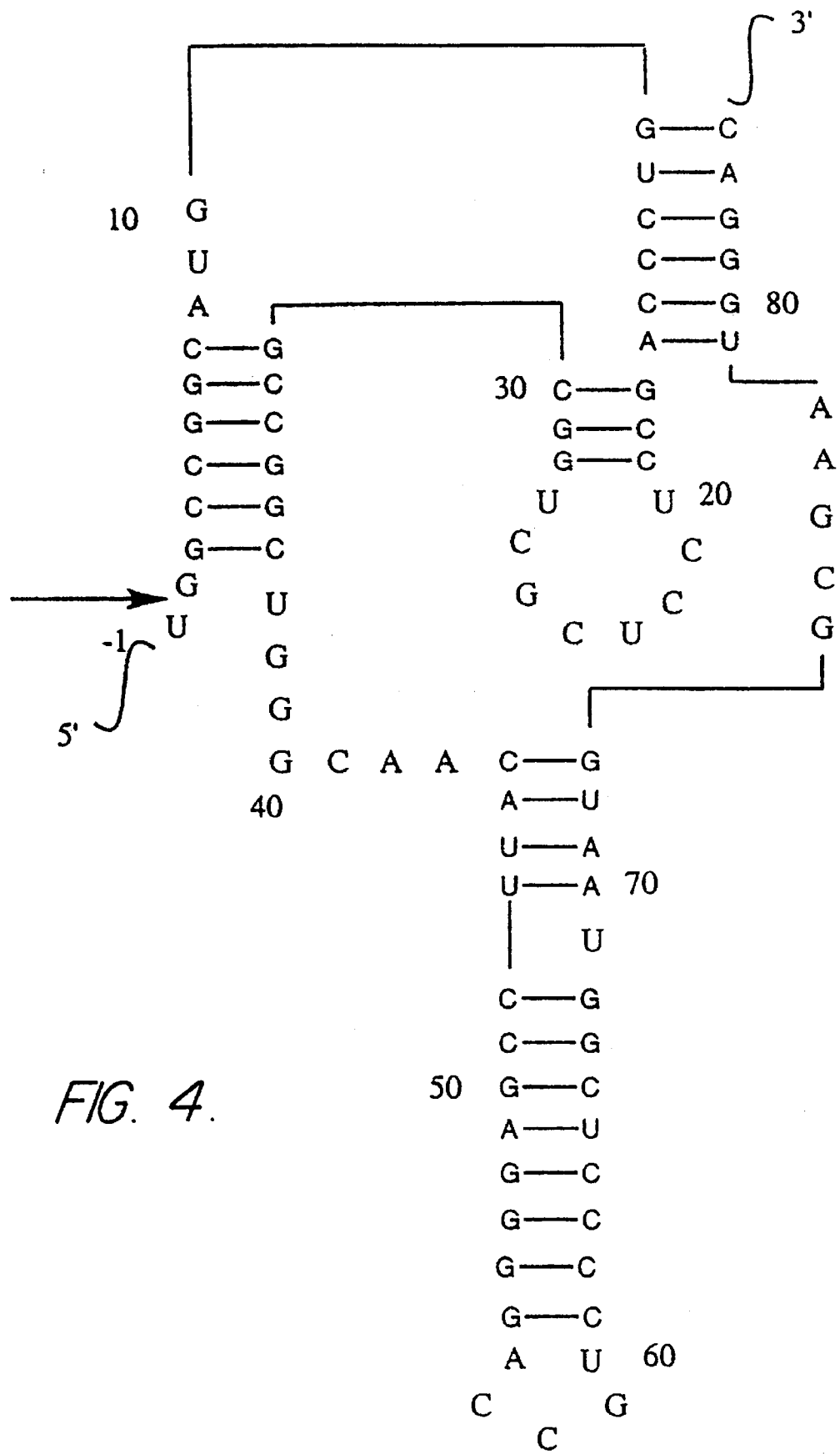
FIG. 4 is a representation of the general structure of the hepatitis delta virus ribozyme domain known in the art.

Size: 50–60 nucleotides (at present).
Cleavage of target RNAs recently demonstrated.
Sequence requirements not fully determined.
Binding sites and structural requirements not fully determined, although no sequences 5' of cleavage site are required.
Only 1 known member of this class. Found in human HDV (FIG. 4).

Neurospora VS RNA Ribozyme

Figure 5:
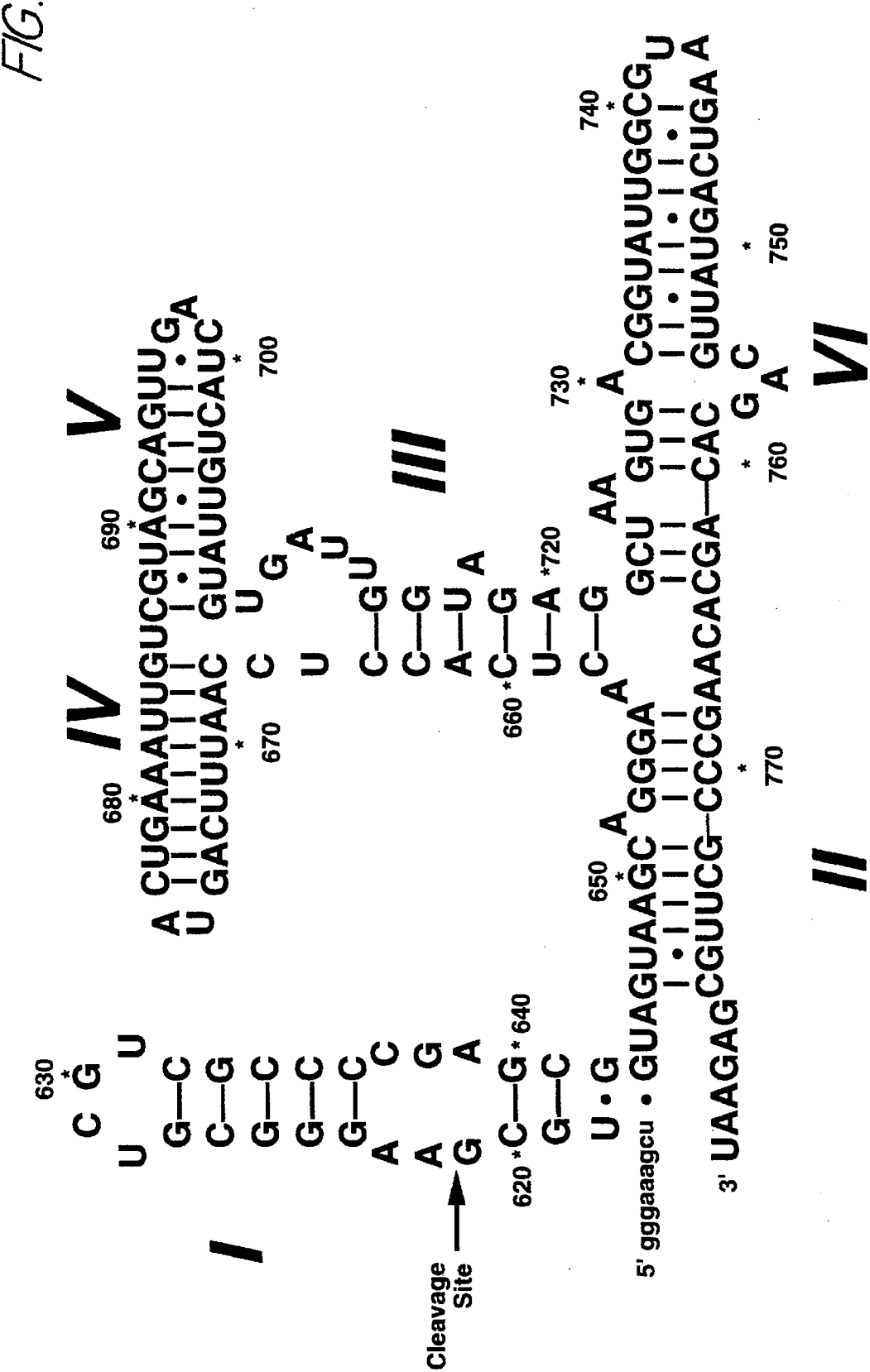
FIG. 5 is a representation of the general structure of the VS RNA ribozyme domain known in the art.

Size: ~144 nucleotides (at present)
Cleavage of target RNAs resently demonstrated.
Sequence requirements not fully determined.
Binding sites and structural requirements not fully determined. Only 1 known member of this class. Found in Neurospora VS RNA (FIG. 5).

TABLE II

Mouse rel A HH Target sequence

| nt. Pos. | HH Target Sequence | Seq. ID No. | nt. Pos. | HH Target Sequence | Seq. ID No. |
| --- | --- | --- | --- | --- | --- |
| 19 | AAUGGCU a caCaGgA | 7 | 467 | cCAGGCU c cuguUCg | 108 |
| 22 | aGCUCcU a cGUgGUG | 8 | 469 | AaGCcAU u AGcCAGC | 109 |
| 26 | CuUCCaU u GcGgACa | 9 | 473 | UuUgAGU C AGauCAg | 110 |
| 93 | GAuCUGU U uCCCCUC | 10 | 481 | AGCGaAU C CAGACCA | 111 |
| 94 | AuCUGUU u CCCCUCA | 11 | 501 | AACCCCU U uCAcGUU | 112 |
| 100 | UuCCCCU C AUCUUuC | 12 | 502 | ACCCCUU u CAcGUUC | 113 |
| 103 | CCCUCAU C UuuCCcu | 13 | 508 | UuCAcGU U CCUAUAG | 114 |
| 105 | CUCAUCU U uCCcuCA | 14 | 509 | uCAcGUU C CUAUAGA | 115 |
| 106 | UCAUCUU u CccuCAG | 15 | 512 | cGUUCCU A UAGAgGA | 116 |
| 129 | CAGGCuU C UGGgCCu | 16 | 514 | UUCCUAU A GAgGAGC | 117 |
| 138 | GGgCCuU A UGUGGAG | 17 | 534 | GGGGACU A uGACuUG | 118 |
| 148 | UGGAGAU C AucGAaC | 18 | 556 | UGCGcCU C UGCUUCC | 119 |
| 151 | AGAUCAU c GaaCAGC | 19 | 561 | CUCUGCU U CCAGGUG | 120 |
| 180 | AUGCGaU U CCGCUAu | 20 | 562 | UCUGCUU C CAGGUGA | 121 |
| 181 | UGCGaUU C CGCUAuA | 21 | 585 | aAgCCAU u AGcCAGc | 122 |
| 186 | UUCCGCU A uAAaUGC | 22 | 598 | GGCCCCU C CuCCUGa | 123 |
| 204 | GGGCGCU C aGCGGGC | 23 | 613 | CcCCUGU C CUcuCaC | 124 |
| 217 | GCAGuAU u CcuGGCG | 24 | 616 | CUGUCCU c uCaCAUC | 125 |
| 239 | CACAGAU A CCACCAA | 25 | 617 | gucCCUU C CUCAgCC | 126 |
| 262 | CCACCAU C AAGAUCA | 26 | 620 | CCUUCCU C AgCCaug | 127 |
| 268 | UCAAGAU C AAUGGCU | 27 | 623 | UCCUgcU u CCAUCUc | 128 |
| 276 | AAUGGCU A CACAGGA | 28 | 628 | AUCCgAU u UUUGAuA | 129 |
| 301 | UuCGaAU C UCCCUGG | 29 | 630 | CCgAUuU U UGAuAAc | 130 |
| 303 | CGaAUCU C CCUGGUC | 30 | 631 | CgAUuUU U GAuAAcC | 131 |
| 310 | CCCUGGU C ACCAAGG | 31 | 638 | UGgCcAU u GUGuuCC | 132 |
| 323 | GGcCCCU C CUCcuga | 32 | 661 | CCGAGCU C AAGAUCU | 133 |
| 326 | uCCaCCU C ACCGGCC | 33 | 667 | UCAAGAU C UGCCGAG | 134 |
| 335 | CCGGCCU C AuCCaCA | 34 | 687 | CGgAACU C UGGgAGC | 135 |
| 349 | AuGAaCU U GugGGgA | 35 | 700 | GCUGCCU C GGUGGGG | 136 |
| 352 | AGaUcaU c GaAcAGc | 36 | 715 | AUGAGAU C UUCUuGC | 137 |
| 375 | GAUGGCU a CUAUGAG | 37 | 717 | GAGAUCU U CuUgCUG | 138 |
| 376 | AUGGucU C UccGgaG | 38 | 718 | AGAUCUU C uUgCUGU | 139 |
| 378 | GGCUaCU A UGAGGCU | 39 | 721 | UucUCCU c CauUGcG | 140 |
| 391 | CUGAcCU C UGCCCaG | 40 | 751 | AaGACAU U GAGGUGU | 141 |
| 409 | GCaGuAU C CauAGcU | 41 | 759 | GAGGUGU A UUUCACG | 142 |
| 416 | CCgCAGU a UCCAuAg | 42 | 761 | GGUGUAU U UCACGGG | 143 |
| 417 | CAuAGcU U CCAGAAC | 43 | 762 | GUGUAUU U CACGGGA | 144 |
| 418 | AuAGcUU C CAGAACC | 44 | 763 | UGUAUUU C ACGGGAC | 145 |
| 433 | UGGGgAU C CAGUGUG | 45 | 792 | CGAGGCU C CUUUUCu | 146 |
| 795 | GGCUCCU U UUCuCAA | 46 | 1167 | GAUGAGU U UuCCcCC | 147 |
| 796 | GCUCCUU U UcuCAAG | 47 | 1168 | AUGAGUU U uCCcCCA | 148 |
| 797 | CUCCUUU U CuCAAGC | 48 | 1169 | UGAGUUU u CCcCCAU | 149 |
| 798 | UCCUUUU C uCAAGCU | 49 | 1182 | AUGcUGU U aCCaUCa | 150 |
| 829 | UGGCCAU U GUGUUCC | 50 | 1183 | UGcUGUU a CCaUCaG | 151 |
| 834 | AUUGUGU U CCGGACu | 51 | 1184 | GGccccU C CUcCUGa | 152 |
| 835 | UUGUGUU C CGGACuC | 52 | 1187 | GUccCuU c CUcaGCc | 153 |
| 845 | GACuCCU C CgUACGC | 53 | 1188 | UUaCCaU C aGGGCAG | 154 |
| 849 | CCUCCgU A CGCcGAC | 54 | 1198 | GGgAGuU u AGuCuGa | 155 |
| 872 | cCAGGCU C CUGUuCG | 55 | 1209 | CAGcCCU a caCCUUc | 156 |
| 883 | UuCGaGU C UCCAUGC | 56 | 1215 | cuGGCCU u aGCaCCG | 157 |
| 885 | CGaGUCU C CAUGCAG | 57 | 1229 | GGuCCCU u CCucAGc | 158 |
| 905 | GCGGCCU U CuGAuCG | 58 | 1237 | CCCAgcU C CUGCCCC | 159 |
| 906 | CGGCCUU C uGAuCGc | 59 | 1250 | CCAGcCU C CAGgCuC | 160 |
| 919 | GcGAGCU C AGUGAGC | 60 | 1268 | CCCaGCU C CuGCCcc | 161 |
| 936 | AUGGAgU U CCAGUAC | 61 | 1279 | CCAUGGU c cCuuCcu | 162 |
| 937 | UGGAgUU C CAGUACu | 62 | 1281 | gUGGgcU C AGCUgcG | 163 |
| 942 | UUCCAGU A CuUGCCA | 63 | 1286 | AUgAGuU U UccCCCA | 164 |
| 953 | GCCucAU c CacAuGA | 64 | 1309 | CuCCUGU u CgAGUCu | 165 |
| 962 | AGAuGAU C GcCACCG | 65 | 1315 | cCCCAGU u CUAaCCC | 166 |
| 965 | CagUacU u gCCaGAc | 66 | 1318 | CAGUuCU A aCCCCgG | 167 |
| 973 | ACCGGAU U GaaGAGA | 67 | 1331 | gGGuCCU C cCCAguC | 168 |
| 986 | GAgACCU u cAAGagu | 68 | 1334 | CuuUucU C AaGCUGa | 169 |
| 996 | AGGACcU A UGAGACC | 69 | 1389 | ACGCUGU C gGAaGCC | 170 |
| 1005 | GAGACCU U CAAGAGu | 70 | 1413 | CUGCAGU U UGAUGcU | 171 |
| 1006 | AGACCUU C AAGAGuA | 71 | 1414 | UGCAGUU U GAUGcUG | 172 |
| 1015 | AGAGuAU C AUGAAGA | 72 | 1437 | GGGGCCU U GCUUGGC | 173 |
| 1028 | GAAGAGU C CUUUCAa | 73 | 1441 | CCUUGCU U GGCAACA | 174 |
| 1031 | GAGUCCU U UCAauGG | 74 | 1467 | GgaGUGU U CACAGAC | 175 |
| 1032 | AGUCCUU U CaauGGA | 75 | 1468 | gaGUGUU C ACAGACC | 176 |
| 1033 | GUCCUUU C AauGGAC | 76 | 1482 | CUGGCAU C uGUgGAC | 177 |
| 1058 | CCGGCCU C CaaCcCG | 77 | 1486 | CuUCgGU a GggAACU | 178 |
| 1064 | UaCACCU u GaucCAa | 78 | 1494 | GACAACU C aGAGUUU | 179 |
| 1072 | GgCGuAU U GCUGUGC | 79 | 1500 | UCaGAGU U UCAGCAG | 180 |
| 1082 | UGUGCCU a CCCGaAa | 80 | 1501 | CaGAGUU U CAGCAGC | 181 |

TABLE II-continued

Mouse rel A HH Target sequence

| nt. Pos. | HH Target Sequence | Seq. ID No. | nt. Pos. | HH Target Sequence | Seq. ID No. |
|---|---|---|---|---|---|
| 1083 | aaGCCUU C CCGaAGu | 81 | 1502 | aGAGUUU C AGCAGCU | 182 |
| 1092 | CGaAaCU U AaCUUCU | 82 | 1525 | gGuGCAU c CCUGUGu | 183 |
| 1097 | CUCAaCU U CUGUCCC | 83 | 1566 | AUGGAGU A CCCUGAa | 184 |
| 1098 | UCAaCUU C UGUCCCC | 84 | 1577 | UGAaGCU A UAACUCG | 185 |
| 1102 | CUUCUGU C CCCAAGC | 85 | 1579 | AaGCUAU A ACUCGCC | 186 |
| 1125 | CAGCCCU A caCCUUc | 86 | 1583 | UAUAACU C GCCUgGU | 187 |
| 1127 | GCCaUAU a gCcUUAC | 87 | 1588 | CUCuCCU A GaGAggG | 188 |
| 1131 | cAUCCCU c agCacCA | 88 | 1622 | CCCAGCU C CUGCcCC | 189 |
| 1132 | AcaCCUU c cCagCAU | 89 | 1628 | UCCUGCU u CggUaGG | 190 |
| 1133 | UCCaUcU c CagCuUC | 90 | 1648 | CGGGGCU u CCCAAUG | 191 |
| 1137 | UUUACuU u AgCgCgc | 91 | 1660 | cUGaCCU C ugccCAG | 192 |
| 1140 | cCagCAU C CCUcAGC | 92 | 1663 | cuCUgCU U cCAGGuG | 193 |
| 1153 | GCACCAU C AACUuUG | 93 | 1664 | uCUgCUU c CAGGuGA | 194 |
| 1158 | AUCAACU u UGAUGAG | 94 | 1665 | CUCgcUU U cGGAGgU | 195 |
| 1680 | GAAGACU U CUCCUCC | 95 | | | |
| 1681 | AAGACUU C UCCUCCA | 96 | | | |
| 1683 | GACUUCU C CUCCAUU | 97 | | | |
| 1686 | UUCUCCU C CAUUGCG | 98 | | | |
| 1690 | CCUCCAU U GCGGACA | 99 | | | |
| 1704 | AUGGACU U CUCuGCu | 100 | | | |
| 1705 | UGGACUU C UCuGCuC | 101 | | | |
| 1707 | GACUUCU C uGCuCUu | 102 | | | |
| 1721 | uuUGAGU C AGAUCAG | 103 | | | |
| 1726 | GUCAGAU C AGCUCCU | 104 | | | |
| 1731 | AUCAGCU C CUAAGGu | 105 | | | |
| 1734 | AGCUCCU A AGGuGcU | 106 | | | |
| 1754 | CaGugCU C CCaAGAG | 107 | | | |

TABLE III

Human rel A HH Target Sequences

| nt. Pos. | HH Target Sequence | Seq. ID No. | nt. Pos. | HH Target Sequence | Seq. ID No. |
|---|---|---|---|---|---|
| 19 | AAUGGCU C GUCUGUA | 196 | 467 | GCAGGCU A UCAGUCA | 297 |
| 22 | GGCUCGU C UGUAGUG | 197 | 469 | AGGCUAU C AGUCAGC | 298 |
| 26 | CGUCUGU A GUGCACG | 198 | 473 | UAUCAGU C AGCGCAU | 299 |
| 93 | GAACUGU U CCCCCUC | 199 | 481 | AGCGCAU C CAGACCA | 300 |
| 94 | AACUGUU C CCCCUCA | 200 | 501 | AACCCCU U CCAAGUU | 301 |
| 100 | UCCCCCU C AUCUUCC | 201 | 502 | ACCCCUU C CAAGUUC | 302 |
| 103 | CCCUCAU C UUCCCGG | 202 | 508 | UCCAAGU U CCUAUAG | 303 |
| 105 | CUCAUCU U CCCGGCA | 203 | 509 | CCAAGUU C CUAUAGA | 304 |
| 106 | UCAUCUU C CCGGCAG | 204 | 512 | AGUUCCU A UAGAAGA | 305 |
| 129 | CAGGCCU C UGGCCCC | 205 | 514 | UUCCUAU A GAAGAGC | 306 |
| 138 | GGCCCCU A UGUGGAG | 206 | 534 | GGGGACU A CGACCUG | 307 |
| 148 | UGGAGAU C AUUGAGC | 207 | 556 | UGCGGCU C UGCUUCC | 308 |
| 151 | AGAUCAU U GAGCAGC | 208 | 561 | CUCUGCU U CCAGGUG | 309 |
| 180 | AUGCGCU U CCGCUAC | 209 | 562 | UCUGCUU C CAGGUGA | 310 |
| 181 | UGCGCUU C CGCUACA | 210 | 585 | GACCCAU C AGGCAGG | 311 |
| 186 | UUCCGCU A CAAGUGC | 211 | 598 | GGCCCCU C CGCCUGC | 312 |
| 204 | GGGCGCU C CGCGGGC | 212 | 613 | CGCCUGU C CUUCCUC | 313 |
| 217 | GCAGCAU C CCAGGCG | 213 | 616 | CUGUCCU U CCUCAUC | 314 |
| 239 | CACAGAU A CCACCAA | 214 | 617 | UGUCCUU C CUCAUCC | 315 |
| 262 | CCACCAU C AAGAUCA | 215 | 620 | CCUUCCU C AUCCCAU | 316 |
| 268 | UCAAGAU C AAUGGCU | 216 | 623 | UCCUCAU C CCAUCUU | 317 |
| 276 | AAUGGCU A CACAGGA | 217 | 628 | AUCCCAU C UUUGACA | 318 |
| 301 | UGCGCAU C UCCCUGG | 218 | 630 | CCCAUCU U UGACAAU | 319 |
| 303 | CGCAUCU C CCUGGUC | 219 | 631 | CCAUCUU U GACAAUC | 320 |
| 310 | CCCUGGU C ACCAAGG | 220 | 638 | UGACAAU C GUGCCCC | 321 |
| 323 | GGACCCU C CUCACCG | 221 | 661 | CCGAGCU C AAGAUCU | 322 |
| 326 | CCCUCCU C ACCGGCC | 222 | 667 | UCAAGAU C UGCCGAG | 323 |
| 335 | CCGGCCU C ACCCCCA | 223 | 687 | CGAAACU C UGGCAGC | 324 |
| 349 | ACGAGCU U GUAGGAA | 224 | 700 | GCUGCCU C GGUGGGG | 325 |
| 352 | AGCUUGU A GGAAAGG | 225 | 715 | AUGAGAU C UUCCUAC | 326 |
| 375 | GAUGGCU U CUAUGAG | 226 | 717 | GAGAUCU U CCUACUG | 327 |
| 376 | AUGGCUU C UAUGAGG | 227 | 718 | AGAUCUU C CUACUGU | 328 |
| 378 | GGCUUCU A UGAGGCU | 228 | 721 | UCUUCCU A CUGUGUG | 329 |
| 391 | CUGAGCU C UGCCCGG | 229 | 751 | AGGACAU U GAGGUGU | 330 |
| 409 | GCUGCAU C CACAGUU | 230 | 759 | GAGGUGU A UUUCACG | 331 |
| 416 | CCACAGU U UCCAGAA | 231 | 761 | GGUGUAU U UCACGGG | 332 |

TABLE III-continued

Human rel A HH Target Sequences

| nt. Pos. | HH Target Sequence | Seq. ID No. | nt. Pos. | HH Target Sequence | Seq. ID No. |
|---|---|---|---|---|---|
| 417 | CACAGUU U CCAGAAC | 232 | 762 | GUGUAUU U CACGGGA | 333 |
| 418 | ACAGUUU C CAGAACC | 233 | 763 | UGUAUUU C ACGGGAC | 334 |
| 433 | UGGGAAU C CAGUGUG | 234 | 792 | CGAGGCU C CUUUUCG | 335 |
| 795 | GGCUCCU U UUCGCAA | 235 | 1167 | GAUGAGU U UCCCACC | 336 |
| 796 | GCUCCUU U UCGCAAG | 236 | 1168 | AUGAGUU U CCCACCA | 337 |
| 797 | CUCCUUU U CGCAAGC | 237 | 1169 | UGAGUUU C CCACCAU | 338 |
| 798 | UCCUUUU C GCAAGCU | 238 | 1182 | AUGGUGU U UCCUUCU | 339 |
| 829 | UGGCCAU U GUGUUCC | 239 | 1183 | UGGUGUU U CCUUCUG | 340 |
| 834 | AUUGUGU U CCGGACC | 240 | 1184 | GGUGUUU C CUUCUGG | 341 |
| 835 | UUGUGUU C CGGACCC | 241 | 1187 | GUUUCCU U CUGGGCA | 342 |
| 845 | GACCCCU C CCUACGC | 242 | 1188 | UUUCCUU C UGGGCAG | 343 |
| 849 | CCUCCCU A CGCAGAC | 243 | 1198 | GGCAGAU C AGCCAGG | 344 |
| 872 | GCAGGCU C CUGUGCG | 244 | 1209 | CAGGCCU G GGCCUUG | 345 |
| 883 | UGCGUGU C UCCAUGC | 245 | 1215 | UCGGCCU U GGCCCCG | 346 |
| 885 | CGUGUCU C CAUGCAG | 246 | 1229 | GGCCCCU C CCCAAGU | 347 |
| 905 | GCGGCCU U CCGACCG | 247 | 1237 | CCCAAGU C CUGCCCC | 348 |
| 906 | CGGCCUU C CGACCGG | 248 | 1250 | CCAGGCU C CAGCCCC | 349 |
| 919 | GGGAGCU C AGUGAGC | 249 | 1268 | CCCUGCU C CAGCCAU | 350 |
| 936 | AUGGAAU U CCAGUAC | 250 | 1279 | CCAUGGU U UCAGCUC | 351 |
| 937 | UGGAAUU C CAGUACC | 251 | 1281 | AUGGUAU C AGCUCUG | 352 |
| 942 | UUCCAGU A CCUGCCA | 252 | 1286 | AUCAGCU C UGGCCCA | 353 |
| 953 | GCCAGAU A CAGACGA | 253 | 1309 | CCCCUGU C CCAGUCC | 354 |
| 962 | AGACGAU C GUCACCG | 254 | 1315 | UCCCAGU C CAUGCCC | 355 |
| 965 | CGAUCGU C ACCGGAU | 255 | 1318 | CAGUCCU A GCCCCAG | 356 |
| 973 | ACCGGAU U GAGGAGA | 256 | 1331 | AGGCCCU C CUCAGGC | 357 |
| 986 | GAAACGU A AAAGGAC | 257 | 1334 | CCCUCCU C AGGCUGU | 358 |
| 996 | AGGACAU A UGAGACC | 258 | 1389 | ACGCUGU C AGAGGCC | 359 |
| 1005 | GAGACCU U CAAGAGC | 259 | 1413 | CUGCAGU U UGAUGAU | 360 |
| 1006 | AGACCUU C AAGAGCA | 260 | 1414 | UGCAGUU U GAUGAUG | 361 |
| 1015 | AGCAGCAU C AUGAAGA | 261 | 1437 | GGGGCCU U GCUUGGC | 362 |
| 1028 | GAAGAGU C CUUUCAG | 262 | 1441 | CCUUGCU U GGCAACA | 363 |
| 1031 | GAGUCCU U UCAGCGG | 263 | 1467 | GCUGUGU U CACAGAC | 364 |
| 1032 | AGUCCUU U CAGCGGA | 264 | 1468 | CUGUGUU C ACAGACC | 365 |
| 1033 | GUCCUUU C AGCGGAC | 265 | 1482 | CUGGCAU C CGUCGAC | 366 |
| 1058 | CCGGCCU C CACCUCG | 266 | 1486 | CAUCCGU C GACAACU | 367 |
| 1064 | UCCACCU C GACGCAU | 267 | 1494 | GACAACU C GAGUUU | 368 |
| 1072 | GACGCAU U GCUGUGC | 268 | 1500 | UCCGAGU U UCAGCAG | 369 |
| 1082 | UGUGCCU U CCCGCAG | 269 | 1501 | CCGAGUU U CAGCAGC | 370 |
| 1083 | GUGCCUU C CCGCAGC | 270 | 1502 | CGAGUUU C AGCAGCU | 371 |
| 1092 | CGCAGCU C AGCUUCU | 271 | 1525 | AGGGCAU A CCUGUGG | 372 |
| 1097 | CUCAGCU U CUGUCCC | 272 | 1566 | AUGGAGU A CCCUGAG | 373 |
| 1098 | UCAGCUU C UGUCCCC | 273 | 1577 | UGAGGCU A UAACUCG | 374 |
| 1102 | CUUCUGU C CCCAAGC | 274 | 1579 | AGGCUAU A ACUCGCC | 375 |
| 1125 | CAGCCCU A UCCCUUU | 275 | 1583 | UAUAACU C GCCUAGU | 376 |
| 1127 | GCCCUAU C CCUUUAC | 276 | 1588 | CUCGCCU A GUGACAG | 377 |
| 1131 | UAUCCCU U UACGUCA | 277 | 1622 | CCCAGCU C CUGCUCC | 378 |
| 1132 | AUCCCUU U ACGUCAU | 278 | 1628 | UCCUGCU C CACUGGG | 379 |
| 1133 | UCCCUUU A CGUCAUC | 279 | 1648 | CGGGGCU C CCCAAUG | 380 |
| 1137 | UUUACGU C AUCCCUG | 280 | 1660 | AUGGCCU C CUUUCAG | 381 |
| 1140 | ACGUCAU C CCUGAGC | 281 | 1663 | GCCUCCU U UCAGGAG | 382 |
| 1153 | GCACCAU C AACUAUG | 282 | 1664 | CCUCCUU U CAGGAGA | 383 |
| 1158 | AUCAACU A UGAUGAG | 283 | 1665 | CUCCUUU C AGGAGAU | 384 |
| 1680 | GAAGACU U CUCCUCC | 284 | | | |
| 1681 | AAGACUU C UCCUCCA | 285 | | | |
| 1683 | GACUUCU C CUCCAUU | 286 | | | |
| 1686 | UUCUCCU C CAUUGCG | 287 | | | |
| 1690 | CCUCCAU U GCGGACA | 288 | | | |
| 1704 | AUGGACU U CUCAGCC | 289 | | | |
| 1705 | UGGACUU C UCAGCCC | 290 | | | |
| 1707 | GACUUCU C AGCCCUG | 291 | | | |
| 1721 | GCUGAGU C AGAUCAG | 292 | | | |
| 1726 | GUCAGAU C AGCUCCU | 293 | | | |
| 1731 | AUCAGCU C CUAAGGG | 294 | | | |
| 1734 | AGCUCCU A AGGGGGU | 295 | | | |
| 1754 | CUGCCCU C CCCAGAG | 296 | | | |

TABLE IV

Mouse rel A HH Ribozyme Sequences

| nt. Seq. | HH Ribozyme Sequence | Seq. ID No. |
|---|---|---|
| 19 | UCCUGUG CUGAUGAGGCCGAAAGGCCGAA AGCCAUU | 385 |
| 22 | CACCACG CUGAUGAGGCCGAAAGGCCGAA AGGAGCU | 386 |
| 26 | UGUCCGC CUGAUGAGGCCGAAAGGCCGAA AUGGAGG | 387 |
| 93 | GAGGGGA CUGAUGAGGCCGAAAGGCCGAA ACAGAUC | 388 |
| 94 | UGAGGGG CUGAUGAGGCCGAAAGGCCGAA AACAGAU | 389 |
| 100 | GAAAGAU CUGAUGAGGCCGAAAGGCCGAA AGGGGAA | 390 |
| 103 | AGGGAAA CUGAUGAGGCCGAAAGGCCGAA AUGAGGG | 391 |
| 105 | UGAGGGA CUGAUGAGGCCGAAAGGCCGAA AGAUGAG | 392 |
| 106 | CUGAGGG CUGAUGAGGCCGAAAGGCCGAA AAGAUGA | 393 |
| 129 | AGGCCCA CUGAUGAGGCCGAAAGGCCGAA AAGCCUG | 394 |
| 138 | CUCCACA CUGAUGAGGCCGAAAGGCCGAA AAGGCCC | 395 |
| 148 | GUUCGAU CUGAUGAGGCCGAAAGGCCGAA AUCUCCA | 396 |
| 151 | GCUGUUC CUGAUGAGGCCGAAAGGCCGAA AUGAUCU | 397 |
| 180 | AUAGCGG CUGAUGAGGCCGAAAGGCCGAA AUCGCAU | 398 |
| 181 | UAUAGCG CUGAUGAGGCCGAAAGGCCGAA AAUCGCA | 399 |
| 186 | GCAUUUA CUGAUGAGGCCGAAAGGCCGAA AGCGGAA | 400 |
| 204 | GCCCGCU CUGAUGAGGCCGAAAGGCCGAA AGCGCCC | 401 |
| 217 | CGCCAGG CUGAUGAGGCCGAAAGGCCGAA AUACUGC | 402 |
| 239 | UUGGUGG CUGAUGAGGCCGAAAGGCCGAA AUCUGUG | 403 |
| 262 | UGAUCUU CUGAUGAGGCCGAAAGGCCGAA AUGGUGG | 404 |
| 268 | AGCCAUU CUGAUGAGGCCGAAAGGCCGAA AUCUUGA | 405 |
| 276 | UCCUGUG CUGAUGAGGCCGAAAGGCCGAA AGCCAUU | 406 |
| 301 | CCAGGGA CUGAUGAGGCCGAAAGGCCGAA AUUCGAA | 407 |
| 303 | GACCAGG CUGAUGAGGCCGAAAGGCCGAA AGAUUCG | 408 |
| 310 | CCUUGGU CUGAUGAGGCCGAAAGGCCGAA ACCAGGG | 409 |
| 323 | UCAGGAG CUGAUGAGGCCGAAAGGCCGAA AGGGGCC | 410 |
| 326 | GGCCGGU CUGAUGAGGCCGAAAGGCCGAA AGGUGGA | 411 |
| 335 | UGUGGAU CUGAUGAGGCCGAAAGGCCGAA AGGCCGG | 412 |
| 349 | UCCCCAC CUGAUGAGGCCGAAAGGCCGAA AGUUCAU | 413 |
| 352 | GCUGUUC CUGAUGAGGCCGAAAGGCCGAA AUGAUCU | 414 |
| 375 | CUCAUAG CUGAUGAGGCCGAAAGGCCGAA AGCCAUC | 415 |
| 376 | CUCCGGA CUGAUGAGGCCGAAAGGCCGAA AGACCAU | 416 |
| 378 | AGCCUCA CUGAUGAGGCCGAAAGGCCGAA AGUAGCC | 417 |
| 391 | CUGGGCA CUGAUGAGGCCGAAAGGCCGAA AGGUCAG | 418 |
| 409 | AGCUAUG CUGAUGAGGCCGAAAGGCCGAA AUACUGC | 419 |
| 416 | CUAUGGA CUGAUGAGGCCGAAAGGCCGAA ACUGCGG | 420 |
| 417 | GUUCUGG CUGAUGAGGCCGAAAGGCCGAA AGCUAUG | 421 |
| 418 | GGUUCUG CUGAUGAGGCCGAAAGGCCGAA AAGCUAU | 422 |
| 433 | CACACUG CUGAUGAGGCCGAAAGGCCGAA AUCCCCA | 423 |
| 467 | CGAACAG CUGAUGAGGCCGAAAGGCCGAA AGCCUGG | 424 |
| 469 | GCUGGCU CUGAUGAGGCCGAAAGGCCGAA AUGGCUU | 425 |
| 473 | CUGAUCU CUGAUGAGGCCGAAAGGCCGAA ACUCAAA | 426 |
| 481 | UGGUCUG CUGAUGAGGCCGAAAGGCCGAA AUUCGCU | 427 |
| 501 | AACGUGA CUGAUGAGGCCGAAAGGCCGAA AGGGGUU | 428 |
| 502 | GAACGUG CUGAUGAGGCCGAAAGGCCGAA AAGGGGU | 429 |
| 508 | CUAUAGG CUGAUGAGGCCGAAAGGCCGAA ACGUGAA | 430 |
| 509 | UCUAUAG CUGAUGAGGCCGAAAGGCCGAA AACGUGA | 431 |
| 512 | UCCUCUA CUGAUGAGGCCGAAAGGCCGAA AGGAACG | 432 |
| 514 | GCUCCUC CUGAUGAGGCCGAAAGGCCGAA AUAGGAA | 433 |
| 534 | CAAGUCA CUGAUGAGGCCGAAAGGCCGAA AGUCCCC | 434 |
| 556 | GGAAGCA CUGAUGAGGCCGAAAGGCCGAA AGGCGCA | 435 |
| 561 | CACCUGG CUGAUGAGGCCGAAAGGCCGAA AGCAGAG | 436 |
| 562 | UCACCUG CUGAUGAGGCCGAAAGGCCGAA AAGCAGA | 437 |
| 585 | GCUGGCU CUGAUGAGGCCGAAAGGCCGAA AUGGCUU | 438 |
| 598 | UCAGGAG CUGAUGAGGCCGAAAGGCCGAA AGGGGCC | 439 |
| 613 | GUGAGAG CUGAUGAGGCCGAAAGGCCGAA ACAGGGG | 440 |
| 616 | GAUGUGA CUGAUGAGGCCGAAAGGCCGAA AGGACAG | 441 |
| 617 | GGCUGAG CUGAUGAGGCCGAAAGGCCGAA AAGGGAC | 442 |
| 620 | CAUGGCU CUGAUGAGGCCGAAAGGCCGAA AGGAAGG | 443 |
| 623 | GAGAUGG CUGAUGAGGCCGAAAGGCCGAA AGCAGGA | 444 |
| 628 | UAUCAAA CUGAUGAGGCCGAAAGGCCGAA AUCGGAU | 445 |
| 630 | GUUAUCA CUGAUGAGGCCGAAAGGCCGAA AAAUCGG | 446 |
| 631 | GGUUAUC CUGAUGAGGCCGAAAGGCCGAA AAAAUCG | 447 |
| 638 | GGAACAC CUGAUGAGGCCGAAAGGCCGAA AUGGCCA | 448 |
| 661 | AGAUCUU CUGAUGAGGCCGAAAGGCCGAA AGCUCGG | 449 |
| 667 | CUCGGCA CUGAUGAGGCCGAAAGGCCGAA AUCUUGA | 450 |
| 687 | GCUCCCA CUGAUGAGGCCGAAAGGCCGAA AGUUCCG | 451 |
| 700 | CCCCACC CUGAUGAGGCCGAAAGGCCGAA AGGCAGC | 452 |
| 715 | GCAAGAA CUGAUGAGGCCGAAAGGCCGAA AUCUCAU | 453 |
| 717 | CAGCAAG CUGAUGAGGCCGAAAGGCCGAA AGAUCUC | 454 |
| 718 | ACAGCAA CUGAUGAGGCCGAAAGGCCGAA AAGAUCU | 455 |
| 721 | CGCAAUG CUGAUGAGGCCGAAAGGCCGAA AGGAGAA | 456 |
| 751 | ACACCUC CUGAUGAGGCCGAAAGGCCGAA AUGUCUU | 457 |
| 759 | CGUGAAA CUGAUGAGGCCGAAAGGCCGAA ACACCUC | 458 |
| 761 | CCCGUGA CUGAUGAGGCCGAAAGGCCGAA AUACACC | 459 |

TABLE IV-continued

Mouse rel A HH Ribozyme Sequences

| nt. Seq. | HH Ribozyme Sequence | Seq. ID No. |
|---|---|---|
| 762 | UCCCGUG CUGAUGAGGCCGAAAGGCCGAA AAUACAC | 460 |
| 763 | GUCCCGU CUGAUGAGGCCGAAAGGCCGAA AAAUACA | 461 |
| 792 | AGAAAAG CUGAUGAGGCCGAAAGGCCGAA AGCCUCG | 462 |
| 795 | UUGAGAA CUGAUGAGGCCGAAAGGCCGAA AGGAGCC | 463 |
| 796 | CUUGAGA CUGAUGAGGCCGAAAGGCCGAA AAGGAGC | 464 |
| 797 | GCUUGAG CUGAUGAGGCCGAAAGGCCGAA AAAGGAG | 465 |
| 798 | AGCUUGA CUGAUGAGGCCGAAAGGCCGAA AAAAGGA | 466 |
| 829 | GGAACAC CUGAUGAGGCCGAAAGGCCGAA AUGGCCA | 467 |
| 834 | AGUCCGG CUGAUGAGGCCGAAAGGCCGAA ACACAAU | 468 |
| 835 | GAGUCCG CUGAUGAGGCCGAAAGGCCGAA AACACAA | 469 |
| 845 | GCGUACG CUGAUGAGGCCGAAAGGCCGAA AGGAGUC | 470 |
| 849 | GUCGGCG CUGAUGAGGCCGAAAGGCCGAA ACGGAGG | 471 |
| 872 | CGAACAG CUGAUGAGGCCGAAAGGCCGAA AGCCUGG | 472 |
| 883 | GCAUGGA CUGAUGAGGCCGAAAGGCCGAA ACUCGAA | 473 |
| 885 | CUGCAUG CUGAUGAGGCCGAAAGGCCGAA AGACUCG | 474 |
| 905 | CGAUCAG CUGAUGAGGCCGAAAGGCCGAA AGGCCGC | 475 |
| 906 | GCGAUCA CUGAUGAGGCCGAAAGGCCGAA AAGGCCG | 476 |
| 919 | GCUCACU CUGAUGAGGCCGAAAGGCCGAA AGCUCGC | 477 |
| 936 | GUACUGG CUGAUGAGGCCGAAAGGCCGAA ACUCCAU | 478 |
| 937 | AGUACUG CUGAUGAGGCCGAAAGGCCGAA AACUCCA | 479 |
| 942 | UGGCAAG CUGAUGAGGCCGAAAGGCCGAA ACUGGAA | 480 |
| 953 | UCAUGUG CUGAUGAGGCCGAAAGGCCGAA AUGAGGC | 481 |
| 962 | CGGUGGC CUGAUGAGGCCGAAAGGCCGAA AUCAUCU | 482 |
| 965 | GUCUGGC CUGAUGAGGCCGAAAGGCCGAA AGUACUG | 483 |
| 973 | UCUCUUC CUGAUGAGGCCGAAAGGCCGAA AUCCGGU | 484 |
| 986 | ACUCUUG CUGAUGAGGCCGAAAGGCCGAA AGGUCUC | 485 |
| 996 | GGUCUCA CUGAUGAGGCCGAAAGGCCGAA AGGUCCU | 486 |
| 1005 | ACUCUUG CUGAUGAGGCCGAAAGGCCGAA AGGUCUC | 487 |
| 1006 | UACUCUU CUGAUGAGGCCGAAAGGCCGAA AAGGUCU | 488 |
| 1015 | UCUUCAU CUGAUGAGGCCGAAAGGCCGAA AUACUCU | 489 |
| 1028 | UUGAAAG CUGAUGAGGCCGAAAGGCCGAA ACUCUUC | 490 |
| 1031 | CCAUUGA CUGAUGAGGCCGAAAGGCCGAA AGGACUC | 491 |
| 1032 | UCCAUUG CUGAUGAGGCCGAAAGGCCGAA AAGGACU | 492 |
| 1033 | GUCCAUU CUGAUGAGGCCGAAAGGCCGAA AAAGGAC | 493 |
| 1058 | CGGGUUG CUGAUGAGGCCGAAAGGCCGAA AGGCCGG | 494 |
| 1064 | UUGGAUC CUGAUGAGGCCGAAAGGCCGAA AGGUGUA | 495 |
| 1072 | GCACAGC CUGAUGAGGCCGAAAGGCCGAA AUACGCC | 496 |
| 1082 | UUUCGGG CUGAUGAGGCCGAAAGGCCGAA AGGCACA | 497 |
| 1083 | ACUUCGG CUGAUGAGGCCGAAAGGCCGAA AAGGCUU | 498 |
| 1092 | AGAAGUU CUGAUGAGGCCGAAAGGCCGAA AGUUUCG | 499 |
| 1097 | GGGACAG CUGAUGAGGCCGAAAGGCCGAA AGUUGAG | 500 |
| 1098 | GGGGACA CUGAUGAGGCCGAAAGGCCGAA AAGUUGA | 501 |
| 1102 | GCUUGGG CUGAUGAGGCCGAAAGGCCGAA ACAGAAG | 502 |
| 1125 | GAAGGUG CUGAUGAGGCCGAAAGGCCGAA AGGGCUG | 503 |
| 1127 | GUAAGGC CUGAUGAGGCCGAAAGGCCGAA AUAUGGC | 504 |
| 1131 | UGGUGCU CUGAUGAGGCCGAAAGGCCGAA AGGGAUG | 505 |
| 1132 | AUGCUGG CUGAUGAGGCCGAAAGGCCGAA AAGGUGU | 506 |
| 1133 | GAAGCUG CUGAUGAGGCCGAAAGGCCGAA AGAUGGA | 507 |
| 1137 | GCGCGCU CUGAUGAGGCCGAAAGGCCGAA AAGUAAA | 508 |
| 1140 | GCUGAGG CUGAUGAGGCCGAAAGGCCGAA AUGCUGG | 509 |
| 1153 | CAAAGUU CUGAUGAGGCCGAAAGGCCGAA AUGGUGC | 510 |
| 1158 | CUCAUCA CUGAUGAGGCCGAAAGGCCGAA AGUUGAU | 511 |
| 1167 | GGGGGAA CUGAUGAGGCCGAAAGGCCGAA ACUCAUC | 512 |
| 1168 | UGGGGGA CUGAUGAGGCCGAAAGGCCGAA AACUCAU | 513 |
| 1169 | AUGGGGG CUGAUGAGGCCGAAAGGCCGAA AAACUCA | 514 |
| 1182 | UGAUGGU CUGAUGAGGCCGAAAGGCCGAA ACAGCAU | 515 |
| 1183 | CUGAUGG CUGAUGAGGCCGAAAGGCCGAA AACAGCA | 516 |
| 1184 | UCAGGAG CUGAUGAGGCCGAAAGGCCGAA AGGGGCC | 517 |
| 1187 | GGCUGAG CUGAUGAGGCCGAAAGGCCGAA AAGGGAC | 518 |
| 1188 | CUGCCCU CUGAUGAGGCCGAAAGGCCGAA AUGGUAA | 519 |
| 1198 | UCAGACU CUGAUGAGGCCGAAAGGCCGAA AACUCCC | 520 |
| 1209 | GAAGGUG CUGAUGAGGCCGAAAGGCCGAA AGGGCUG | 521 |
| 1215 | CGGUGCU CUGAUGAGGCCGAAAGGCCGAA AGGCCAG | 522 |
| 1229 | GCUGAGG CUGAUGAGGCCGAAAGGCCGAA AGGGACC | 523 |
| 1237 | GGGGCAG CUGAUGAGGCCGAAAGGCCGAA AGCUGGG | 524 |
| 1250 | GAGCCUG CUGAUGAGGCCGAAAGGCCGAA AGGCUGG | 525 |
| 1268 | GGGGCAG CUGAUGAGGCCGAAAGGCCGAA AGCUGGG | 526 |
| 1279 | AGGAAGG CUGAUGAGGCCGAAAGGCCGAA ACCAUGG | 527 |
| 1281 | CGCAGCU CUGAUGAGGCCGAAAGGCCGAA AGCCCAC | 528 |
| 1286 | UGGGGGA CUGAUGAGGCCGAAAGGCCGAA AACUCAU | 529 |
| 1309 | AGACUCG CUGAUGAGGCCGAAAGGCCGAA ACAGGAG | 530 |
| 1315 | GGGUUAG CUGAUGAGGCCGAAAGGCCGAA ACUGGGG | 531 |
| 1318 | CCGGGGU CUGAUGAGGCCGAAAGGCCGAA AGAACUG | 532 |
| 1331 | GACUGGG CUGAUGAGGCCGAAAGGCCGAA AGGACCC | 533 |
| 1334 | UCAGCUU CUGAUGAGGCCGAAAGGCCGAA AGAAAAG | 534 |

TABLE IV-continued

Mouse rel A HH Ribozyme Sequences

| nt. Seq. | HH Ribozyme Sequence | Seq. ID No. |
|---|---|---|
| 1389 | GGCUUCC CUGAUGAGGCCGAAAGGCCGAA ACAGCGU | 535 |
| 1413 | AGCAUCA CUGAUGAGGCCGAAAGGCCGAA ACUGCAG | 536 |
| 1414 | CAGCAUC CUGAUGAGGCCGAAAGGCCGAA AACUGCA | 537 |
| 1437 | GCCAAGC CUGAUGAGGCCGAAAGGCCGAA AGGCCCC | 538 |
| 1441 | UGUUGCC CUGAUGAGGCCGAAAGGCCGAA AGCAAGG | 539 |
| 1467 | GUCUGUG CUGAUGAGGCCGAAAGGCCGAA ACACUCC | 540 |
| 1468 | GGUCUGU CUGAUGAGGCCGAAAGGCCGAA AACACUC | 541 |
| 1482 | GUCCACA CUGAUGAGGCCGAAAGGCCGAA AUGCCAG | 542 |
| 1486 | AGUUCCC CUGAUGAGGCCGAAAGGCCGAA ACCGAAG | 543 |
| 1494 | AAACUCU CUGAUGAGGCCGAAAGGCCGAA AGUUGUC | 544 |
| 1500 | CUGCUGA CUGAUGAGGCCGAAAGGCCGAA ACUCUGA | 545 |
| 1501 | GCUGCUG CUGAUGAGGCCGAAAGGCCGAA AACUCUG | 546 |
| 1502 | AGCUGCU CUGAUGAGGCCGAAAGGCCGAA AAACUCU | 547 |
| 1525 | ACACAGG CUGAUGAGGCCGAAAGGCCGAA AUGCACC | 548 |
| 1566 | UUCAGGG CUGAUGAGGCCGAAAGGCCGAA ACUCCAU | 549 |
| 1577 | CGAGUUA CUGAUGAGGCCGAAAGGCCGAA AGCUUCA | 550 |
| 1579 | GGCGAGU CUGAUGAGGCCGAAAGGCCGAA AUAGCUU | 551 |
| 1583 | ACCAGGC CUGAUGAGGCCGAAAGGCCGAA AGUUAUA | 552 |
| 1588 | CCCUCUC CUGAUGAGGCCGAAAGGCCGAA AGGAGAG | 553 |
| 1622 | GGGGCAG CUGAUGAGGCCGAAAGGCCGAA AGCUGGG | 554 |
| 1628 | CCUACCG CUGAUGAGGCCGAAAGGCCGAA AGCAGGA | 555 |
| 1648 | CAUUGGG CUGAUGAGGCCGAAAGGCCGAA AGCCCCG | 556 |
| 1660 | CUGGGCA CUGAUGAGGCCGAAAGGCCGAA AGGUCAG | 557 |
| 1663 | CACCUGG CUGAUGAGGCCGAAAGGCCGAA AGCAGAG | 558 |
| 1664 | UCACCUG CUGAUGAGGCCGAAAGGCCGAA AAGCAGA | 559 |
| 1665 | ACCUCCG CUGAUGAGGCCGAAAGGCCGAA AAGCGAG | 560 |
| 1680 | GGAGGAG CUGAUGAGGCCGAAAGGCCGAA AGUCUUC | 561 |
| 1681 | UGGAGGA CUGAUGAGGCCGAAAGGCCGAA AAGUCUU | 562 |
| 1683 | AAUGGAG CUGAUGAGGCCGAAAGGCCGAA AGAAGUC | 563 |
| 1686 | CGCAAUG CUGAUGAGGCCGAAAGGCCGAA AGGAGAA | 564 |
| 1690 | UGUCCGC CUGAUGAGGCCGAAAGGCCGAA AUGGAGG | 565 |
| 1704 | AGCAGAG CUGAUGAGGCCGAAAGGCCGAA AGUCCAU | 566 |
| 1705 | GAGCAGA CUGAUGAGGCCGAAAGGCCGAA AAGUCCA | 567 |
| 1707 | AAGAGCA CUGAUGAGGCCGAAAGGCCGAA AGAAGUC | 568 |
| 1721 | CUGAUCU CUGAUGAGGCCGAAAGGCCGAA ACUCAAA | 569 |
| 1726 | AGGAGCU CUGAUGAGGCCGAAAGGCCGAA AUCUGAC | 570 |
| 1731 | ACCUUAG CUGAUGAGGCCGAAAGGCCGAA AGCUGAU | 571 |
| 1734 | AGCACCU CUGAUGAGGCCGAAAGGCCGAA AGGAGCU | 572 |
| 1754 | CUCUUGG CUGAUGAGGCCGAAAGGCCGAA AGCACUG | 573 |

TABLE V

Human rel A HH Ribozyme Sequences

| nt. Sequence | HH Ribozyme Sequence | SEQ ID NO. |
|---|---|---|
| 19 | UACAGAC CUGAUGAGGCCGAAAGGCCGAA AGCCAUU | 574 |
| 22 | CACUACA CUGAUGAGGCCGAAAGGCCGAA ACGAGCC | 575 |
| 26 | CGUGCAC CUGAUGAGGCCGAAAGGCCGAA ACAGACG | 576 |
| 93 | GAGGGGG CUGAUGAGGCCGAAAGGCCGAA ACAGUUC | 577 |
| 94 | UGAGGGG CUGAUGAGGCCGAAAGGCCGAA AACAGUU | 578 |
| 100 | GGAAGAU CUGAUGAGGCCGAAAGGCCGAA AGGGGGA | 579 |
| 103 | CCGGGAA CUGAUGAGGCCGAAAGGCCGAA AUGAGGG | 580 |
| 105 | UGCCGGG CUGAUGAGGCCGAAAGGCCGAA AGAUGAG | 581 |
| 106 | CUGCCGG CUGAUGAGGCCGAAAGGCCGAA AAGAUGA | 582 |
| 129 | GGGGCCA CUGAUGAGGCCGAAAGGCCGAA AGGCCUG | 583 |
| 138 | CUCCACA CUGAUGAGGCCGAAAGGCCGAA AGGGGCC | 584 |
| 148 | GCUCAAU CUGAUGAGGCCGAAAGGCCGAA AUCUCCA | 585 |
| 151 | GCUGCUC CUGAUGAGGCCGAAAGGCCGAA AUGAUCU | 586 |
| 180 | GUAGCGG CUGAUGAGGCCGAAAGGCCGAA AGCGCAU | 587 |
| 181 | UGUAGCG CUGAUGAGGCCGAAAGGCCGAA AAGCGCA | 588 |
| 186 | GCACUUG CUGAUGAGGCCGAAAGGCCGAA AGCGGAA | 589 |
| 204 | GCCCGCG CUGAUGAGGCCGAAAGGCCGAA AGCGCCC | 590 |
| 217 | CGCCUGG CUGAUGAGGCCGAAAGGCCGAA AUGCUGC | 591 |
| 239 | UUGGUGG CUGAUGAGGCCGAAAGGCCGAA AUCUGUG | 592 |
| 262 | UGAUCUU CUGAUGAGGCCGAAAGGCCGAA AUGGUGG | 593 |
| 268 | AGCCAUU CUGAUGAGGCCGAAAGGCCGAA AUCUUGA | 594 |
| 276 | UCCUGUG CUGAUGAGGCCGAAAGGCCGAA AGCCAUU | 595 |
| 301 | CCAGGGA CUGAUGAGGCCGAAAGGCCGAA AUGCGCA | 596 |
| 303 | GACCAGG CUGAUGAGGCCGAAAGGCCGAA AGAUGCG | 597 |
| 310 | CCUUGGU CUGAUGAGGCCGAAAGGCCGAA ACCAGGG | 598 |

TABLE V-continued

Human rel A HH Ribozyme Sequences

| nt. Sequence | HH Ribozyme Sequence | SEQ ID NO. |
|---|---|---|
| 323 | CGGUGAG CUGAUGAGGCCGAAAGGCCGAA AGGGUCC | 599 |
| 326 | GGCCGGU CUGAUGAGGCCGAAAGGCCGAA AGGAGGG | 600 |
| 335 | UGGGGGU CUGAUGAGGCCGAAAGGCCGAA AGGCCGG | 601 |
| 349 | UUCCUAC CUGAUGAGGCCGAAAGGCCGAA AGCUCGU | 602 |
| 352 | CCUUUCC CUGAUGAGGCCGAAAGGCCGAA ACAAGCU | 603 |
| 375 | CUCAUAG CUGAUGAGGCCGAAAGGCCGAA AGCCAUC | 604 |
| 376 | CCUCAUA CUGAUGAGGCCGAAAGGCCGAA AAGCCAU | 605 |
| 378 | AGCCUCA CUGAUGAGGCCGAAAGGCCGAA AGAAGCC | 606 |
| 391 | CCGGGCA CUGAUGAGGCCGAAAGGCCGAA AGCUCAG | 607 |
| 409 | AACUGUG CUGAUGAGGCCGAAAGGCCGAA AUGCAGC | 608 |
| 416 | UUCUGGA CUGAUGAGGCCGAAAGGCCGAA ACUGUGG | 609 |
| 417 | GUUCUGG CUGAUGAGGCCGAAAGGCCGAA AACUGUG | 610 |
| 418 | GGUUCUG CUGAUGAGGCCGAAAGGCCGAA AAACUGU | 611 |
| 433 | CACACUG CUGAUGAGGCCGAAAGGCCGAA AUUCCCA | 612 |
| 467 | UGACUGA CUGAUGAGGCCGAAAGGCCGAA AGCCUGC | 613 |
| 469 | GCUGACU CUGAUGAGGCCGAAAGGCCGAA AUAGCCU | 614 |
| 473 | AUGCGCU CUGAUGAGGCCGAAAGGCCGAA ACUGAUA | 615 |
| 481 | UGGUCUG CUGAUGAGGCCGAAAGGCCGAA AUGCGCU | 616 |
| 501 | AACUUGG CUGAUGAGGCCGAAAGGCCGAA AGGGGUU | 617 |
| 502 | GAACUUG CUGAUGAGGCCGAAAGGCCGAA AAGGGGU | 618 |
| 508 | CUAUAGG CUGAUGAGGCCGAAAGGCCGAA ACUUGAA | 619 |
| 509 | UCUAUAG CUGAUGAGGCCGAAAGGCCGAA AACUUGG | 620 |
| 512 | UCUUCUA CUGAUGAGGCCGAAAGGCCGAA AGGAACU | 621 |
| 514 | GCUCUUC CUGAUGAGGCCGAAAGGCCGAA AUAGGAA | 622 |
| 534 | CAGGUCG CUGAUGAGGCCGAAAGGCCGAA AGUCCCC | 623 |
| 556 | GGAAGCA CUGAUGAGGCCGAAAGGCCGAA AGCCGCA | 624 |
| 561 | CACCUGG CUGAUGAGGCCGAAAGGCCGAA AGCAGAG | 625 |
| 562 | UCACCUG CUGAUGAGGCCGAAAGGCCGAA AAGCAGA | 626 |
| 585 | CCUGCCU CUGAUGAGGCCGAAAGGCCGAA AUGGGUC | 627 |
| 598 | GCAGGCG CUGAUGAGGCCGAAAGGCCGAA AGGGGCC | 628 |
| 613 | GAGGAAG CUGAUGAGGCCGAAAGGCCGAA ACAGGCG | 629 |
| 616 | GAUGAGG CUGAUGAGGCCGAAAGGCCGAA AGGACAG | 630 |
| 617 | GGAUGAG CUGAUGAGGCCGAAAGGCCGAA AAGGACA | 631 |
| 620 | AUGGGAU CUGAUGAGGCCGAAAGGCCGAA AGGAAGG | 632 |
| 623 | AAGAUGG CUGAUGAGGCCGAAAGGCCGAA AUGAGGA | 633 |
| 628 | UGUCAAA CUGAUGAGGCCGAAAGGCCGAA AUCGGAU | 634 |
| 630 | AUUGUCA CUGAUGAGGCCGAAAGGCCGAA AGAUGGG | 635 |
| 631 | GAUUGUC CUGAUGAGGCCGAAAGGCCGAA AAGAUGG | 636 |
| 638 | GGGGCAC CUGAUGAGGCCGAAAGGCCGAA AUUGUCA | 637 |
| 661 | AGAUCUU CUGAUGAGGCCGAAAGGCCGAA AGCUCGG | 638 |
| 667 | CUCGGCA CUGAUGAGGCCGAAAGGCCGAA AUCUUGA | 639 |
| 687 | GCUGCCA CUGAUGAGGCCGAAAGGCCGAA AGUUUCG | 640 |
| 700 | CCCCACC CUGAUGAGGCCGAAAGGCCGAA AGGCAGC | 641 |
| 715 | GUAGGAA CUGAUGAGGCCGAAAGGCCGAA AUCUCAU | 642 |
| 717 | CAGUAAG CUGAUGAGGCCGAAAGGCCGAA AGAUCUC | 643 |
| 718 | ACAGUAG CUGAUGAGGCCGAAAGGCCGAA AAGAUCU | 644 |
| 721 | CACACAG CUGAUGAGGCCGAAAGGCCGAA AGGAAGA | 645 |
| 751 | ACACCUC CUGAUGAGGCCGAAAGGCCGAA AUGUCCU | 646 |
| 759 | CGUGAAA CUGAUGAGGCCGAAAGGCCGAA ACACCUC | 647 |
| 761 | CCCGUGA CUGAUGAGGCCGAAAGGCCGAA AUACACC | 648 |
| 762 | UCCCGUG CUGAUGAGGCCGAAAGGCCGAA AAUACAC | 649 |
| 763 | GUCCCGU CUGAUGAGGCCGAAAGGCCGAA AAAUACA | 650 |
| 792 | CGAAAAG CUGAUGAGGCCGAAAGGCCGAA AGCCUCG | 651 |
| 795 | UUGCGAA CUGAUGAGGCCGAAAGGCCGAA AGGAGCC | 652 |
| 796 | CUUGCGA CUGAUGAGGCCGAAAGGCCGAA AAGGAGC | 653 |
| 797 | GCUUGCG CUGAUGAGGCCGAAAGGCCGAA AAAGGAG | 654 |
| 798 | AGCUUGC CUGAUGAGGCCGAAAGGCCGAA AAAAGGA | 655 |
| 829 | GGAACAC CUGAUGAGGCCGAAAGGCCGAA AUGGCCA | 656 |
| 834 | GGUCCGG CUGAUGAGGCCGAAAGGCCGAA ACACAAU | 657 |
| 835 | GGGUCCG CUGAUGAGGCCGAAAGGCCGAA AACACAA | 658 |
| 845 | GCGUAGG CUGAUGAGGCCGAAAGGCCGAA AGGGGUC | 659 |
| 849 | GUCUGCG CUGAUGAGGCCGAAAGGCCGAA AGGGAGG | 660 |
| 872 | CGCACAG CUGAUGAGGCCGAAAGGCCGAA AGCCUGC | 661 |
| 883 | GCAUGGA CUGAUGAGGCCGAAAGGCCGAA ACACGCA | 662 |
| 885 | CUGCAUG CUGAUGAGGCCGAAAGGCCGAA AGACACG | 662 |
| 905 | CGGUCGG CUGAUGAGGCCGAAAGGCCGAA AGGCCGC | 664 |
| 906 | CCGGUCG CUGAUGAGGCCGAAAGGCCGAA AAGGCCG | 665 |
| 919 | GCUCACU CUGAUGAGGCCGAAAGGCCGAA AGCUCCC | 666 |
| 936 | GUACUGG CUGAUGAGGCCGAAAGGCCGAA AUUCCAU | 667 |
| 937 | GGUACUG CUGAUGAGGCCGAAAGGCCGAA AAUUCCA | 668 |
| 942 | UGGCAGG CUGAUGAGGCCGAAAGGCCGAA ACUGGAA | 669 |
| 953 | UCGUCUG CUGAUGAGGCCGAAAGGCCGAA AUCUGGC | 670 |
| 962 | CGGUGAC CUGAUGAGGCCGAAAGGCCGAA AUCGUCU | 671 |
| 965 | AUCCGGU CUGAUGAGGCCGAAAGGCCGAA ACGAUCG | 672 |

TABLE V-continued

Human rel A HH Ribozyme Sequences

| nt. Sequence | HH Ribozyme Sequence | SEQ ID NO. |
|---|---|---|
| 973 | UCUCCUC CUGAUGAGGCCGAAAGGCCGAA AUCCGGU | 673 |
| 986 | GUCCUUU CUGAUGAGGCCGAAAGGCCGAA AGGUUUC | 674 |
| 996 | GGUCUCA CUGAUGAGGCCGAAAGGCCGAA AUGUCCU | 675 |
| 1005 | GCUCUUG CUGAUGAGGCCGAAAGGCCGAA AGGUCUC | 676 |
| 1006 | UGCUCUU CUGAUGAGGCCGAAAGGCCGAA AAGGUCU | 677 |
| 1015 | UCUUCAU CUGAUGAGGCCGAAAGGCCGAA AUGCUCU | 678 |
| 1028 | CUGAAAG CUGAUGAGGCCGAAAGGCCGAA ACUCCUC | 679 |
| 1031 | CCGCUGA CUGAUGAGGCCGAAAGGCCGAA AGGACUC | 680 |
| 1032 | UCCGCUG CUGAUGAGGCCGAAAGGCCGAA AAGGACU | 681 |
| 1033 | GUCCGCU CUGAUGAGGCCGAAAGGCCGAA AAAGGAC | 682 |
| 1058 | CGAGGUG CUGAUGAGGCCGAAAGGCCGAA AGGCCGG | 683 |
| 1064 | AUGCGUC CUGAUGAGGCCGAAAGGCCGAA AGGUGGA | 684 |
| 1072 | GCACAGC CUGAUGAGGCCGAAAGGCCGAA AUGCGUC | 685 |
| 1082 | CUGCGGG CUGAUGAGGCCGAAAGGCCGAA AGGCACA | 686 |
| 1083 | GCUGCGG CUGAUGAGGCCGAAAGGCCGAA AAGGCAC | 687 |
| 1092 | AGAAGCU CUGAUGAGGCCGAAAGGCCGAA AGCUGCG | 688 |
| 1097 | GGGACAG CUGAUGAGGCCGAAAGGCCGAA AGCUGAG | 689 |
| 1098 | GGGGACA CUGAUGAGGCCGAAAGGCCGAA AAGCUGA | 690 |
| 1102 | GCUUGGG CUGAUGAGGCCGAAAGGCCGAA ACAGAAG | 691 |
| 1125 | AAAGGGA CUGAUGAGGCCGAAAGGCCGAA AGGGCUG | 692 |
| 1127 | GUAAAGG CUGAUGAGGCCGAAAGGCCGAA AUAGGGC | 693 |
| 1131 | UGACGUA CUGAUGAGGCCGAAAGGCCGAA AGGGAUA | 694 |
| 1132 | AUGACGU CUGAUGAGGCCGAAAGGCCGAA AAGGGAU | 695 |
| 1133 | GAUGACG CUGAUGAGGCCGAAAGGCCGAA AAAGGGA | 696 |
| 1137 | CAGGGAU CUGAUGAGGCCGAAAGGCCGAA ACGUAAA | 697 |
| 1140 | GCUCAGG CUGAUGAGGCCGAAAGGCCGAA AUGACGU | 698 |
| 1153 | CAUAGUU CUGAUGAGGCCGAAAGGCCGAA AUGGUGC | 699 |
| 1158 | CUCAUCA CUGAUGAGGCCGAAAGGCCGAA AGUUGAU | 700 |
| 1167 | GGUGGGA CUGAUGAGGCCGAAAGGCCGAA ACUCAUC | 701 |
| 1168 | UGGUGGG CUGAUGAGGCCGAAAGGCCGAA AACUCAU | 702 |
| 1169 | AUGGUGG CUGAUGAGGCCGAAAGGCCGAA AAACUCA | 703 |
| 1182 | AGAAGGA CUGAUGAGGCCGAAAGGCCGAA ACACCAU | 704 |
| 1183 | CAGAAGG CUGAUGAGGCCGAAAGGCCGAA AACACCA | 705 |
| 1184 | CCAGAAG CUGAUGAGGCCGAAAGGCCGAA AAACACC | 706 |
| 1187 | UGCCCAG CUGAUGAGGCCGAAAGGCCGAA AAGAAAC | 707 |
| 1188 | CUGCCCA CUGAUGAGGCCGAAAGGCCGAA AAGGAAA | 708 |
| 1198 | CCUGGCU CUGAUGAGGCCGAAAGGCCGAA AUCUGCC | 709 |
| 1209 | GAAGGCC CUGAUGAGGCCGAAAGGCCGAA AGGCCUG | 710 |
| 1215 | CGGGGCC CUGAUGAGGCCGAAAGGCCGAA AGGCCGA | 711 |
| 1229 | ACUUGGG CUGAUGAGGCCGAAAGGCCGAA AGGGGCC | 712 |
| 1237 | GGGGCAG CUGAUGAGGCCGAAAGGCCGAA ACUUGGG | 713 |
| 1250 | GGGGCUG CUGAUGAGGCCGAAAGGCCGAA AGCCUGG | 714 |
| 1268 | AUGGCUG CUGAUGAGGCCGAAAGGCCGAA AGCAGGG | 715 |
| 1279 | GAGCUGA CUGAUGAGGCCGAAAGGCCGAA ACCAUGG | 716 |
| 1281 | CAGAGCU CUGAUGAGGCCGAAAGGCCGAA AUACCAU | 717 |
| 1286 | UGGGCCA CUGAUGAGGCCGAAAGGCCGAA AGCUGAU | 718 |
| 1309 | GGACUGG CUGAUGAGGCCGAAAGGCCGAA ACAGGGG | 719 |
| 1315 | GGGCUAG CUGAUGAGGCCGAAAGGCCGAA ACUGGGA | 720 |
| 1318 | CUGGGGC CUGAUGAGGCCGAAAGGCCGAA AGGACUG | 721 |
| 1331 | GCCUGAG CUGAUGAGGCCGAAAGGCCGAA AGGGCCU | 722 |
| 1334 | ACAGCCU CUGAUGAGGCCGAAAGGCCGAA AGGAGGG | 723 |
| 1389 | GGCCUCU CUGAUGAGGCCGAAAGGCCGAA ACAGCGU | 724 |
| 1413 | AUCAUCA CUGAUGAGGCCGAAAGGCCGAA ACUGCAG | 725 |
| 1414 | CAUCAUC CUGAUGAGGCCGAAAGGCCGAA AACUGCA | 726 |
| 1437 | GCCAAGC CUGAUGAGGCCGAAAGGCCGAA AGGCCCC | 727 |
| 1441 | UGUUGCC CUGAUGAGGCCGAAAGGCCGAA AGCAAGG | 728 |
| 1467 | GUCUGUG CUGAUGAGGCCGAAAGGCCGAA ACACAGC | 729 |
| 1468 | GGUCUGU CUGAUGAGGCCGAAAGGCCGAA AACACAG | 730 |
| 1482 | GUCGACG CUGAUGAGGCCGAAAGGCCGAA AUGCCAG | 731 |
| 1486 | AGUUGUC CUGAUGAGGCCGAAAGGCCGAA ACGGAUG | 732 |
| 1494 | AAACUCG CUGAUGAGGCCGAAAGGCCGAA AGUUGUC | 733 |
| 1500 | CUGCUGA CUGAUGAGGCCGAAAGGCCGAA ACUCGAA | 734 |
| 1501 | GCUGCUG CUGAUGAGGCCGAAAGGCCGAA AACUCGG | 735 |
| 1502 | AGCUGCU CUGAUGAGGCCGAAAGGCCGAA AAACUCG | 736 |
| 1525 | CCACAGG CUGAUGAGGCCGAAAGGCCGAA AUGCCCU | 737 |
| 1566 | CUCAGGG CUGAUGAGGCCGAAAGGCCGAA ACUCCAU | 738 |
| 1577 | CGAGUUA CUGAUGAGGCCGAAAGGCCGAA AGCCUCA | 739 |
| 1579 | GGCGAGU CUGAUGAGGCCGAAAGGCCGAA AUAGCCU | 740 |
| 1583 | ACCAGGC CUGAUGAGGCCGAAAGGCCGAA AGUUAUA | 741 |
| 1588 | CUGUCAC CUGAUGAGGCCGAAAGGCCGAA AGGCGAG | 742 |
| 1622 | GGAGCAG CUGAUGAGGCCGAAAGGCCGAA AGCUGGG | 743 |
| 1628 | CCCAGUG CUGAUGAGGCCGAAAGGCCGAA AGCAGGA | 744 |
| 1648 | CAUUGGG CUGAUGAGGCCGAAAGGCCGAA AGCCCCG | 745 |
| 1660 | CUGAAAG CUGAUGAGGCCGAAAGGCCGAA AGGCCAU | 746 |

TABLE V-continued

Human rel A HH Ribozyme Sequences

| nt. Sequence | HH Ribozyme Sequence | SEQ ID NO. |
|---|---|---|
| 1663 | CUCCUGA CUGAUGAGGCCGAAAGGCCGAA AGGAGGC | 747 |
| 1664 | UCUCCUG CUGAUGAGGCCGAAAGGCCGAA AAGGAGG | 748 |
| 1665 | AUCUCCU CUGAUGAGGCCGAAAGGCCGAA AAAGGAG | 749 |
| 1680 | GGAGGAG CUGAUGAGGCCGAAAGGCCGAA AGUCUUC | 750 |
| 1681 | UGGAGGA CUGAUGAGGCCGAAAGGCCGAA AAGUCUU | 751 |
| 1683 | AAUGGAG CUGAUGAGGCCGAAAGGCCGAA AGAAGUC | 752 |
| 1686 | CGCAAUG CUGAUGAGGCCGAAAGGCCGAA AGGAGAA | 753 |
| 1690 | UGUCCGC CUGAUGAGGCCGAAAGGCCGAA AUGGAGG | 754 |
| 1704 | GGCUGAG CUGAUGAGGCCGAAAGGCCGAA AGUCCAU | 755 |
| 1705 | GGGCUGA CUGAUGAGGCCGAAAGGCCGAA AAGUCCA | 756 |
| 1707 | CAGGGCU CUGAUGAGGCCGAAAGGCCGAA AGAAGUC | 757 |
| 1721 | CUGAUCU CUGAUGAGGCCGAAAGGCCGAA ACUCAGC | 758 |
| 1726 | AGGAGCU CUGAUGAGGCCGAAAGGCCGAA AUCUGAC | 759 |
| 1731 | CCCUUAG CUGAUGAGGCCGAAAGGCCGAA AGCUGAU | 760 |
| 1734 | ACCCCCU CUGAUGAGGCCGAAAGGCCGAA AGGAGCU | 761 |
| 1754 | CUCUGGG CUGAUGAGGCCGAAAGGCCGAA AGGGCAG | 762 |

TABLE VI

Human rel A Hairpin Ribozyme/Target Sequences

| nt. Position | Hairpin Ribozyme sequence | Seq ID No. | Substrate | Seq ID No. |
|---|---|---|---|---|
| 90 | UGAGGGGG AGAA GUUC ACCAGAGAAACACACGUUGUGGUACAUUACCUGGUA | 763 | GAACU GUU CCCCCUCA | 778 |
| 156 | GCUGCUUG AGAA GCUC ACCAGAGAAACACACGUUGUGGUACAUUACCUGGUA | 764 | GAGCA GCC CAAGCAGC | 779 |
| 362 | GCCAUCCC AGAA GUCC ACCAGAGAAACACACGUUGUGGUACAUUACCUGGUA | 765 | GGACU GCC GGGAUGGC | 780 |
| 413 | GUUCUGGA AGAA GUGG ACCAGAGAAACACACGUUGUGGUACAUUACCUGGUA | 766 | CCACA GUU UCCAGAAC | 781 |
| 606 | GAAGGACA AGAA GCAG ACCAGAGAAACACACGUUGUGGUACAUUACCUGGUA | 767 | CUGCC GCC UGUCCUUC | 782 |
| 652 | UUGAGCUC AGAA GUGU ACCAGAGAAACACACGUUGUGGUACAUUACCUGGUA | 768 | ACACU GCC GAGCUCAA | 783 |
| 695 | CCCACCGA AGAA GCUG ACCAGAGAAACACACGUUGUGGUACAUUACCUGGUA | 769 | CAGCU GCC UCGGUGGG | 784 |
| 853 | AGGCUGGG AGAA GCGU ACCAGAGAAACACACGUUGUGGUACAUUACCUGGUA | 770 | ACGCA GAC CCCAGCCU | 785 |
| 900 | GGUCGGAA AGAA GCCG ACCAGAGAAACACACGUUGUGGUACAUUACCUGGUA | 771 | CGGCC GCC UUCCGACC | 786 |
| 955 | UGACGAUC AGAA GUAU ACCAGAGAAACACACGUUGUGGUACAUUACCUGGUA | 772 | AUACA GAC GAUCGUCA | 787 |
| 1037 | GUCGGUGG AGAA GCUG ACCAGAGAAACACACGUUGUGGUACAUUACCUGGUA | 773 | CAGCG GAC CCACCGAC | 788 |
| 1045 | GGCCGGGG AGAA GUGG ACCAGAGAAACACACGUUGUGGUACAUUACCUGGUA | 774 | CCACC GAC CCCCGGCC | 789 |
| 1410 | CAUCAUCA AGAA GCAG ACCAGAGAAACACACGUUGUGGUACAUUACCUGGUA | 775 | CUGCA GUU UGAUGAUG | 790 |
| 1453 | ACAGCUGG AGAA GUGC ACCAGAGAAACACACGUUGUGGUACAUUACCUGGUA | 776 | GCACA GAC CCAGCUGU | 791 |
| 1471 | GAUGCCAG AGAA GUGA ACCAGAGAAACACACGUUGUGGUACAUUACCUGGUA | 777 | UCACA GAC CUGGCAUC | 792 |

TABLE VII

Mouse rel A Hairpin Ribozyme/Target Sequences

| nt. Position | Hairpin Ribozyme sequence | Seq ID No. | Substrate | Seq ID No. |
|---|---|---|---|---|
| 137 | GUUGCUUC AGAA GUUC ACCAGAGAAACACACGUUGUGGUACAUUACCUGGUA | 793 | GAACA GCC GAAGCAAC | 812 |
| 273 | GAGAUUCG AGGA GUUC ACCAGAGAAACACACGUUGUGGUACAUUACCUGGUA | 794 | GAACA GUU CGAAUCUC | 813 |
| 343 | GCCAUCCC AGAA GUCC ACCAGAGAAACACACGUUGUGGUACAUUACCUGGUA | 795 | GGACU GCC GGGAUGGC | 814 |
| 366 | GGGCAGAG AGAA GCCU ACCAGAGAAACACACGUUGUGGUACAUUACCUGGUA | 796 | AGGCU GAC CUCUGCCC | 815 |
| 633 | UUGAGCUC AGAA GUGU ACCAGAGAAACACACGUUGUGGUACAUUACCUGGUA | 797 | ACACU GCC GAGCUCAA | 816 |
| 676 | CCCACCGA AGAA GCUC ACCAGAGAAACACACGUUGUGGUACAUUACCUGGUA | 798 | GAGCU GCC UCGGUGGG | 817 |
| 834 | AGGCUGGG AGAA GCGU ACCAGAGAAACACACGUUGUGGUACAUUACCUGGUA | 799 | ACGCC GAC CCCAGCCU | 818 |
| 881 | GAUCAGAA AGAA GCCG ACCAGAGAAACACACGUUGUGGUACAUUACCUGGUA | 800 | CGGCG GCC UUCUGAUC | 819 |
| 1100 | AGGUGUAG AGAA GCGG ACCAGAGAAACACACGUUGUGGUACAUUACCUGGUA | 801 | CCGCA GCC CUACACCU | 820 |
| 1205 | GGGCAGAG AGAA GUGC ACCAGAGAAACACACGUUGUGGUACAUUACCUGGUA | 802 | GCACC GUC CUCUGCCC | 821 |
| 1361 | GGGCUUCC AGAA GCGU ACCAGAGAAACACACGUUGUGGUACAUUACCUGGUA | 803 | ACGCU GUC GGAAGCCC | 822 |
| 1385 | CAGCAUCA AGAA GCAG ACCAGAGAAACACACGUUGUGGUACAUUACCUGGUA | 804 | CUGCA GUU UGAUGCUG | 823 |
| 1431 | ACUCCUGG AGAA GUGC ACCAGAGAAACACACGUUGUGGUACAUUACCUGGUA | 805 | GCACA GAC CCAGGAGU | 824 |
| 1449 | GAUGCCAG AGAA GUGA ACCAGAGAAACACACGUUGUGGUACAUUACCUGGUA | 806 | UCACA GAC CUGGCAUC | 825 |
| 1802 | AAGUCGGG AGAA GCUG ACCAGAGAAACACACGUUGUGGUACAUUACCUGGUA | 807 | CAGCU GCC CCCGACUU | 826 |
| 2009 | UGGCUCCA AGAA GUCC ACCAGAGAAACACACGUUGUGGUACAUUACCUGGUA | 808 | GGACA GAC UGGAGCCA | 827 |
| 2124 | UGGGUGCG AGAA GCAC ACCAGAGAAACACACGUUGUGGUACAUUACCUGGUA | 809 | GUGCU GCC CGACACCA | 828 |
| 2233 | AUUCUGAA AGAA GCCA ACCAGAGAAACACACGUUGUGGUACAUUACCUGGUA | 810 | UGGCC GCC UUCAGAAU | 829 |
| 2354 | UCAGUAAA AGAA GUCU ACCAGAGAAACACACGUUGUGGUACAUUACCUGGUA | 811 | AGACA GCC UUUACUGA | 830 |

We claim:

1. An enzymatic RNA molecule which specifically cleaves rel A mRNA.

2. An enzymatic RNA molecule of claim 1, the binding arms of which contain sequences complementary to the sequences defined in Table II.

3. The enzymatic RNA molecule of claim 1, the binding arms of which contain sequences complementary to the sequences defined in any one of Tables III, and IV–VII.

4. The enzymatic RNA molecule of claims 1, 2, or 3, wherein said RNA molecule is in a hammerhead motif.

5. The enzymatic RNA molecule of claim 1, 2, or 3, wherein said RNA molecule is in a hairpin, hepatitis delta virus, group 1 intron, VS RNA or RNAseP RNA motif.

6. The enzymatic RNA molecule of claim 6, wherein said ribozyme comprises between 12 and 100 bases complementary to said mRNA.

7. The enzymatic RNA molecule of claim 6, wherein said ribozyme comprises between 14 and 24 bases complementary to said mRNA.

8. Enzymatic RNA molecule consisting essentially of any sequence selected from the group of those shown in Tables IV, V, VI, and VII.

9. A mammalian cell in vitro including an enzymatic RNA molecule of claims 1, 2, or 3.

10. The cell of claim 9, wherein said cell is a human cell.

11. An expression vector including a nucleic acid encoding an enzymatic RNA molecule or multiple enzymatic molecules of claims 1, 2, or 3 in a manner which allows expression of that enzymatic RNA molecule(s) within a mammalian cell in vitro.

12. A mammalian cell in vitro including an expression vector of claim 11.

13. The cell of claim 13, wherein said cell is a human cell.

* * * * *